(12) United States Patent
Meinhart et al.

(10) Patent No.: US 11,883,762 B2
(45) Date of Patent: *Jan. 30, 2024

(54) MICROFLUIDIC-BASED APPARATUS AND METHOD FOR VAPORIZATION OF LIQUIDS

(71) Applicant: Numerical Design, Inc., Santa Barbara, CA (US)

(72) Inventors: Carl D. Meinhart, Santa Barbara, CA (US); Brian Piorek, Santa Barbara, CA (US); Nicholas B. Judy, Santa Barbara, CA (US)

(73) Assignee: Numerical Design, Inc., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/472,663

(22) Filed: Sep. 12, 2021

(65) Prior Publication Data

US 2022/0203258 A1 Jun. 30, 2022

Related U.S. Application Data

(63) Continuation of application No. 15/716,049, filed on Sep. 26, 2017, now Pat. No. 11,117,068, which is a (Continued)

(51) Int. Cl.
*B01B 1/00* (2006.01)
*F24F 6/02* (2006.01)
(Continued)

(52) U.S. Cl.
CPC ............... *B01B 1/005* (2013.01); *A61L 9/03* (2013.01); *B05B 7/1686* (2013.01); *F16T 1/00* (2013.01);
(Continued)

(58) Field of Classification Search
CPC ........ A61L 9/037; A61L 9/03; A61L 2209/11; A61L 2209/135; B01B 1/005;
(Continued)

(56) References Cited

U.S. PATENT DOCUMENTS

2009/0326279 A1* 12/2009 Tonkovich ............ B01F 25/431
422/198
2015/0367016 A1* 12/2015 Gruenbacher ......... B41J 2/1753
137/334

* cited by examiner

*Primary Examiner* — Dana Ross
*Assistant Examiner* — Joe E Mills, Jr.
(74) *Attorney, Agent, or Firm* — Mark Rodgers

(57) ABSTRACT

Methods and apparatus for vaporizing liquid from a liquid source into the surrounding environment, are disclosed, where the apparatus comprises at least one manifold comprising at least one liquid port formed by a through-hole and at least one ridge structure, wherein the liquid port is in fluid communication with the liquid source and the one ridge structure At least one vaporization port is included in a planar structure connecting a first side of the structure to a second side, in fluid communication with the at least one ridge structure and the surrounding environment, wherein fluid flow through the liquid and vaporization ports is substantially perpendicular to the plane of the structure, and the ridge structures are substantially parallel to the plane of the structure. At least one heating element is present that is in thermal communication to the at least one vaporization port and at least one ridge structure.

9 Claims, 61 Drawing Sheets

Related U.S. Application Data continuation-in-part of application No. 15/171,801, filed on Jun. 2, 2016, now abandoned, and a continuation-in-part of application No. 15/171,852, filed on Jun. 2, 2016, now Pat. No. 10,612,770, which is a continuation-in-part of application No. 14/885,822, filed on Oct. 16, 2015, now Pat. No. 10,502,409, said application No. 15/171,801 is a continuation-in-part of application No. 14/885,822.

(60) Provisional application No. 62/081,476, filed on Nov. 18, 2014, provisional application No. 62/066,320, filed on Oct. 20, 2014.

(51) Int. Cl.
| | | |
|---|---|---|
| *F22B 1/28* | (2006.01) | |
| *H05B 1/02* | (2006.01) | |
| *F24F 6/04* | (2006.01) | |
| *B05B 7/16* | (2006.01) | |
| *F16T 1/00* | (2006.01) | |
| *H05B 3/26* | (2006.01) | |
| *A61L 9/03* | (2006.01) | |
| *F28D 15/04* | (2006.01) | |
| *B01J 19/00* | (2006.01) | |
| *F24F 8/50* | (2021.01) | |
| *H05B 3/02* | (2006.01) | |

(52) U.S. Cl.
CPC .............. *F22B 1/284* (2013.01); *F24F 6/025* (2013.01); *H05B 1/0283* (2013.01); *H05B 3/02* (2013.01); *A61L 9/037* (2013.01); *A61L 2209/11* (2013.01); *A61L 2209/135* (2013.01); *B01J 19/0093* (2013.01); *F24F 8/50* (2021.01); *F28D 15/046* (2013.01)

(58) Field of Classification Search
CPC .... F22B 1/284; B01J 19/0093; B05B 7/1686; F16T 1/00; F24F 2003/1689; F24F 6/025; F24F 6/043; F25B 41/06; F28D 15/046; H05B 1/0283; H05B 3/26
See application file for complete search history.

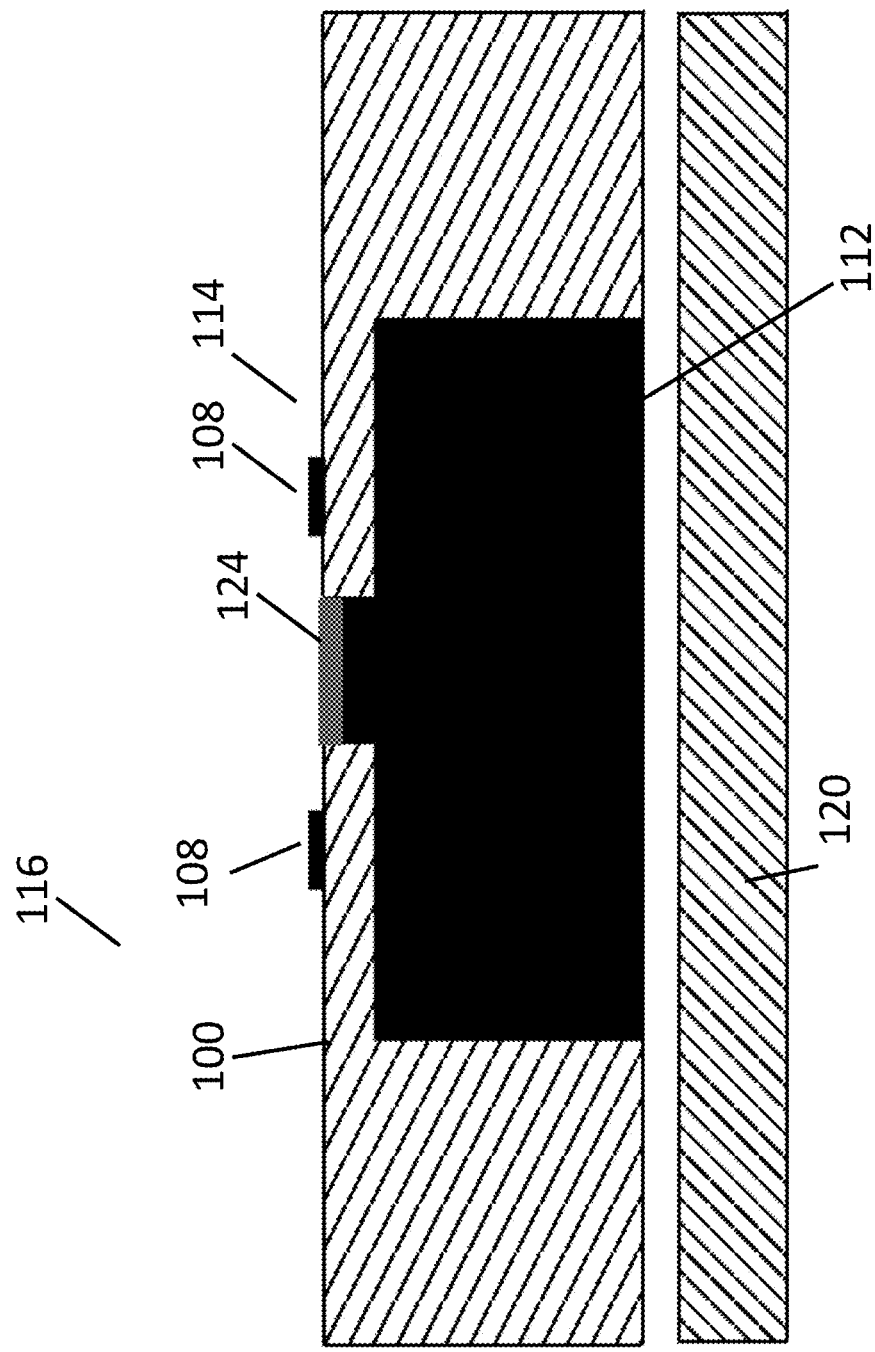

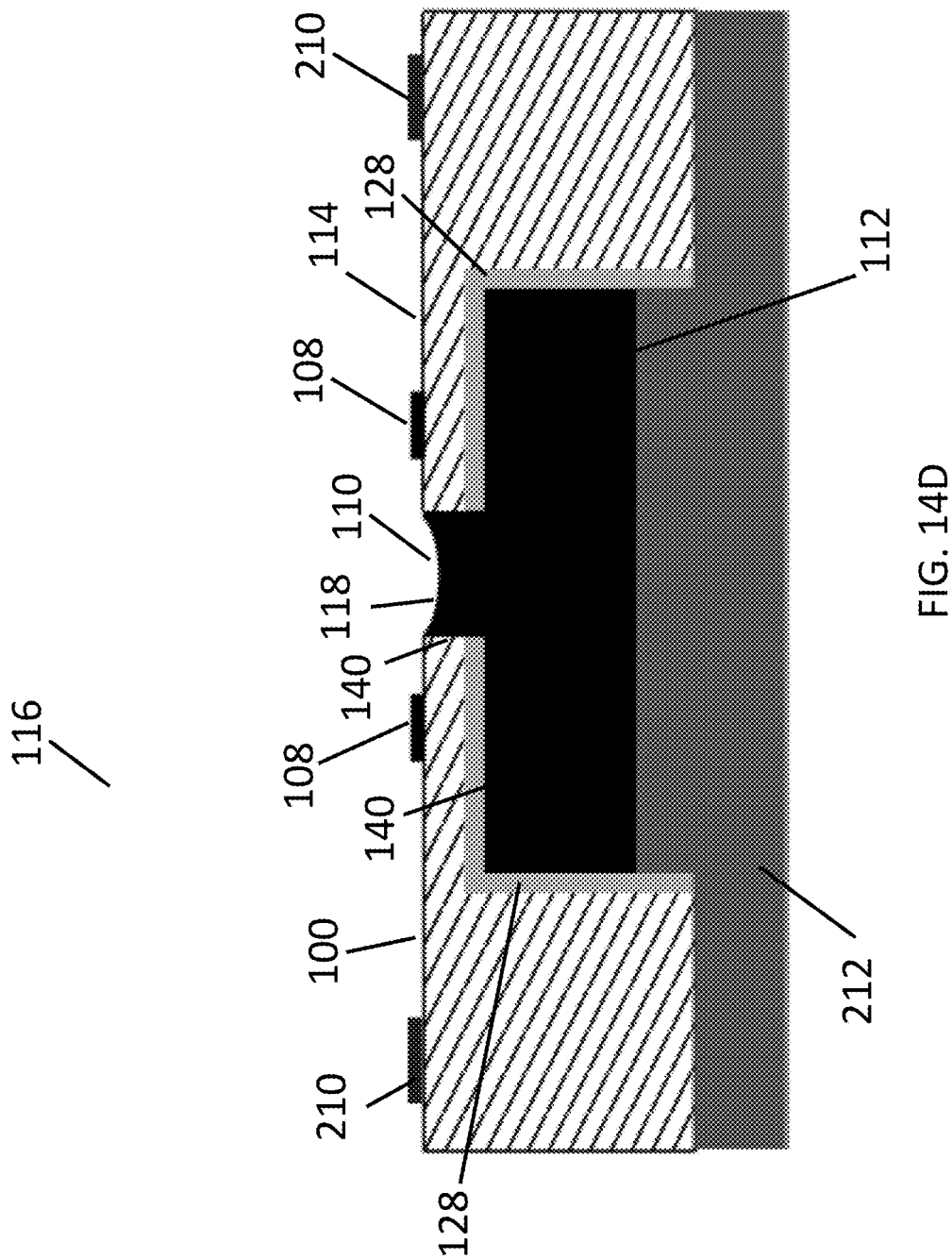

MICROFLUIDIC-BASED APPARATUS AND METHOD FOR VAPORIZATION OF LIQUIDS

CROSS-REFERENCE TO RELATED APPLICATIONS

This application is a Continuation in Part of U.S. utility application Ser. No. 15/171,801, filed Jun. 2, 2016, Ser. No. 15/171,852, filed Jun. 2, 2016, and Ser. No. 14/885,822, filed Oct. 15, 2015, which in turn claims priority to U.S. provisional Application Ser. Nos. 62/066,320 filed Oct. 20, 2014 and Ser. No. 62/081,476 filed Nov. 18, 2014, all of which are incorporated by reference in their entirety.

BACKGROUND

This specification relates to an apparatus and methods for vaporizing liquids and in particular a vaporizer providing well-controlled spatial distributions of vapor, with controlled and accurate dosage of vapor, with well-controlled vaporization temperature profiles, and with high thermodynamic efficiency.

Vaporizers, such as e-cigarettes, humidifiers and other personal as well as medical vaporizers and fragrance vaporizers are becoming increasingly common. Many such vaporizers rely on techniques which have been prevalent for many years. Such vaporizers may benefit from new design approaches and modern fabrication capabilities.

SUMMARY

In some embodiments an apparatus may be microfabricated using batch fabrication techniques, the devices can be manufactured to be nearly identical from device to device. Microfabrication allows the devices to be manufactured in large volumes with high unit-to-unit reproducibility and low per-unit cost. These techniques also allow for controlled fluid flow and fluid heating through the use of micromachined flow control structures.

In a first aspect, a vaporization apparatus may be provided that may be placed within a surrounding environment and configured to vaporize liquid from a liquid source into the surrounding environment, including; at least one manifold comprising at least one liquid port formed by a through-hole and at least one flow channel, wherein the liquid port may be in fluid communication with the liquid source and the flow channel; at least one vaporization port in a planar structure connecting a first side of the structure to a second side, that may be in fluid communication with the at least one flow channel and the surrounding environment, wherein fluid flow through the liquid ports and vaporization ports may be substantially perpendicular to the plane of the structure, and the flow channels may be substantially parallel to the plane of the structure; and, at least one heating element that may be in thermal communication to the at least one vaporization port and at least one flow channel.

In one embodiment of the first aspect the apparatus may be made of glass. In another embodiment of the first aspect the apparatus may be formed from at least two planar etched glass substrates. In one embodiment of the first aspect the at least one flow channel mat be partially enclosed. In another embodiment of the first aspect the flow channels may include at least two regions of differing hydraulic diameter.

In one embodiment of the first aspect the larger hydraulic diameter region may be in fluid communication with the liquid ports and the smaller hydraulic diameter region may be in fluid communication with the vaporization ports. In another embodiment of the first aspect an opening may be disposed below the heating element and the ports, wherein the opening may provide a thermal barrier to reduce heat conduction from the manifold to the liquid source. In one embodiment of the first aspect a first region may include flow channels with a hydraulic diameter is at least 1.25 times larger than a second hydraulic diameter disposed in a second region.

In another embodiment of the first aspect the apparatus may include pillars that are disposed to be in contact with the liquid source. In one embodiment of the first aspect the pillars may range in dimension from 10 um to 200 um. In another embodiment of the first aspect the at least one flow channel may include of a plurality of walls, wherein at least one wall may be disposed to partially occlude at least one vaporization port. In one embodiment of the first aspect the at least one wall may be disposed to partially occlude at least one liquid port. In another embodiment of the first aspect all dimensions may range from 1 um to 1000 um. In one embodiment of the first aspect all dimensions may range from 10 um to 300 um.

In a second aspect a vaporization apparatus may be provided that may be placed within a surrounding environment and configured to vaporize liquid into the surrounding environment, including; at least one manifold structure including at least one liquid port and at least one flow channel, wherein the liquid port may be in fluid communication with a liquid source and the flow channel; at least one vaporization port that may be formed by at least one through-hole in a structure connecting a first side of the structure to a second side, that may be in fluid communication with the at least one flow channel and the surrounding environment; and, at least one heating element that is in thermal communication to the at least one vaporization port and at least one flow channel.

In a third aspect, a method may be provided for vaporizing liquid into a surrounding environment, including; directing liquid from a liquid source through at least one liquid port into at least one flow channel, wherein liquid may flow through the flow channel to a vaporization port, wherein the flow channel and the vaporization port may be formed from at least two planar structures positioned in planar contact; applying heat to the liquid in the flow channel and the vaporization port with an at least one heating element located in thermal communication to the flow channel and vaporization port, and; releasing vaporized liquid through the vaporization port into the surrounding environment so that fluid may be transported from a first side of the at least two planar structures to a second side of the planar structure.

In one embodiment of the third aspect flow through the liquid ports and vaporization ports may be substantially perpendicular to the plane of the at least two planar structures. In another embodiment of the third aspect flow through the flow channels may be substantially parallel to the plane of the at least two planar structures.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIG. 12 depicts an illustrative embodiment that has an optional bulk heater or cooler.

FIGS. 14A, 14B, 14C, and 14D depict various illustrative embodiments of the apparatus.

DETAILED DESCRIPTION

Figure 1:
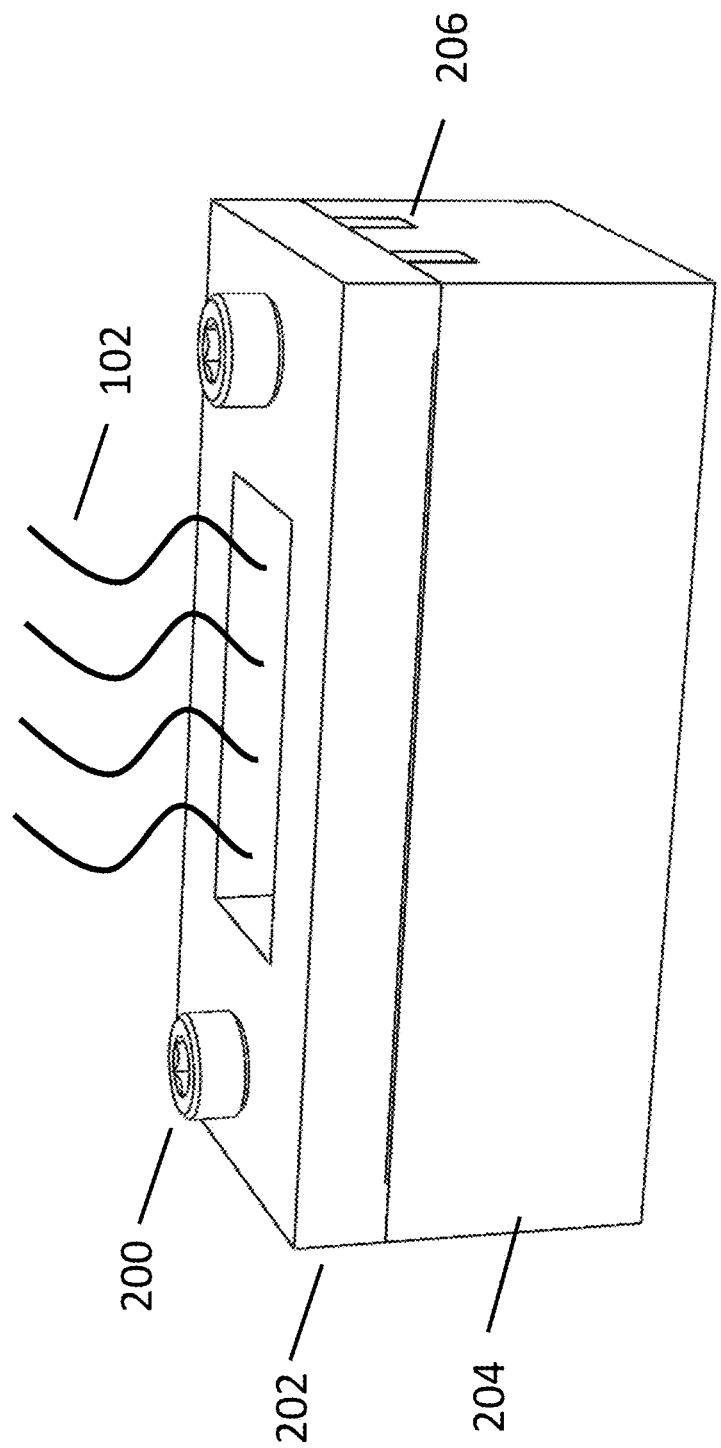
FIG. 1 shows a perspective view of the apparatus of an illustrative embodiment.

Generally described, aspects of the present disclosure relate to vaporizers produced using fine scale microfabrication techniques for both the structure and heating element. Microfabrication may include patterning, etching, deposition, injection and related processes on such materials as glass, metals, plastics and crystalline materials such as silicon and silicon derivatives. Heating elements may include electronic circuits made from electrical components including resistors, capacitors, transistors, logic element and the like which also may be fabricated onto application specific circuits and/or made up of discrete components in any combination.

One or more embodiments described herein may provide well-controlled heating, thus minimizing the effect of the liquid to become excessively hot, thus minimizing undesirable chemical reactions that produce undesirable and/or harmful chemical reaction products.

One or more embodiments described herein may provide vaporization devices manufactured in a highly controlled manner, thus reducing significant variation from unit to unit, and thereby reducing variation in performance.

One or more embodiments described herein may provide vaporizers which are thermodynamically efficient, and less bulky in size.

Microfluidic vaporizers disclosed here may be used to provide efficient vaporization of low-volatility liquids for a large range of applications, including fragrance distribution, medical vaporization, vaporized drug delivery, chemical distillation, chemical-reaction control, aromatics, waxes, scented waxes, air sterilization, theatrical smoke, fog machines, aroma therapy, essential oils, personal vaporizers, chemical vapor or aerosol detector calibration devices, smoking articles, and electronic cigarettes.

Vaporization devices are a general class of devices used to create vapors or aerosols from liquids. Vaporizers have many applications, including but not limited to: fragrance distribution, medical vaporization, vaporized drug delivery, chemical distillation, chemical-reaction control, aromatics, waxes, scented waxes, air sterilization, theatrical smoke, fog machines, aroma therapy, essential oils, personal vaporizers, smoking articles and electronic cigarettes, among others.

The present disclosure describes embodiments, where the vaporization device is microfabricated using modern microfabrication techniques, including lithography, deposition and etching techniques. Such techniques may be applied advantageously to vaporizer design. For example, an embodiment could have micron-scale precision components. In yet other embodiments, the disclosed apparatus and methods could be compatible with injection molded plastics. In an embodiment, the vaporization apparatus and method could have similar geometries from unit to unit. Furthermore, an embodiment could be produced at a low cost in high production volume.

The current application discloses an embodiment which may provide desirable performance improvements. For example, in an embodiment, the micron-scale precision of the components allows for accurate dosing of a vaporized material, and precisely-controlled temperature, which can eliminate overheated regions that produce undesirable chemical reaction products. In additional embodiments, the apparatus can be designed to minimize parasitic heat transfer to the substrate, surrounding environment or interposer. In some embodiments, the apparatus can be made very small, planar and highly portable. The micron-scale features can improve the thermodynamic efficiency of the apparatus and method, and could have minimal energy requirements. In yet another embodiment, the vaporization ports could be individually addressed and activated in a controlled fashion, so that a chemical reaction front or precise release of particular chemicals based on time and individual position within the array of vaporization ports could be established.

FIG. 1 shows a schematic of a vaporization unit for an illustrative embodiment. The unit comprises a microfluidic device (not shown) for vaporization that is contained within a plastic housing commonly referred to as an interposer body 204. The interposer body 204 can be mated to an interposer retaining ring 202 by bolt 200. An electrical interconnect 206 can be used to deliver electrical energy. Vapor 102 can emanate from the apparatus.

Figure 2A:
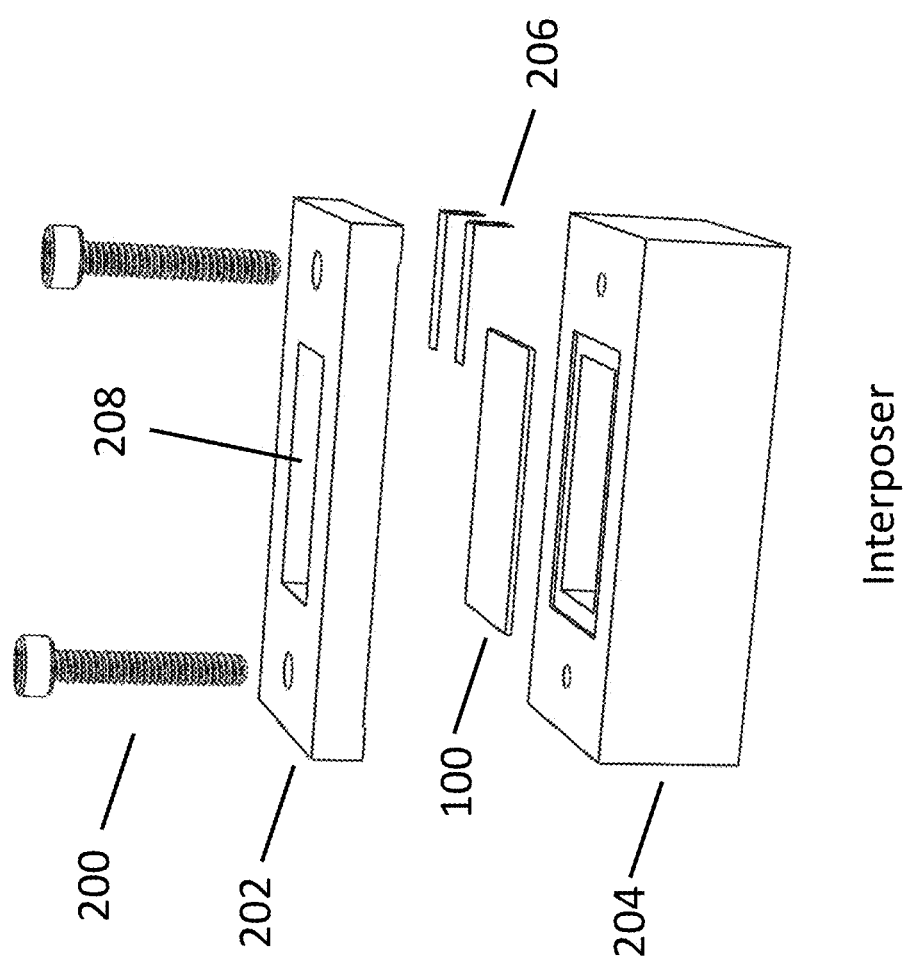
FIGS. 2A and 2B show an exploded view and a cross sectional view of an illustrative embodiment.
Figure 2B:
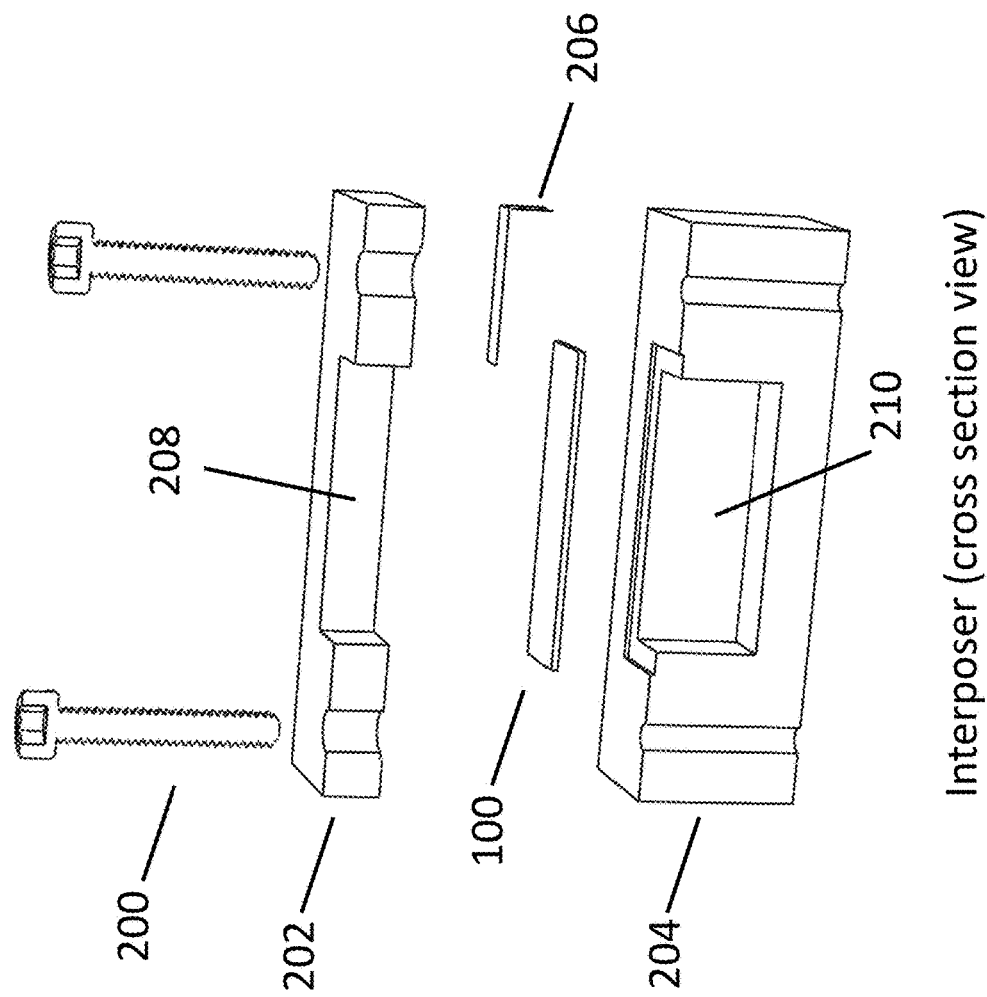

FIG. 2A and FIG. 2B depict an exploded view of an embodiment. The interposer body 204 and interposer retaining ring 202 are in communication with vaporizing structure 100. Vaporizing structure 100 can be comprised of a microfluidic chip. Vapor region 208 is in communication with structure 100 and allows vapor to emanate from microfluidic device structure 100. Electrical interconnect 206 is in electrical communication with microfluidic device structure 100.

In an embodiment, the interposer body 204 is comprised of injection-molded plastic and designed for ease of assembly. In other embodiments, the interposer body 204 can be 3-D printed, machined, and can be made from a large selection of plastics, metals, fiberglass, composites, ceramics, or other structural materials.

Electrical interconnects 206 allow the device to be connected an electronic control unit (not shown). In an embodiment, the electrical interconnects could be formed from a conducting tape, flat wire, wire bond, bump bond, solder bond or other connection process.

In one illustrative embodiment, the overall dimensions of the plastic housing could be nominally 4 mm×6 mm×12 mm. In other embodiments, the plastic housing could range in dimensions from less than 0.1 mm to more than 100 mm, and could contain one or more microfluidic devices.

Figure 3A:
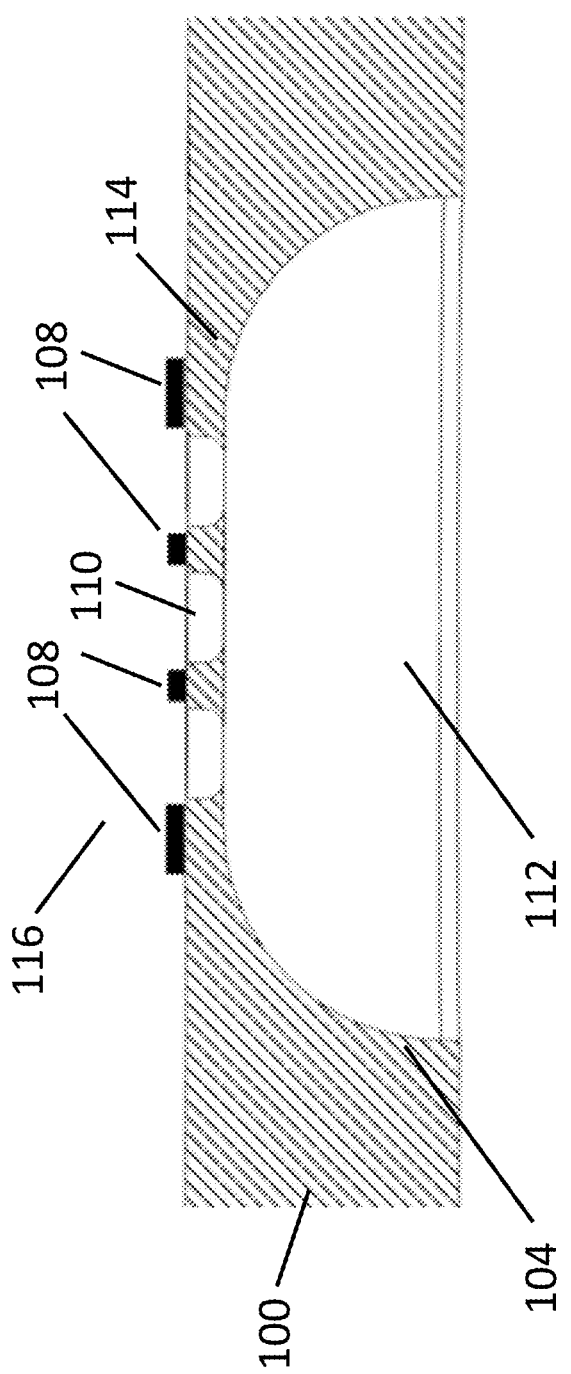
FIGS. 3A and 3B show a profile view, and a perspective view of an illustrative embodiment.
Figure 3B:
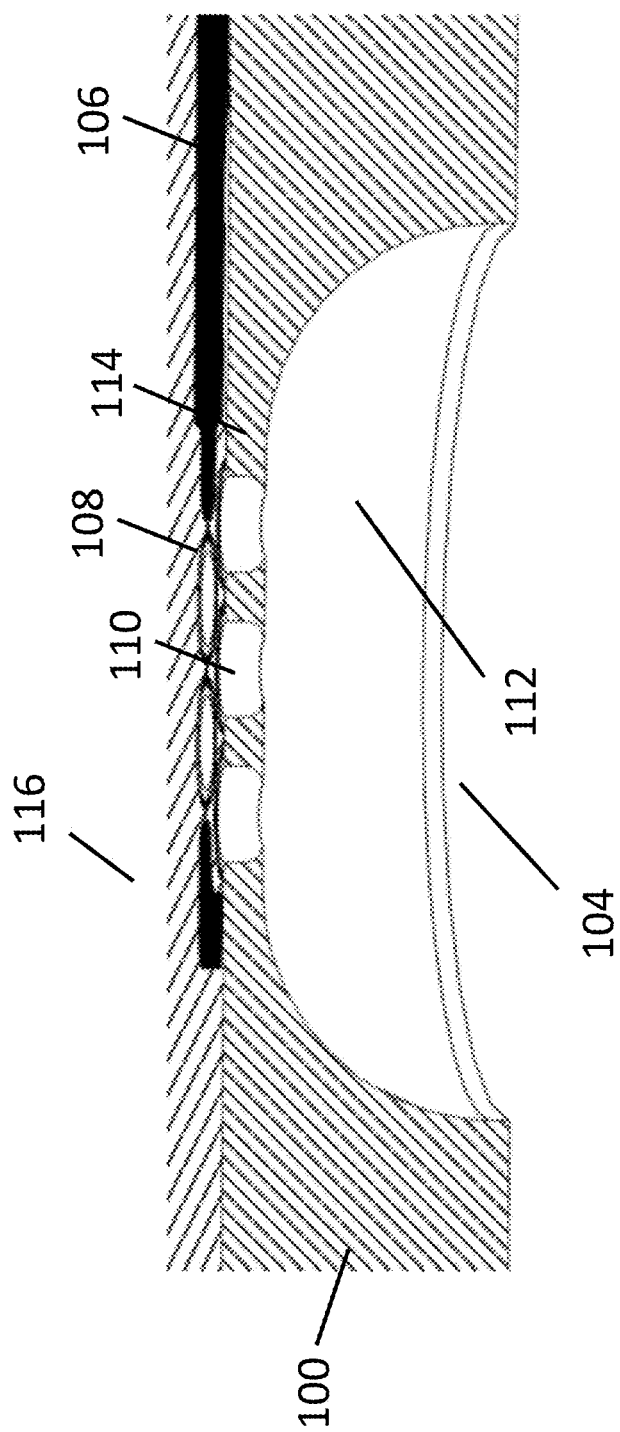

FIG. 3 shows a cross-section view of the apparatus depicting the various components of an embodiment. FIG. 3A is a side view and FIG. 3B is tilted slightly to show the top surface. The surrounding environment 116 is above the structure 100. Vaporization ports 110 are formed in the structure and are in fluid communication with the liquid source 112 and the surrounding environment 116. Liquid source 112 is a region of the structure in fluid communication with a liquid reservoir, not shown and with the vaporizer port region of the apparatus. A heating element 108 is in thermal communication with the vaporization port 110 and located on a structural region 114, which in some embodiments may be a thinned region of the structure. Heating element 108 is in electrical communication with electrode leads 106. A vaporization cluster 104 is region that contains a collection of vaporization ports 110 that are in close proximity with one or more vaporization ports 110. In some embodiments, liquid source 112 may be a wax or otherwise solid phase material which exists in the liquid phase near vaporization port 110 due to the addition of heat.

In the current context, thermal communication refers to the ability to readily transfer thermal energy through heat conduction from one region of the apparatus to another region of the apparatus. In some embodiments, thermal communication occurs between two regions when the distance between those regions is substantially smaller than other dimensions in the apparatus, or the thermal conductivity of the material connecting the two regions is equal to or larger than the thermal conductivity of materials in other regions of the apparatus. In some embodiments heating element 108 can be in thermal communication with vaporization port 110, because the lateral distance between the two components could range between 5 um to 100 um. In some embodiments, the distance between heating element 108 and vaporization port 110 could range from 0.5 um-1 mm. This distance could be substantially smaller than other dimensions of the apparatus. In an illustrative embodiment, the depth of structure 100 could range between 10 um-1000 um, and the lateral size of structure 100 could range between 1 mm-100 mm or even larger.

For clarity, a fluid can be defined as a material that flows and conforms to the shape of its container. Fluids can be comprised of liquid-phase material, gas-phase material, (including vapor), or combinations thereof, such as aerosols. Additionally, even solid particles are considered a fluid when suspended in a liquid or gas medium or are otherwise mobile such that material conforms to the shape of a container.

In the current context, fluid flow through the depth of the structure refers to fluid being transported through the smaller dimension of structure 100, which can be comprised of a substrate with a smaller dimension (i.e. thickness) of between 10 μm-1000 μm, while the lateral size of structure 100 could range between 1 mm-100 mm or even larger. Fluid can be transported through the depth of the structure from one side to another using at least one via or through-hole (i.e. at least one vaporization port 110) formed through the smaller dimension (i.e. thickness) of structure 100. The term fluid refers to the vaporizing liquid, the resulting vapor, aerosol, air, gas, and any combination thereof.

In the current context, vaporization refers to the process of heating a liquid such that the liquid evaporates (or thin film boils, or nucleate boils) into a vapor, thereby transferring mass across a meniscus that separates the liquid and vapor phases of the fluid. In many embodiments, the vapor may subsequently decrease in temperature and may condense to form an aerosol, when combined with ambient air or another gas that has a temperature lower than the vaporization temperature. The process of vaporization may result in generation of an aerosol.

In some embodiments, liquid is located substantially on one side of structure 100 (say the back-side or bottom-side), vapor is located substantially on the opposite side of structure 100 (say the front-side or top-side), and a combination of liquid and vapor can be located in at least one vaporization port 110 (which is a via or through-hole).

FIG. 3A shows an illustrative embodiment, where the thin structural region 114 is nominally 40 um thick. In some embodiments the thin structural region 114 can range from 1 um to 100 um. In yet other embodiments, the thickness of the thin structural region 114 can vary from 1 um to 1000 um.

FIG. 4 shows profile views of illustrative embodiments. The surrounding environment 116 is above the structure 100. A vaporization port 110 is formed in the structure 100 and is in fluid communication with the liquid source 112 region and the surrounding environment 116. A heating element 108 is in close proximity to vaporization port 110. In an illustrative embodiment, heating element 108 could be located within 5-100 um (or 0.5 um to 1 mm) of vaporization port 110. In an illustrative embodiment, heating element 108 is located within 0.5-1000 um. Meniscus 118 defines the vapor and liquid interface. A thin structural region 114 can be formed in structure 100. A contact area 140 can be formed between the liquid from the liquid source 112 and the thin structural region 114.

In some embodiments the thin structural region 114 could be adjacent to the vaporization ports 110 and the heating elements 108, which could minimize parasitic heat transfer to the bulk structure 100. In some embodiments meniscus 118, which separates the liquid in the vaporization port and the surrounding environment, could have curvature, which could create a difference in pressure between the liquid source 112 and the surrounding environment 116. In some embodiments, there is significant contact surface area 140 between the thin structural region 114 and the liquid contained in a vaporization port 110 and the liquid source 112.

Figure 4A:
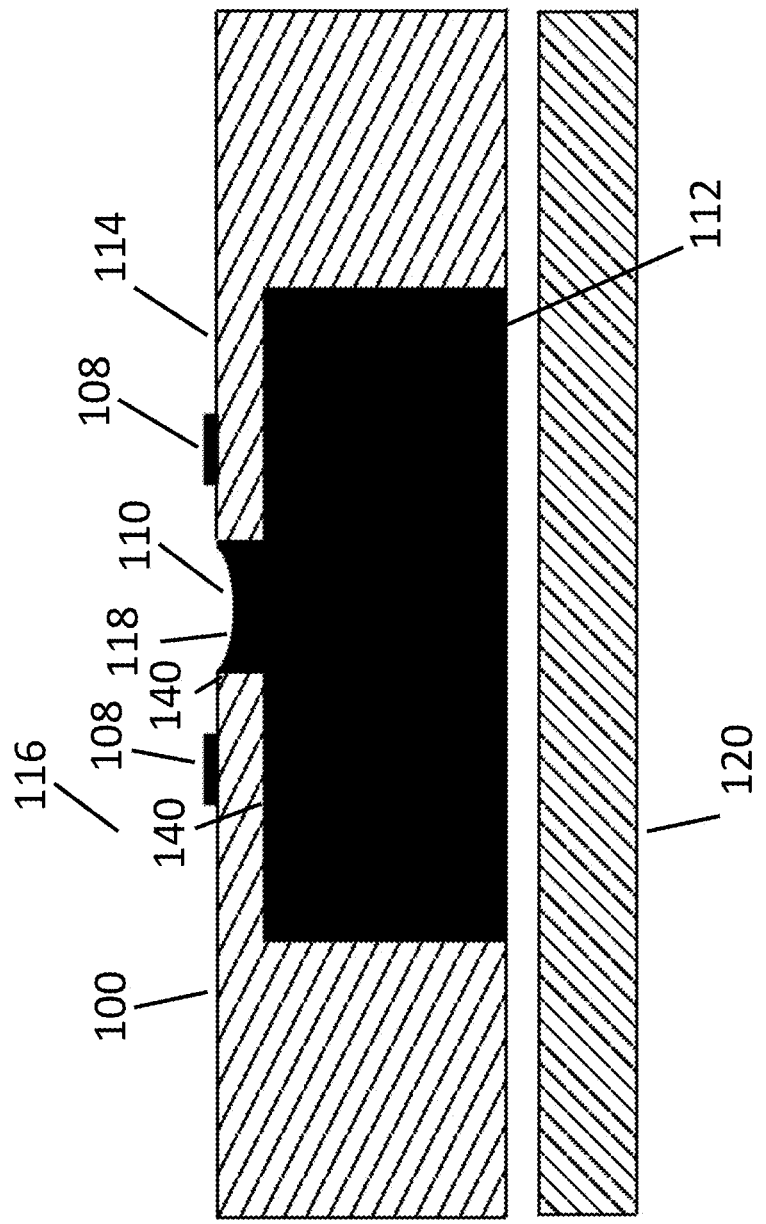
FIGS. 4A, 4B and 4C show profile views of the apparatus depicting components of an illustrative embodiment.

FIG. 4A depicts an illustrative embodiment where an optional bulk heater or cooler 120 could be located in thermal communication to liquid source region 112, to control the bulk temperature of the liquid source 112.

Figure 4B:
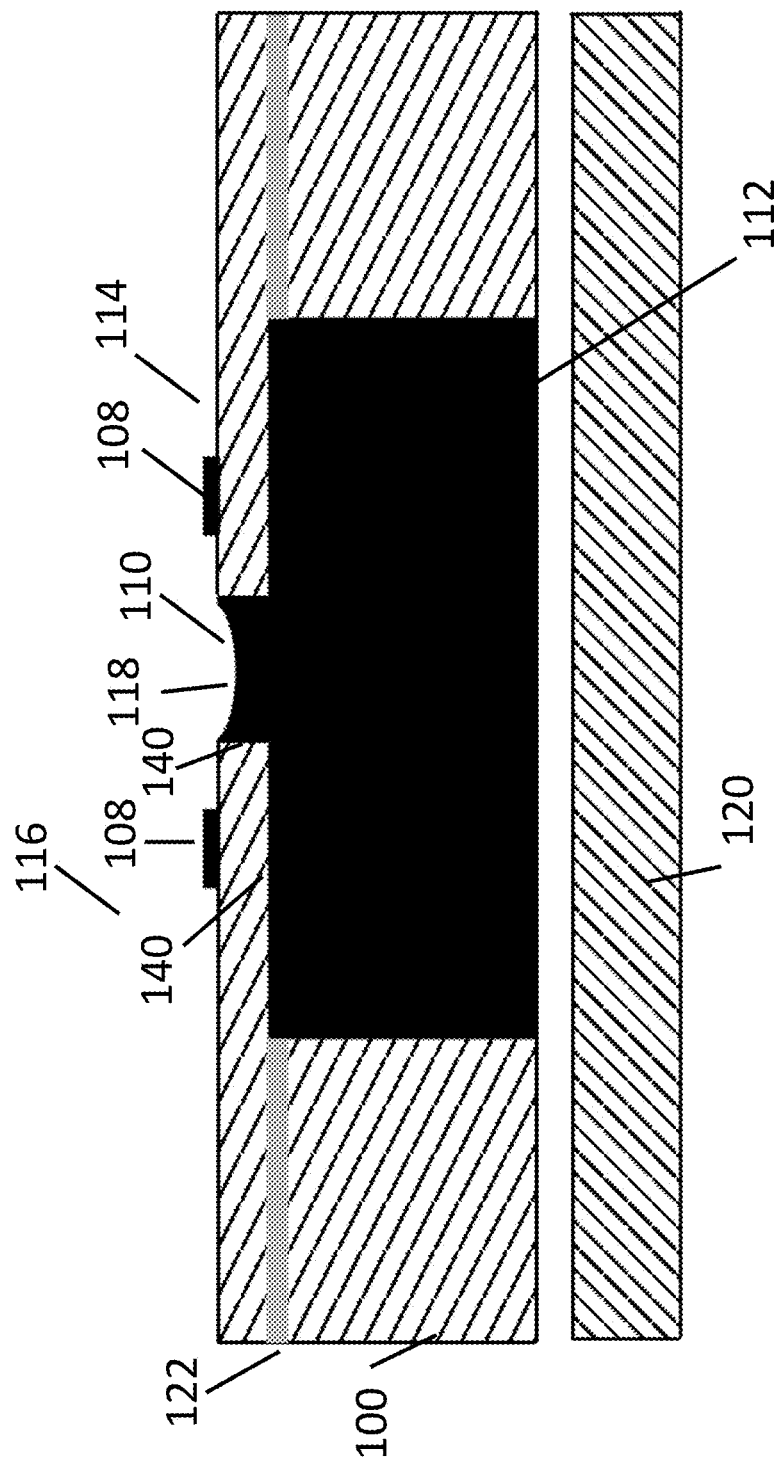

FIG. 4B depicts an illustrative embodiment where structure 100 is bound to thin structural region 114 with structural bond 122.

Figure 4C:
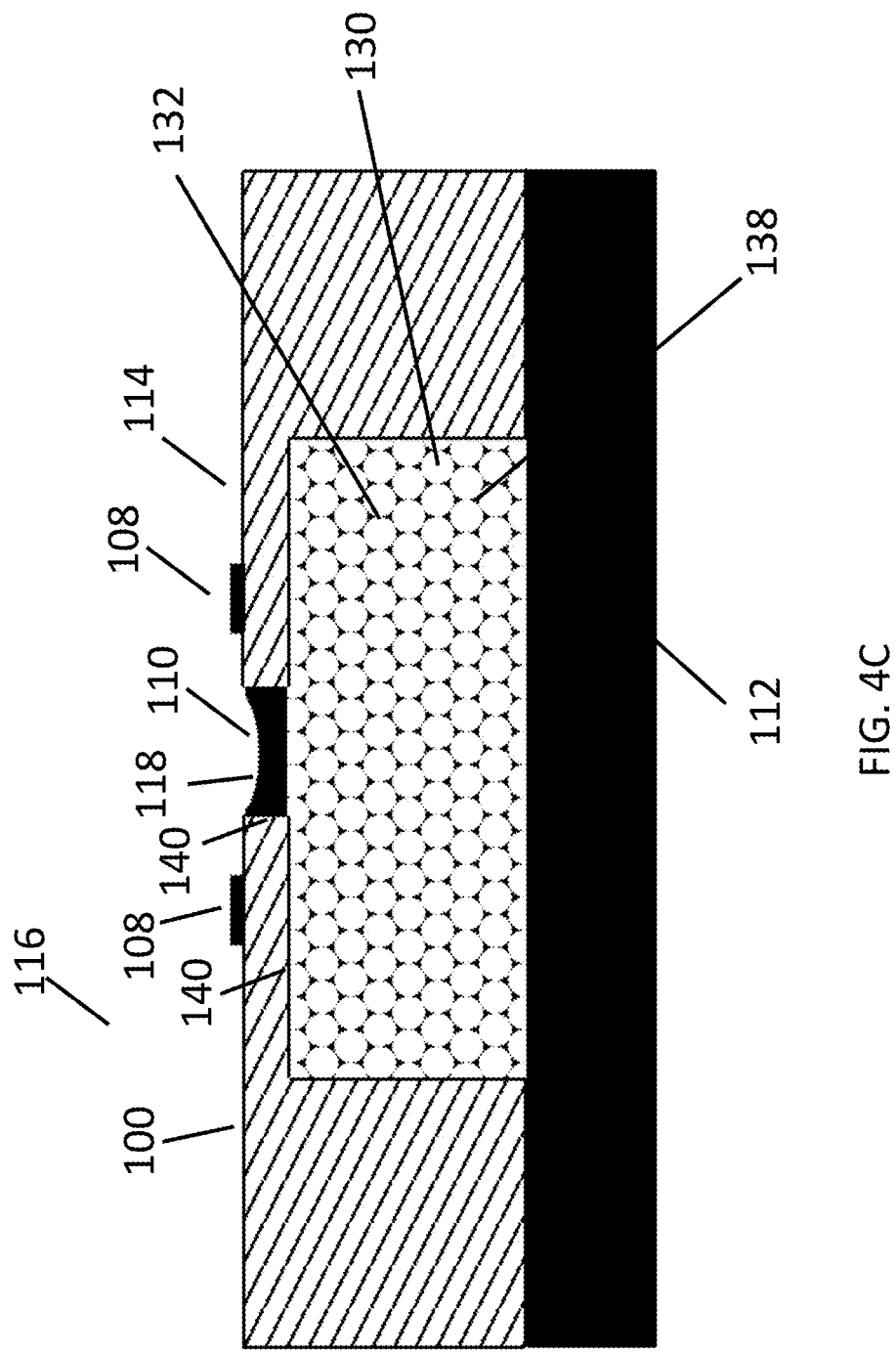

FIG. 4C shows a profile view of the apparatus depicting the various components of another illustrative embodiment. The surrounding environment 116 is above the structure. Vaporization ports 110 are formed in the structure 100 and are in fluid communication with the liquid source 112 and the surrounding environment 116. A heating element 108 is in thermal communication with the vaporization port 110 and located on a thin structural region 114. In an embodiment, particles or beads 130 form a wicking structure located in all or part of the liquid source region 112 and optionally located in the vaporization port 110 as well, and at least in the region adjacent to the vaporization port 110. In an embodiment, the particles or beads 130 may be hydrophilic. In an embodiment, the particles or beads 130 may be hydrophobic, or may be a hydrophilic/hydrophobic combination. In an embodiment, hydrophilic particles or beads 130 may be formed from glass or other materials. In an embodiment, the particles or beads 130 may be optionally sintered 132 or joined together by some other manner. In an embodiment, the particles or beads form small interstitial regions 138 that enhance the effect of the hydrophilic or hydrophobic surface properties of the beads or particles 130. In an embodiment, the particles or beads 130 could range in size from ten nanometers to 10 millimeters. In an embodiment, the particles or beads could range in size from 1 micrometer to 1 millimeter. In an embodiment, the particles or beads 130 could range in size from 10 micrometers to 300 micrometers.

Figure 5:
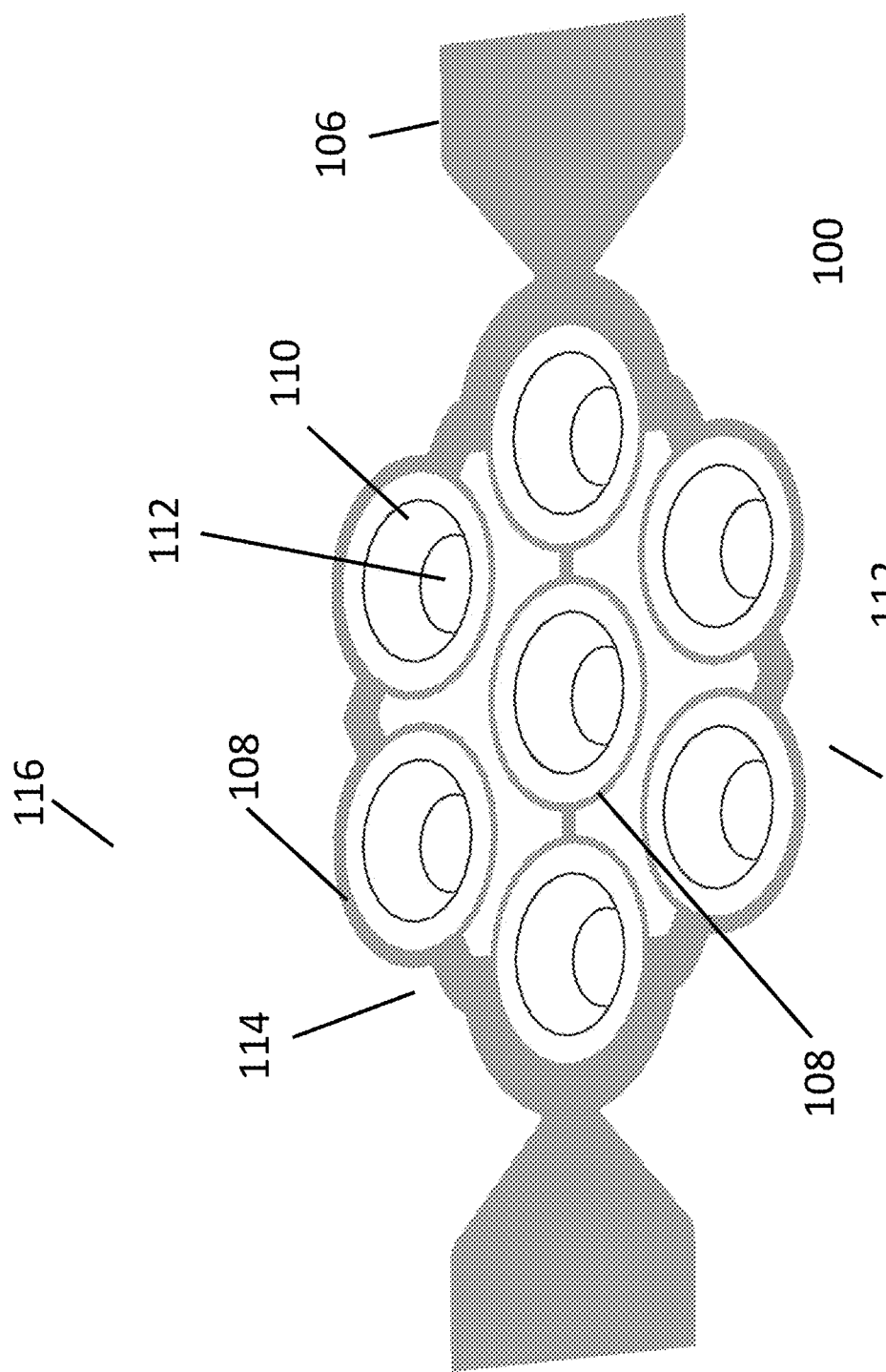
FIG. 5 shows a top view of the apparatus depicting some of the major components of an illustrative embodiment.

FIG. 5 shows a top view of the apparatus depicting some of the major components of an embodiment. Vaporization ports 110 are formed in the structure 100 and are in fluid communication with the liquid source region 112 and the surrounding environment 116. A heating element is in thermal communication with the vaporization port 110 and located on a thin structural region 114. In an embodiment, the heating element 108 is a thin film resistive heating element. In an embodiment the thin film heating element is configured into three parallel circuits, which further form a parallel circuit surrounding each vaporization port.

FIG. 5 shows a detailed view of an example embodiment where a single vaporization cluster 104, has a lateral dimension of approximately 900 um, contains seven vaporization ports 110, with lateral dimensions of 60 um-150 um, and heating elements 108 in thermal communication with the vaporization ports 110 such that heat produced by the heating elements 108 is transported to the region of the vaporization ports 110 which is in fluid communication with liquid source 112. In illustrative embodiments, the vaporization ports can range in size from 10 um to 300 um in lateral dimension, and in other embodiments range from 1 um to 1000 um. In illustrative embodiments the vaporization cluster could range in lateral dimensions from 10 um to 100 mm. In illustrative embodiments the vaporization cluster could range in lateral dimensions from 100 um to 10 mm The width of the heating elements 108 can be optionally configured with varying widths and thickness, or varying materials to produce a desired Joule heating profile. In some embodiments a desired heating profile may be chosen to provide uniform vaporization of a working fluid, while avoiding excessive heating from undesirable hot-spots. In some embodiments, 0.01 to 500 Watts of heat may be delivered to the fluid to produce vapor 102. In other embodiments, 1 to 50 Watts of heat may be delivered to the fluid to produce vapor 102.

In some illustrative embodiments, a hierarchy of resistive heating elements being connected in parallel (as depicted in FIG. 5) may have certain advantages. For example, the electrical resistance of metals can increase with increasing temperature. Therefore, if one element of a parallel circuit has a higher temperature than another element of the parallel circuit, that element could have a higher resistance and force more electrical current through the lower temperature element and thereby increase the Joule heating produced by the lower temperature element. In some embodiments, resistive heating elements connected in parallel could facilitate thermal regulation, which could help mitigate local thermal hot spots.

Figure 6A:
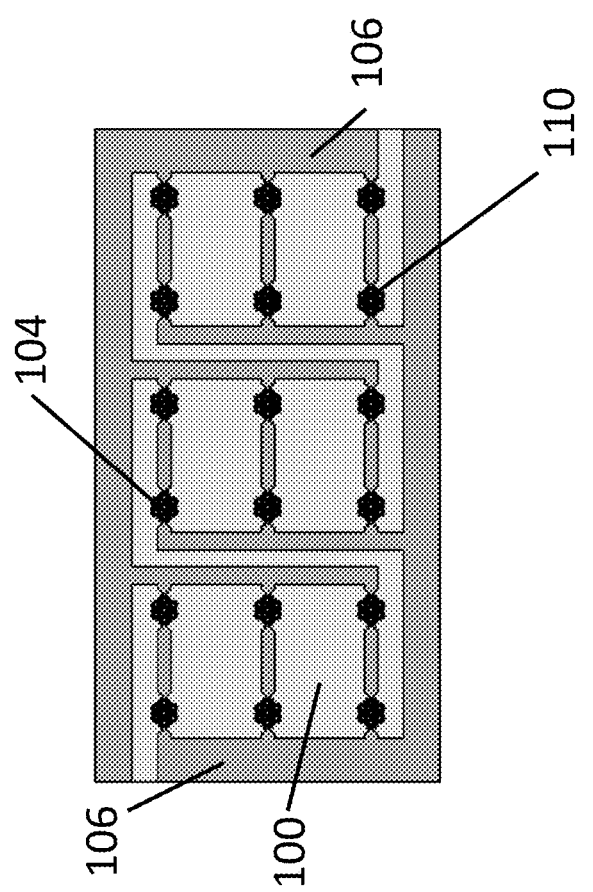
FIGS. 6A and 6B show a schematic of an exemplary microfluidic vaporization chip for an illustrative embodiment that contains 18 vaporization clusters
Figure 6B:
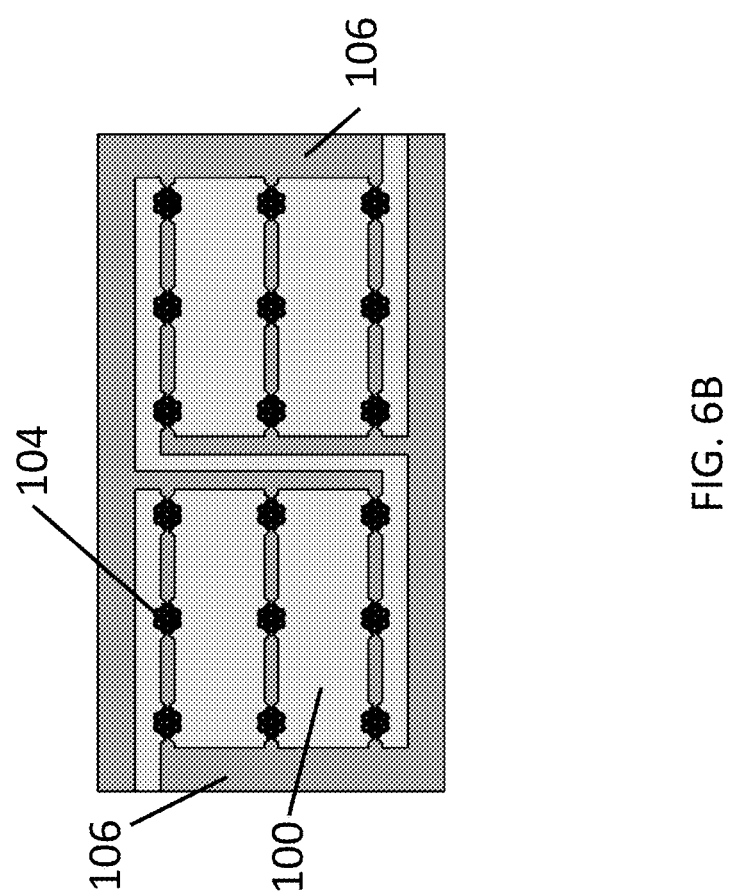

FIGS. 6A and 6B show an overview of a single microfluidic vaporization device structure 100. In an illustrative embodiment a single device structure 100 contains eighteen vaporization clusters 104 with each cluster 104 containing seven vaporization ports 110, for a total of 18×7=126 vaporization ports 110 for this example embodiment. In one example embodiment shown in FIG. 6A, two vaporization clusters 104 are connected by electrode leads 106 in series with nine parallel circuits. In another example embodiment shown in FIG. 6B, three vaporization clusters 104 are connected by electrode leads 106 in series with nine parallel circuits.

In other illustrative embodiments, the clusters could be connected in various series and/or parallel configurations, individually addressable, or other electrical wiring scheme. In an example embodiment, the microfluidic device structure 100 is 4 mm×10 mm in lateral dimension and 0.3 mm thick. In an example embodiment, the microfluidic chip is fabricated from glass, but for other embodiments, it could be fabricated from plastic, silicon, titanium, metals, ceramics, PDMS, polymers, fiberglass, composites, or other materials.

Joule heating from a resistive element can be described by $Q=V^2/R$, where Q is the Joule heating power, V is the voltage drop across the resistive element, and R is the electrical resistance of the element. As temperature increases, the electrical resistance of typical metals increases. If the voltage drop is constant, the amount of Joule heating will decrease with increasing temperature. Therefore, in an embodiment, it can be advantageous to have parallel circuits. If one branch of the parallel circuit has a higher temperature than another branch of the circuit, the branch with a higher temperature will have a higher resistance, and will therefore produce less Joule heating. In an embodiment with parallel resistive heaters, the various branches of the circuit may have self-regulating properties, that may help to regulate Joule heating that may help to maintain more uniform temperatures in comparison to the reduced uniformity which could occur using non-parallel circuit configurations.

In some embodiments, parallel resistive heaters could be configured with different resistance in each branch. In some embodiments, resistance of the heating elements could be modified by using different materials, different depths, different lengths, and/or different widths. In some embodiments, branches of parallel resistive heaters can have different resistances that could be optimized to produce desirable and well-controlled temperature distributions. In some embodiments, uniform temperature distributions may be desirable. In some embodiments, non-uniform temperature distributions may be desirable.

In some embodiments a hierarchical combination of parallel and resistive heating elements 108 can be judiciously chosen to provide desired heating profiles, and self-regulating heating elements.

Figure 7A:
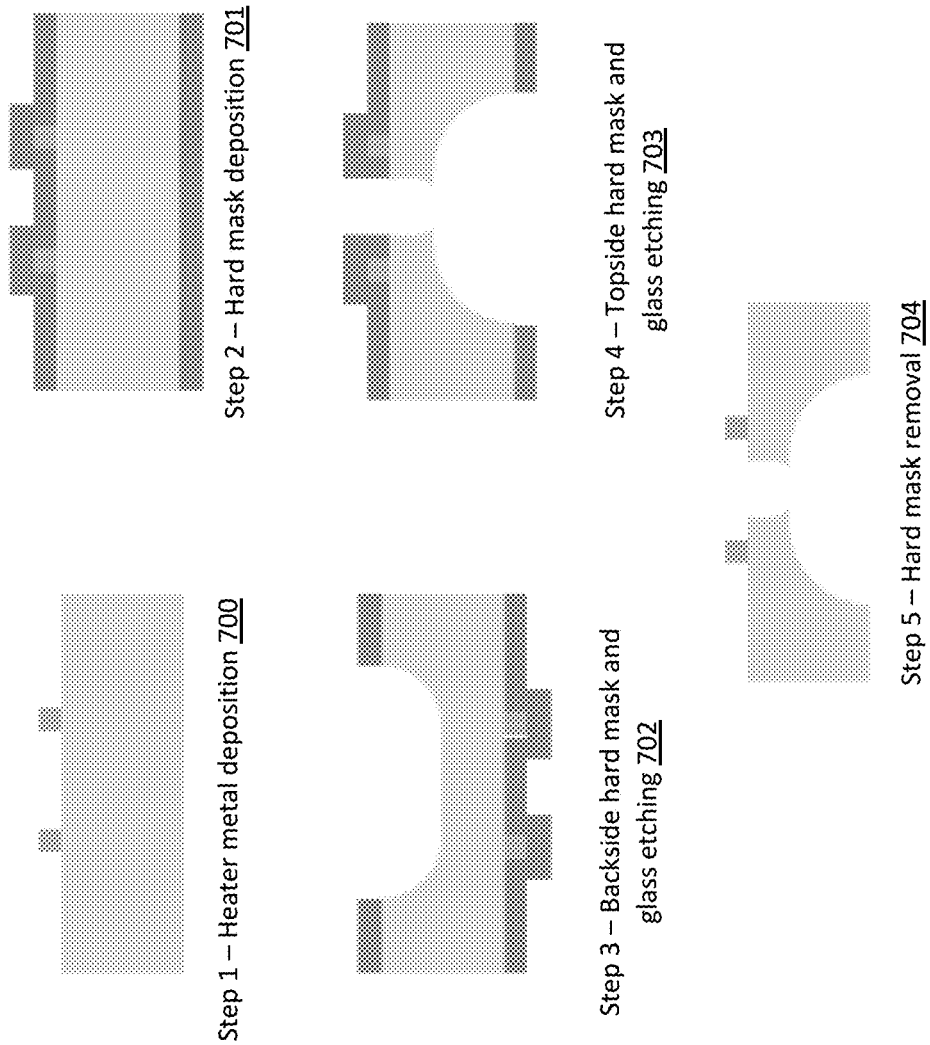
FIGS. 7A and 7B show examples of microfabrication process flows for device fabrication for an illustrative embodiment.

FIG. 7A shows an example for a microfabrication process flow for device fabrication for an embodiment, which consists of five processing steps using a single structure. In an illustrative embodiment, the structure 100 could be made from a 300 μm thick glass substrate from Schott (D263T-eco, AF32-eco or MEMpax). The glass substrate could be formed from a variety of materials and thicknesses ranging from 1 um to 10 mm. A photoresist could be patterned and metal (for example, titanium and platinum) could be deposited for the electrode leads and heating elements (Step 1—Heater metal deposition 700). After photoresist and metal liftoff, a hard mask film (for example, chromium/gold, aluminum or amorphous silicon) could be deposited on both sides of the substrate (Step 2—Hard mask deposition 701). On the backside, photoresist could be patterned and the hard mask could be etched (wet or dry) followed by the glass being optionally wet-etched down to roughly half the substrate thickness (Step 3—Backside hard mask and glass etching 702). On the frontside, the vaporization port 110 could be patterned in close proximity (which could range between 5 um to 100 um, or 0.5 um to 1 mm) to the heater element 108 and a hard mask could be etched, followed by optional wet etching of the glass. At the same time, the backside could optionally be further etched since it could optionally be exposed, and a via (or through hole) could be created (Step 4—Topside hard mask and glass etching 703). This could allow the vaporization port 110 to be in fluid communication with the liquid source 112 and the surrounding environment 116. Finally, the hard mask could be removed from both sides, and the substrate could then be diced (Step 5—Hard mask removal 704).

A variety of nanofabrication and microfabrication equipment could be used to fabricate some embodiments of the vaporization device. The fabrication may include numerous deposition tools such as electron beam deposition, which could be used for the heating element, and plasma enhanced chemical vapor deposition (PECVD), which could be used to deposit the hard masks. In some embodiments, wet chemistry benches could be used for a variety of etch chemistries, including hydrofluoric acid etching of glass. Dry etching could also be used for isotropic etches in certain materials such as inductively coupled plasma reactive ion etching (ICP-RIE). Furthermore, in some embodiments, a photolithography mask aligner capable of backside alignment, such as the SUSS MA-6, could be used to pattern and align the features from front to back.

Figure 7B:
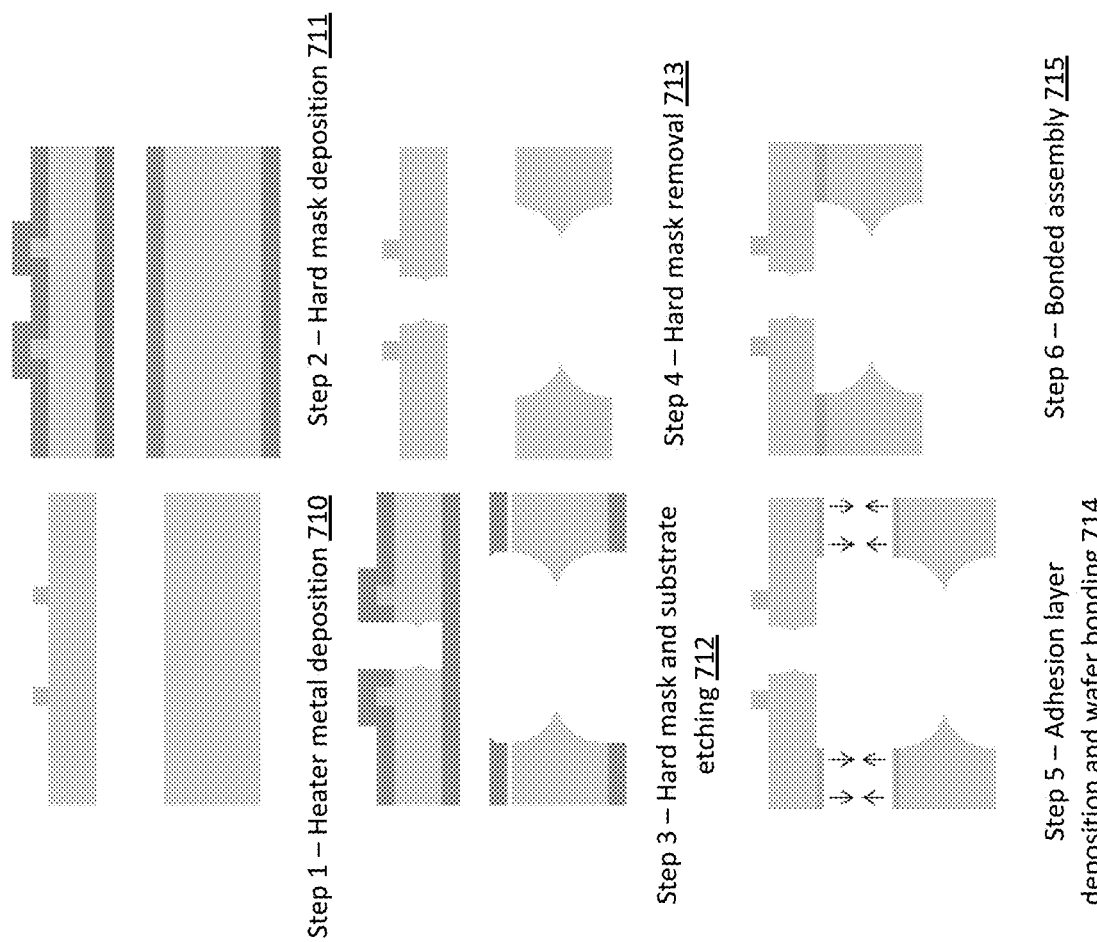

FIG. 7B shows an illustrative for a microfabrication process flow for device fabrication for an illustrative embodiment shown FIG. 4B, which includes six processing steps using structural element 100 and thin structural region 114 (i.e. two initially separate structures). This embodiment could be extended to two or more (i.e. multiple) structures, which could be bonded with structural bond 122 (shown in FIG. 4B) using one or more bonding techniques.

The fabrication process could use 100 um, 300 um, or even 500 um thick glass substrates to form structure 100. Embodiments could use 1 um to 10 mm thick substrates for thin structural region 114 (shown in FIG. 4B), and the substrates could encompass a variety of materials, such as glass, titanium, aluminum, sapphire, silicon carbide, diamond, ceramics, metals, silicon, and the like.

Two different thicknesses of substrates could be used. For example, one substrate could be 100 um (i.e. a relatively thin) substrate and another substrate could be 300 um (i.e. a relatively thick) substrate, which could allow for significantly flexibility in feature sizes during optional wet etch processes. Referring to FIG. 7B, a 100 um thick substrate could be patterned with photoresist and metal could be deposited for the heating element (Step 1—Heater metal deposition 710). An additional metal deposition step could be optionally used for the electrode leads. For example, in an embodiment, gold contacts could be optionally patterned at the chip connections.

In one embodiment, after photoresist and metal liftoff, a hard mask film could be deposited on both sides of the thin substrate (Step 2—Hard mask deposition 711) and the thick substrate. Photoresist could be patterned on both sides of the substrates to expose regions adjacent to the heating element on the thin substrate and the thick substrate. The hard masks could be etched, followed by the substrates being etched down to half the thickness of the substrates on each side, creating a through hole (i.e. a via through the chip) (Step 3—Hard mask and substrate etching 712), which could provide fluid communication for the vaporization port 110 with the liquid source 112 and fluid communication with the surrounding environment 116.

In this embodiment, the hard mask could then be removed from both sides of the substrates (Step 4—Hard mask removal 713). Depending on the bonding technique, an adhesion layer could optionally be deposited either on the back side of the thin substrate, the top side of the thick substrate, both, or neither. Furthermore, in some embodiments, appropriate cleaning and surface preparation could be applied to the two substrates and they could be bonded together using a variety of well-known bonding techniques (Step 5—Adhesion layer deposition and wafer bonding 714). In some embodiments, the bonded assembly could then be diced into smaller individual units (Step 6—Bonded assembly 715).

Figure 8:
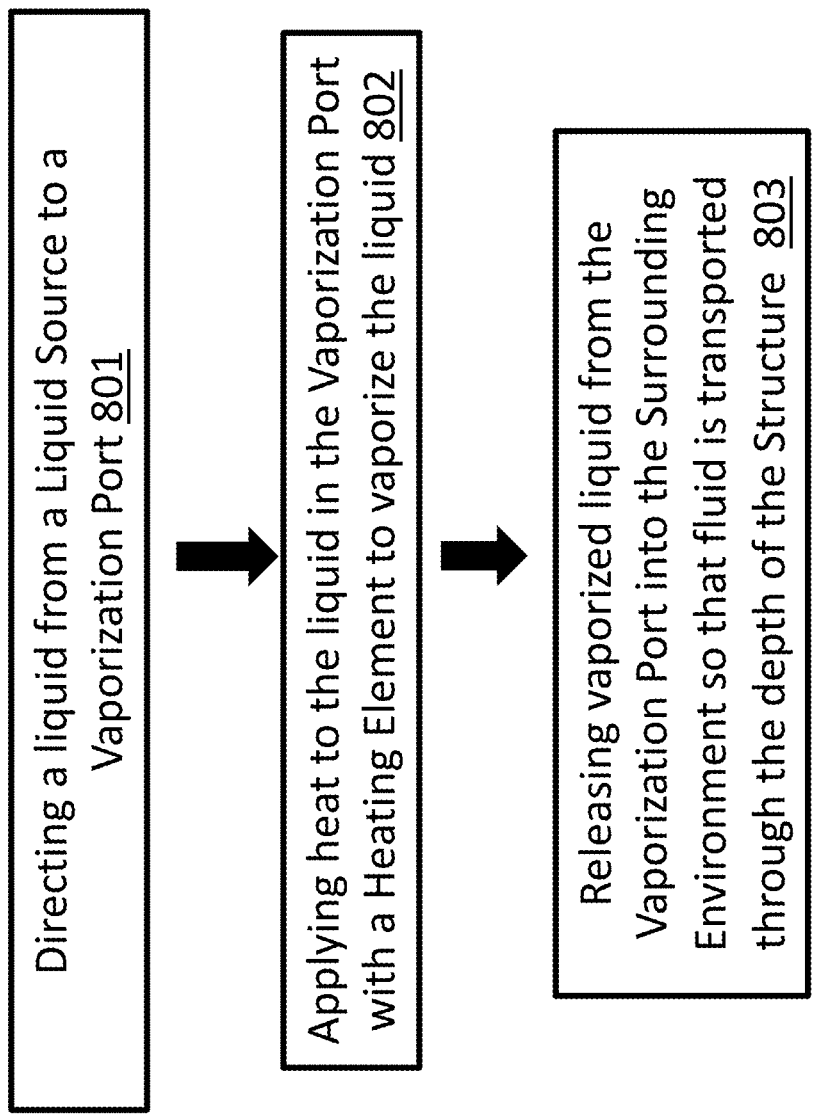
FIG. 8 shows a flowchart depicting a method of an illustrative embodiment.

FIG. 8 shows a flowchart depicting a method of an embodiment, which involves directing a liquid from a liquid source to a vaporization port 801, and applying heat to the liquid in the vaporization port with a heating element located in close proximity to the vaporization port to vaporize the liquid 802 (which could range between 5 um to 100 um, or 0.5 um to 1 mm). In an embodiment, the vaporized liquid is released from the vaporization port into the surrounding environment so that fluid is transported through the depth of the structure 803. In some embodiments, the vaporization port has lateral dimensions ranging from 10 um-300 um. In yet other embodiments, the vaporization port has lateral dimensions ranging from 1 um-1000 um. Liquid could be introduced to the liquid source by directly placing the liquid in the liquid source or by an optional pump or an optional wicking structure wherein the liquid could be transported through capillary action to the liquid source. In an embodiment, electrical energy could be applied to the heating element, and the heating element could be heated through Joule heating (i.e. resistive heating). The thermal energy from the heating element could then be transferred to the thin structural region, which is adjacent to the vaporization port and liquid source. Heat could then be conducted locally into the liquid to heat the liquid to an optimal temperature for vaporization. This temperature could be well controlled so that the liquid is heated sufficiently for vaporization, but does not reach an undesirably high temperature, which could cause undesirable chemical reactions or dryout the vaporization port. In addition, by controlling the electrical energy to the heating elements, the rate of vaporization or the total mass of vaporization can be accurately controlled. In some embodiments, the amount of electrical energy could be optionally varied, and optimized for the specific application. In yet other embodiments, an electrical waveform could be sinusoidal, square wave, or other waveform, which could be optimized for the specific application. In yet other embodiments, the waveform could pulse and cause vaporization, an aerosol or ejections of liquid droplets, and could decrease parasitic heat loss, thereby increasing thermodynamic efficiency.

Figure 9:
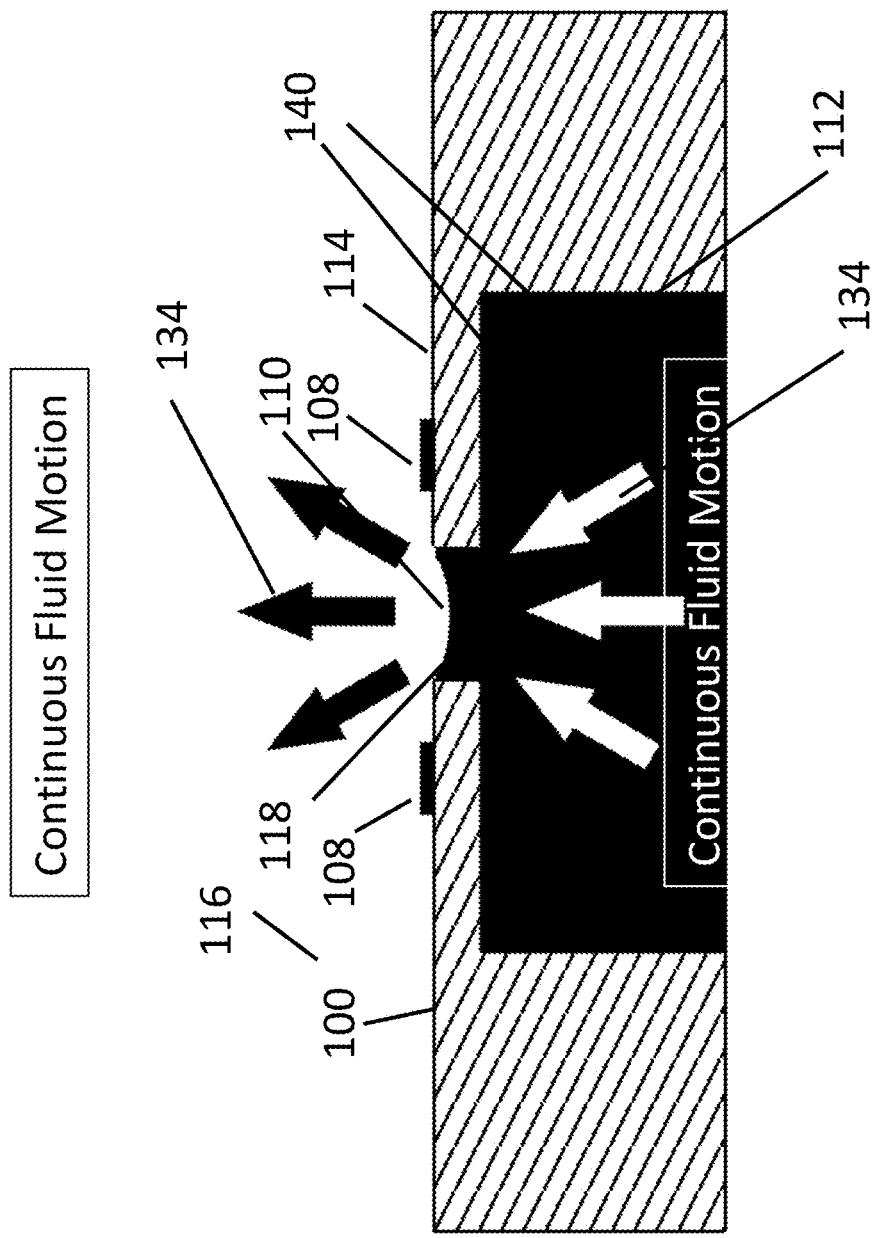
FIG. 9 shows a profile view of the apparatus depicting the major components of an illustrative embodiment.

FIG. 9 refers to an illustrative embodiment where the liquid flows from the liquid source 112 region into the vaporization port 110 and is then vaporized through the meniscus 118 into the surrounding environment 116. In some embodiments, the liquid may be transported from one side (say the backside) of the microfluidic device structure 100, vaporized through meniscus 118 and vapor released from the other side (say the front side) of the microfluidic device structure 100, such that fluid is transported through the depth of the structure (i.e. though a via or through-hole). In these embodiments, the ability for liquid to travel through the device is made possible because the vaporization port 110 is in fluid communication with the liquid source 112 and the surrounding environment 116. Arrows 134 represent continuous fluid motion from one side of the structure to the other side of the structure. White arrows 134 depict continuous fluid motion of the liquid through the liquid source 112 to vaporization port 110. Black arrows 134 depict continuous fluid motion of the vapor from vaporization port 110 to surrounding environment 116. The ability for fluid to be transported through the depth of the structure can make the vaporization process much more energy efficient. In some embodiments, the ability for fluid to be transported through the depth of the structure can reduce or even prevent dryout, and provide for continuous fluid motion. In some embodiments, this may allow, for example, the heating element 108 be placed in close proximity to vaporization port 110 for desirable thermal communication (e.g. to within 0.5 microns to 1000 microns, or 5 microns to 100 microns) to the meniscus 118, where the phase change occurs. This can dramatically reduce the distance heat must be transferred into the liquid during vaporization, and can allow the heating element 108 to operate at a lower temperature, compared to other vaporizer devices. This can be especially critical because most liquids have low thermal conductivity (for example the thermal conductivity of water is approximately $k_w$=0.58 W/(m K) at room temperature, the thermal conductivity of glycerin is approximately $k_w$=0.29 W/(m K)). The efficient design of these embodiments can also reduce the maximum temperature that the liquid must be exposed to during vaporization. Furthermore, in some embodiments, the more efficient design where the liquid flows through the microfluidic device may significantly reduce dryout of the liquid in the vaporization port 110, providing consistent and superior performance.

FIG. 9 refers to an illustrative embodiment where there is significant contact surface area 140 between the thin structural region 114 and the liquid contained in the vaporization port 110 and the liquid source region 112. Since liquids can have low thermal conductivity, it is important to have a large contact area 140 so that heat can be readily transferred from the thin structural region 114 to the liquid. In some embodiments, the thin structural region 114 may decrease the distance wherein heat may be transferred from the heating element 108 through the thin structural region 114, before reaching the contact area 140 between the thin structural region 114 and the liquid in the liquid source region 112 and vaporization port 110. In some embodiments, having a minimal distance wherein heat is transferred through the thin structural region 114 may be important, because glass has a low thermal conductivity of approximately, $k_g$=1.05 W/(m K). Other materials such as metals, silicon, and the like provide a larger thermal conductivity, for example the thermal conductivity of silicon is approximately $k_{Si}$=130 W/(m K). However, in many embodiments, for thermodynamic efficiency, it is important to keep the thermal energy focused in close proximity to the vaporization ports, and therefore minimize the amount of heat that is transferred to the bulk substrate and surrounding environment. In some embodiments, the thermal energy is substantially confined to vaporization cluster 104. In some embodiments, vaporization cluster 104 can be nominally 1 mm in size. In some embodiments, vaporization cluster 104 can range in size from 100 um to 10 mm. In some embodiments, vaporization cluster 104 can range in size from 10 um to 100 mm. In many of these embodiments, it may be advantageous to use a low thermal conductivity material, such as, but not limited to, a glass, a plastic, a polymer, a fiberglass, a composite, or a ceramic, and the like. In many of these embodiments, the thin structural region 114, combined with a low thermal conductivity material may help to minimize parasitic heat transfer losses to the bulk structure 100 and surrounding environment 116. In yet other embodiments, using an optimized electrical waveform may help to reduce parasitic heat transfer losses to the bulk structure 100 and the surrounding environment 116.

In some embodiments, glass has many features that could make it a suitable structural material for a vaporization device. For example, glass could be made durable, could be available in many geometric forms including thin wafers, could be machined, could be custom blown, shaped or molded, could be widely and commercially available, could be purchased at an affordable price, could be wet etched, could have a low electrical conductivity, could have a low thermal conductivity, could be made hydrophilic with appropriate cleaning processes, could be made hydrophobic with a judiciously chosen surface coating, surfaces could be treated with well-known surface chemistries, could be chemically inert, could be aggressively stripped of organic materials using a Piranha solution, could be mechanically stable below the glass transition temperature, metal could be deposited for electrode leads and heating elements, or could be bonded to itself or to other materials.

In some embodiments, glass could be chosen as a structural material for environmental, toxicity or health reasons. In some embodiments, the electrode leads 116 and the heating elements 108 could be formed from deposition of platinum and titanium. Many other materials could be used for electrode and heating element deposition, such as carbon, gold, silver, nickel, aluminum, and many others. In some embodiments, platinum may be used as electrode leads and resistive heating elements (through Joule heating), and may also be used as Resistive Thermal Devices (RTDs) for measurement of the approximate temperature of the heating elements. The electrical resistance of platinum and many other metals and other materials is a function of temperature, and could be used to determine the approximate temperature of the heating element. In some embodiments, an electrical control circuit could be used for feedback control of vaporization devices, to maintain a constant operating temperature or constant operating power setting, or a temporal profile of operating temperature or operating power, or some arbitrary operating temporal profile that could be tailored for a specific application. Other metals and other materials could be used as RTDs for vaporization devices. However, in some embodiments platinum could be a suitable material. In these embodiments, titanium could be a suitable adhesion material to provide adhesion between a glass substrate and a platinum or other metal deposited film. Other adhesion materials could also be used.

In some embodiments, the heating elements 108 in combination with continuous fluid motion provides steady and uniform heating of the fluid, which may keep the fluid from obtaining an undesirably high temperature, which could cause undesirable chemical by-products, or could combust, partially combust, or otherwise burn scorch, or char the liquid and the microfluidic structure 100. In some embodiments, the continuous fluid motion may provide for a steady operation that may allow the apparatus to continuously function for indefinite periods of time, while minimizing potentially undesirable ramifications, such as liquid dryout, undesirable chemical by-products, scorching or combusting of the liquid, or scorching or combusting of the apparatus.

The desired operating temperature of the vaporizer can vary significantly depending upon the material to be vaporized, the desired mass flux to be vaporized, the operating conditions, and many other factors. In some embodiments, the apparatus is designed to operate in temperatures ranging from 180° C.-250° C. In some embodiments, the apparatus is designed to operate in temperatures ranging from 200° C.-350° C. In some embodiments, the apparatus is designed to operate in temperatures ranging from 300° C.-450° C. In some embodiments, the apparatus is designed to operate in temperatures ranging from 20° C.-200° C. In some embodiments, the apparatus is designed to operate in temperatures ranging from 20° C.-450° C. The range of temperatures is by way of example, other ranges are possible as well.

In some embodiments, vaporization could occur in discrete time periods ranging from a few milliseconds to tens of seconds, or longer. In some embodiments, vaporization could occur in discrete time periods ranging from a few milliseconds to tens of seconds, or longer, to provide precision delivery of vapor mass for accurate dosing.

Figure 10:
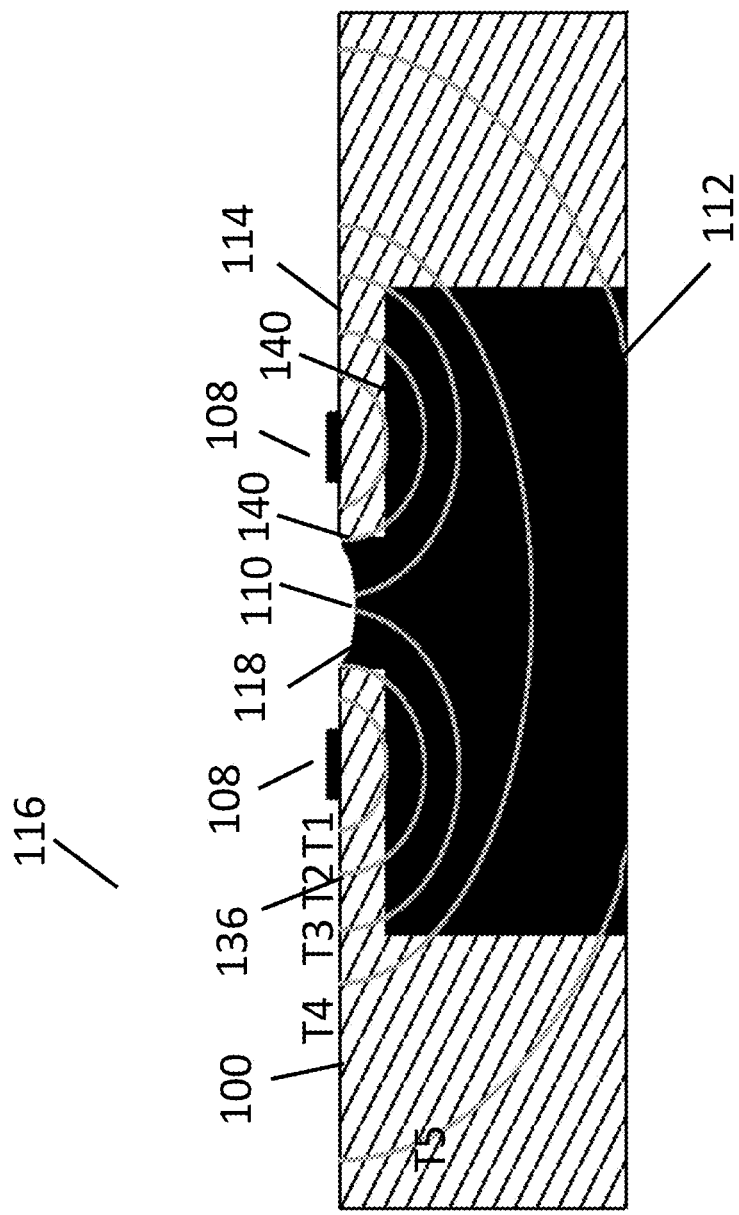
FIG. 10 shows a profile view of the apparatus depicting the major components of an illustrative embodiment.

FIG. 10 shows a profile view of the apparatus depicting the various components of an illustrative embodiment. The surrounding environment 116 is above the structure 100. Vaporization ports 110 are formed in the structure 100 and are in fluid communication with the liquid source region 112 and the surrounding environment 116. A heating element 108 is in thermal communication with the vaporization port 110 and located on a thin structural region 114. The white lines 136 depict contours on constant temperature. In some embodiments, the thin structural region 114 helps to confine thermal energy substantially to within vaporization cluster 104, and to within close proximity of the heating elements 108 and the vaporization ports 110, and thereby reduces thermal losses to the bulk structure 100.

In some embodiments, there is significant contact surface area 140 between the thin structural region 114 and the liquid contained in a vaporization port 110 and the liquid source 112. Since liquids can have low thermal conductivity, it is important to have a large contact area 140 so that heat can be readily transferred from the thin structural region 114 to the liquid. In some embodiments, the thin structural region 114 may decrease the distance wherein heat may be transferred from the heating element 108 through the thin structural region 114, before reaching the contact area 140 between the thin structural region 114 and the liquid in the liquid source region 112 and vaporization port 110. In some embodiments, having a minimal distance wherein heat is transferred through the thin structural region 114 may be desirable, because glass has a low thermal conductivity of approximately, $k_g$=1.05 W/(m K). Other materials such as metals, silicon, and the like provide a larger thermal conductivity, for example the thermal conductivity of silicon is approximately $k_{Si}$=130 W/(m K). However, in many embodiments, for thermodynamic efficiency, it is important to keep the thermal energy focused substantially to within vaporization cluster 104 and within close proximity to the vaporization ports 110, and therefore minimize the amount of heat that is transferred to the bulk substrate 100 and surrounding environment 116. In many of these embodiments, it may be advantageous to use a low thermal conductivity material, such as a glass, a plastic, a polymer, a fiberglass, a composite, or a ceramic, and the like. In many of these embodiments, the thin structural region 114, combined with a low thermal conductivity material may help to minimize parasitic heat transfer losses to the bulk substrate 100 and surrounding environment 116. In yet other embodiments, using an optimized electrical waveform may help to reduce parasitic heat transfer losses to the bulk substrate 100 and the surrounding environment 116.

Figure 11A:
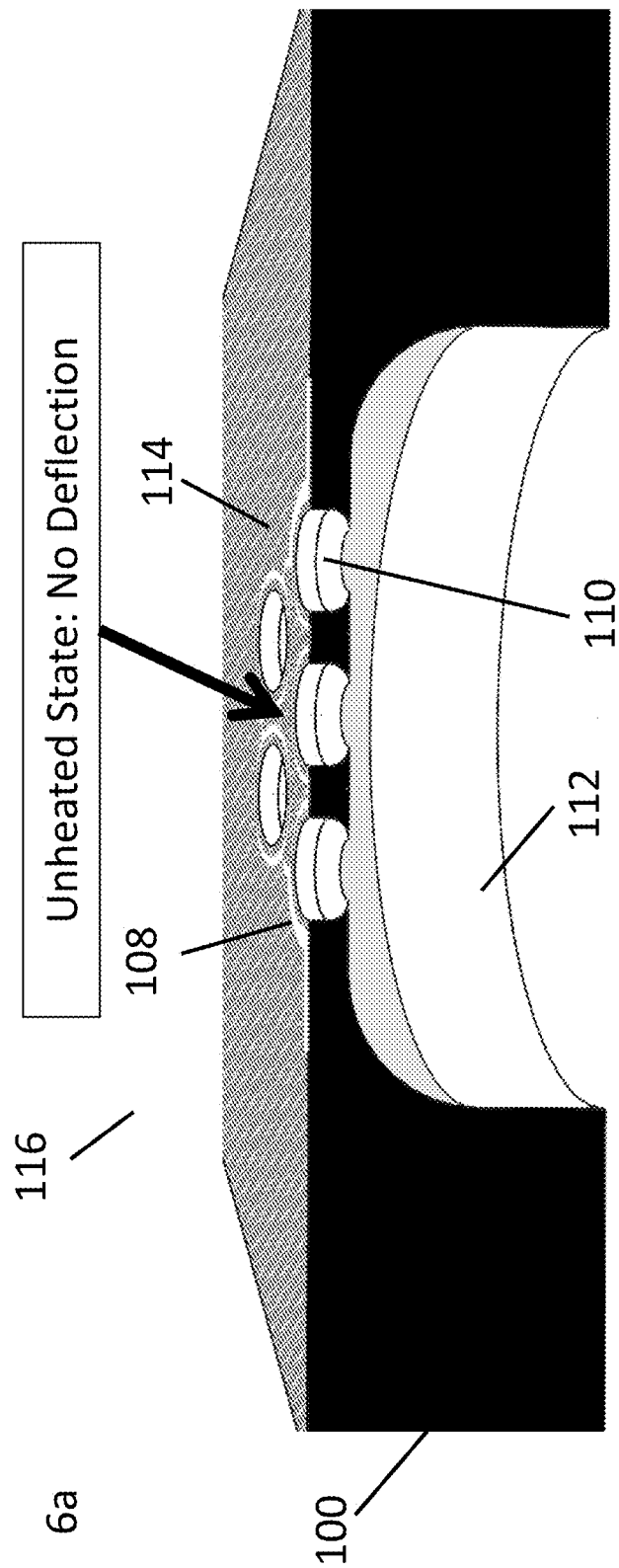
FIGS. 11A and 11B show cross section views of the apparatus depicting the major components of an illustrative embodiment.
Figure 11B:
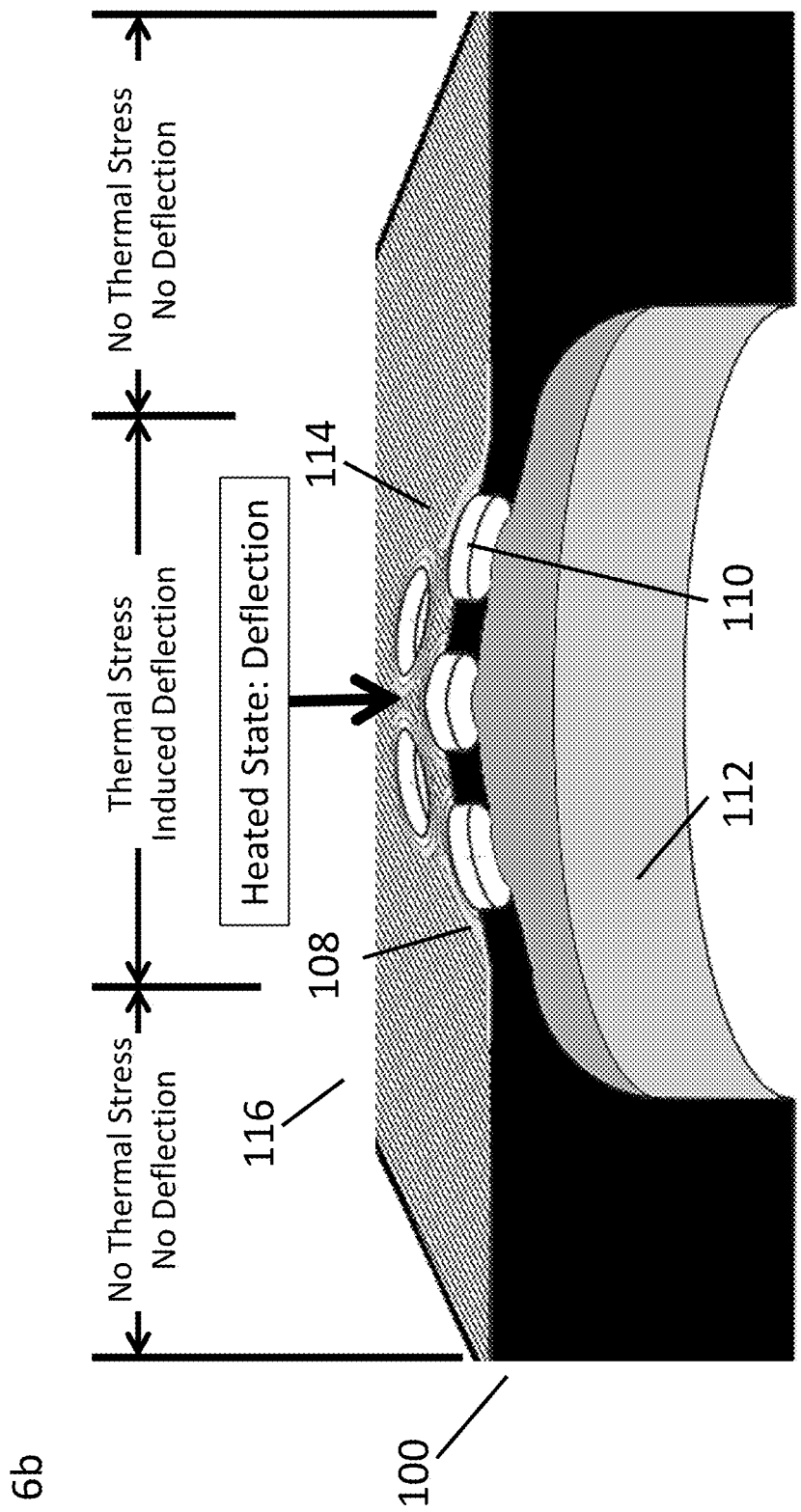

FIGS. 11A and 11B shows a profile view of the apparatus depicting the various components of an illustrative embodiment. The surrounding environment 116 is above the structure 100. Vaporization ports 110 are formed in the structure 100 and are in fluid communication with the liquid source region 112 and the surrounding environment 116. Heating elements 108 are in thermal communication with the vaporization ports 110 and located on a thin structural region 114.

FIG. 11A shows an illustrative embodiment where the thin structural region 114 is in an un-deflected state, which may occur when the apparatus is not being energized. In an embodiment, the heating elements 108 may be energized and produce thermal energy, which could increase the temperature in the proximity of the heating elements 108. The thin structural region 114 in proximity to the heating elements 108 could thermally expand due to an increase in temperature, which could cause thermal stress and/or thermal strain in the thin structural region 114 and in the resistive heating elements 108. In some embodiments, it is desirable for the principal stress to be less than 10-20 MPa. In some embodiments, it is desirable for the principal stress to be less than 70 MPa.

FIG. 11B shows an illustrative embodiment, where a thin structural region 114 is deflected due the thermal expansion, when the heating elements 108 are energized. In an illustrative embodiment, the thin structural region 114, may help confirm the thermal energy to the proximity of the heating element 108, which could help minimize thermal expansion of the bulk structure, and could help to reduce thermal stress and strain in the thin structural region 114. In some embodiments, it is desirable for the principal stress to be less than 10-20 MPa. In some embodiments, it is desirable for the principal stress to be less than 70 MPa.

In an embodiment, the thin structural region 114 could allow for thermal deflection, and could help reduce thermal stress. The mechanical stiffness of a structural beam is proportional to $h^3$, where h is the thickness of the structural beam. In some embodiments, the optionally thin structural region 114, may be sufficiently thin that it could have a relatively low mechanical stiffness, which could allow the thin structural region 114 to deflect with sufficiently low stress, when the heating elements 108 are electrically energized. In some embodiments, it is desirable for the principal stress to be less than 10-20 MPa. In some embodiments, it is desirable for the principal stress to be less than 70 MPa.

In an embodiment, the heating elements 108 could be comprised of metal that has a high coefficient of the thermal expansion, compared to the structural material. The thin structural region 114 may deflect as shown in FIG. 11B, and produce stain on the top surface that could be well-matched to the thermally-induced strain of the heating element 108 material, and thereby could dramatically reduce the stress between heating elements 108 and the thin structural region 114. In some embodiments, it is desirable for the principal stress to be less than 10-20 MPa. In some embodiments, it is desirable for the principal stress to be less than 70 MPa.

FIG. 12 shows a profile view of the apparatus depicting the various components of another illustrative embodiment. In this embodiment, an optional seal 124 could be located between the liquid in the vaporization port 110 and the surrounding environment 116. The seal 124 could be made of a thermally-responsive wax. This could provide a seal to enclose the liquid during storage, and then the optional seal 124 could be vaporized to activate the vaporization apparatus. The optional seal 124 could be used to extend shelf life before the first use, or extend storage life between uses. In some embodiments, the sealing material could be incorporated into the liquid to provide a self-sealing mechanism between uses, or between vaporization processes. The optional seal 124 could be manufactured from many different materials, beyond the exemplary case of wax. In some embodiments, the seal 124 could be comprised of a suitable sealing material which is solid at room temperature but melts, sublimes, recedes, or is cleared from the vaporization port 110 when the vaporizer is active. In some embodiments, the liquid source region 112 could contain a liquid which is a low volatility liquid and the optional seal may not be necessary or may not be desirable. In some embodiments, the surrounding environment 116 could be above the structure. A vaporization port 110 formed in the structure 100 could be in fluid communication with the liquid source region 112, but could be optionally separated from the surrounding environment by the optional seal 124. A heating element 108 could be in close proximity to the vaporization port 110 and located on the thin structural region 114. In some embodiments, heating element 108 is located within 0.5 um-1000 um of vaporization port 110. In some embodiments, heating element 108 is located within 5 um-100 um of vaporization port 110. In some embodiments, the optional seal 124 could be vaporized and allow the liquid in the vaporization port 110 to be in fluid communication with the surrounding environment 116. An optional bulk heater or cooler 120 could be located below the structure 100. This could provide heat that could cause an otherwise solid phase substance to become a liquid, or it could increase the temperature of the bulk liquid so that less thermal energy is required by the heating elements 108. An optional bulk heater or cooler 120 could increase or decrease the bulk temperature of the bulk liquid, and thereby could control the volatility of the liquid before it may undergo vaporization in the vaporization port 110.

Figure 13:
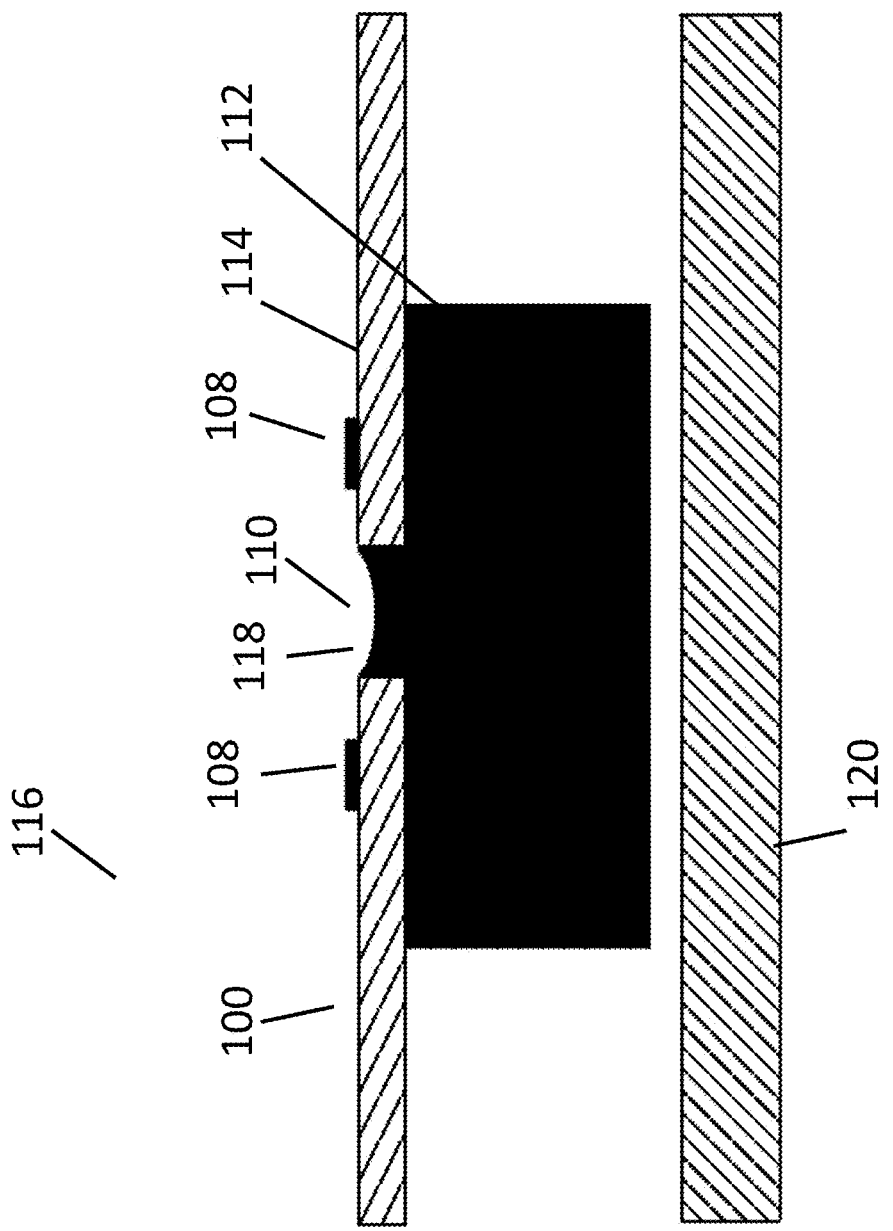
FIG. 13 depicts an illustrative embodiment that has an optional bulk heater or cooler that is shown below the structure.

FIG. 13 shows a schematic of another embodiment where the liquid source region 112 is adjacent to a thin structural region 114. The surrounding environment 116 is above the thin structural region 114. A vaporization port 110 is formed in the structure 100 and is in fluid communication with the liquid source 112 and the surrounding environment 116. A heating element 108 is in thermal communication with the vaporization port 110 and located on a thin structural region 114. An optional bulk heater or cooler 120 is shown below the structure 100.

Figure 14A:
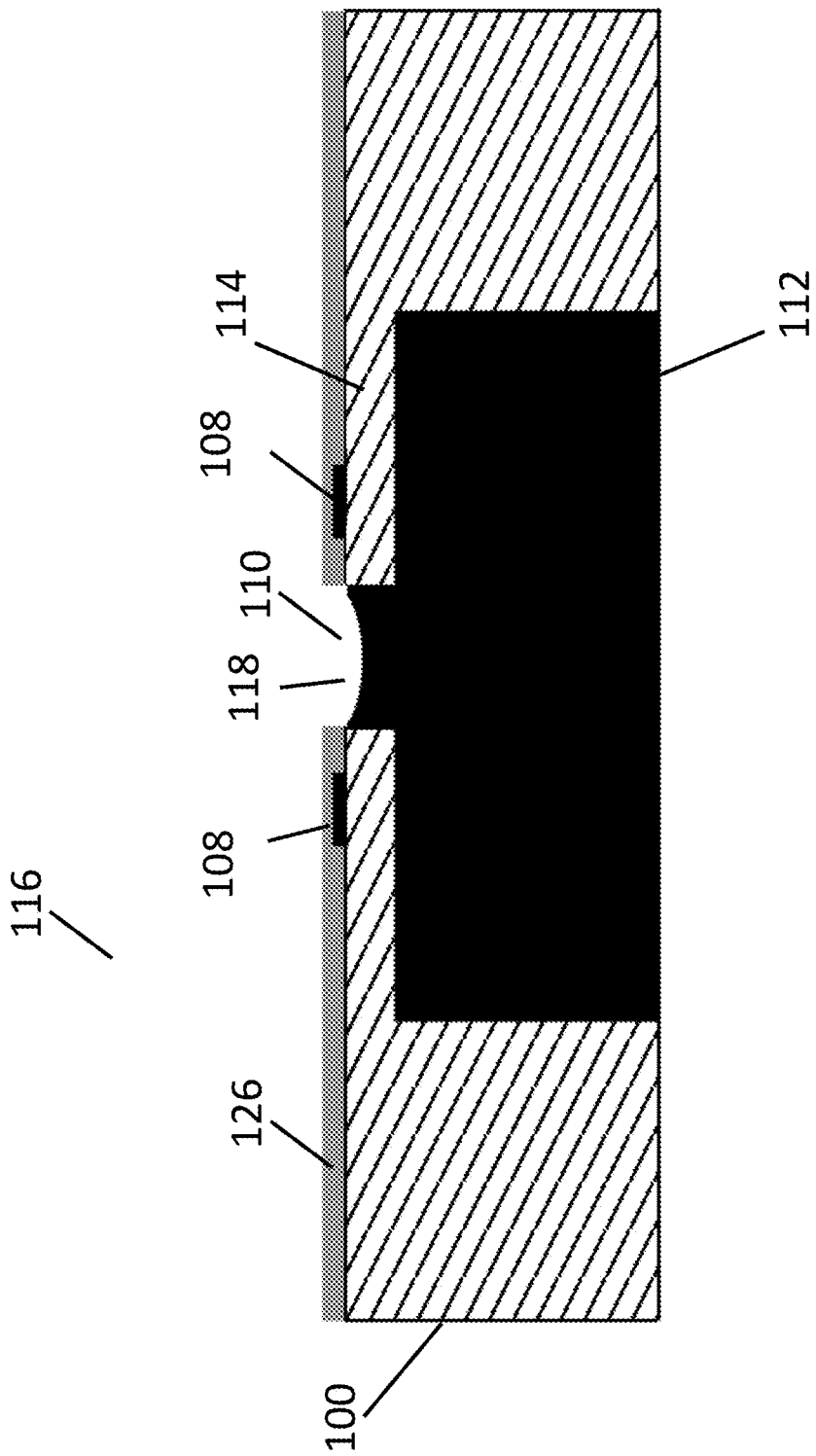

FIG. 14A shows an illustrative embodiment, where an optional protective layer 126 surrounds the heating element 108. The protective layer 126 could be deposited silicon dioxide, amorphous silicon, silicon nitride, alumina or other material. In some embodiments, the protective layer 126 can protect the heating elements 108 from becoming delaminated, due to differences in thermal expansion between the heating element 108 material and the underlying structural 100 material. In some embodiments, the protective layer 126 can serve as a chemical and/or electrical barrier between the heating element 108 and the surrounding environment 116. In some embodiments, the protective layer 126 is located in close proximity to the heating element 108. In some embodiments, the protective layer 126 is located within 0.5 um to 1 mm of the heating element 108. In some embodiments, the protective layer 126 substantially covers the structure 100.

Figure 14B:
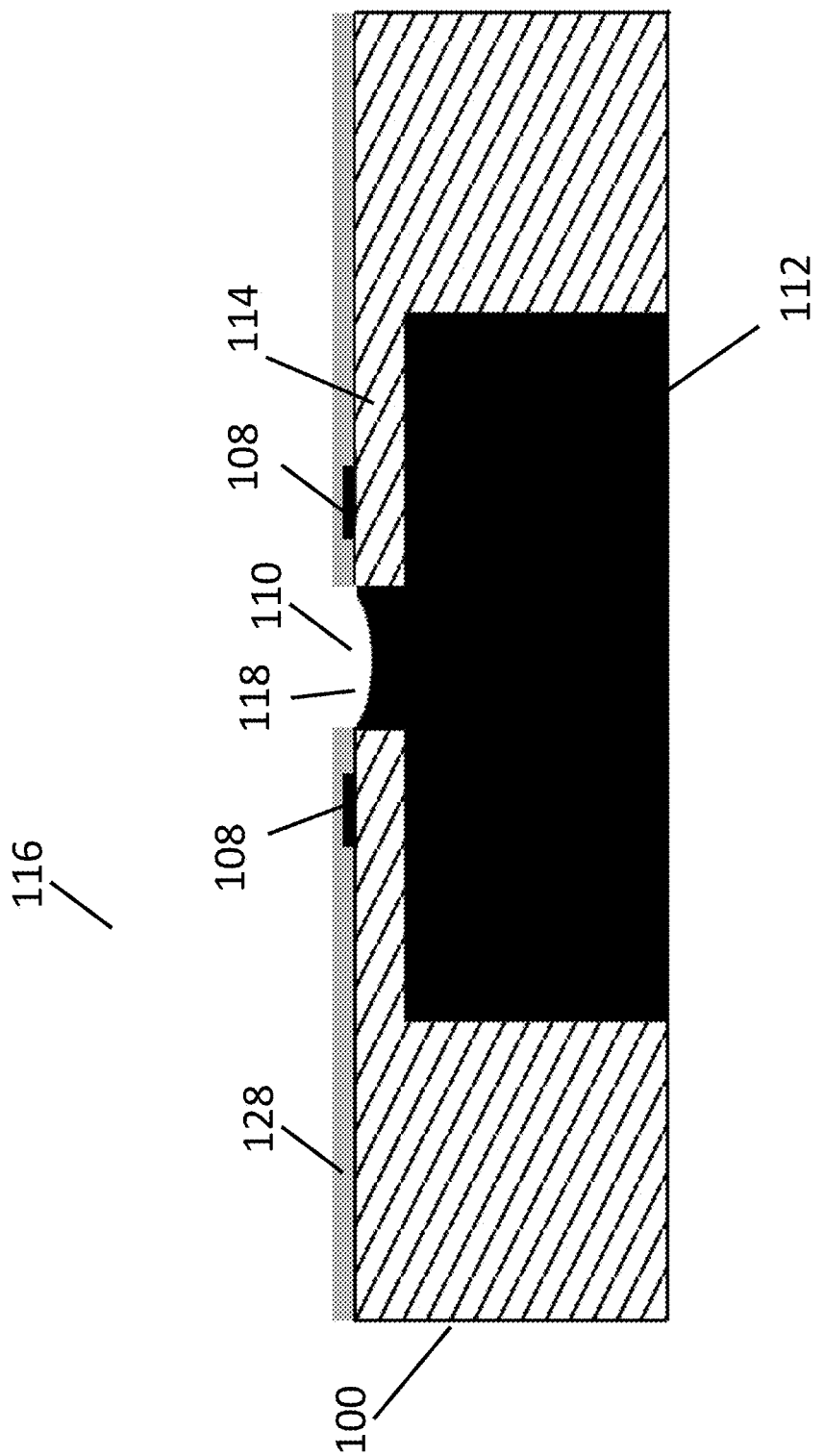

FIG. 14B shows an embodiment where an optional surface coating 128 is coated on the outside of the structure 100, and is located adjacent to the vaporization port 110. I some embodiments it may be desirable to prevent the costing from coating the walls of the vaporization ports 110. Thus when the coating is deposited, the vaporizer ports may be masked off during the coating process. In an embodiment, the optional surface coating 126 is a hydrophobic coating. In another embodiment, the optional surface coating 126 is a hydrophilic coating. In another embodiment, the optional surface coating 126 is a combination of a hydrophobic and a hydrophilic coating. In an embodiment, a hydrophobic coating could be comprised of a fluoropolymer, or other material. In an embodiment, the optional surface coating 126 could be comprised of a chemical monolayer. In an embodiment, a hydrophobic coating could repel hydrophilic liquid and could minimize hydrophilic liquid from wetting the outside of the structure. In an embodiment, a hydrophilic coating could repel hydrophobic liquid and could minimize hydrophobic liquid from wetting the outside of the structure.

Figure 14C:
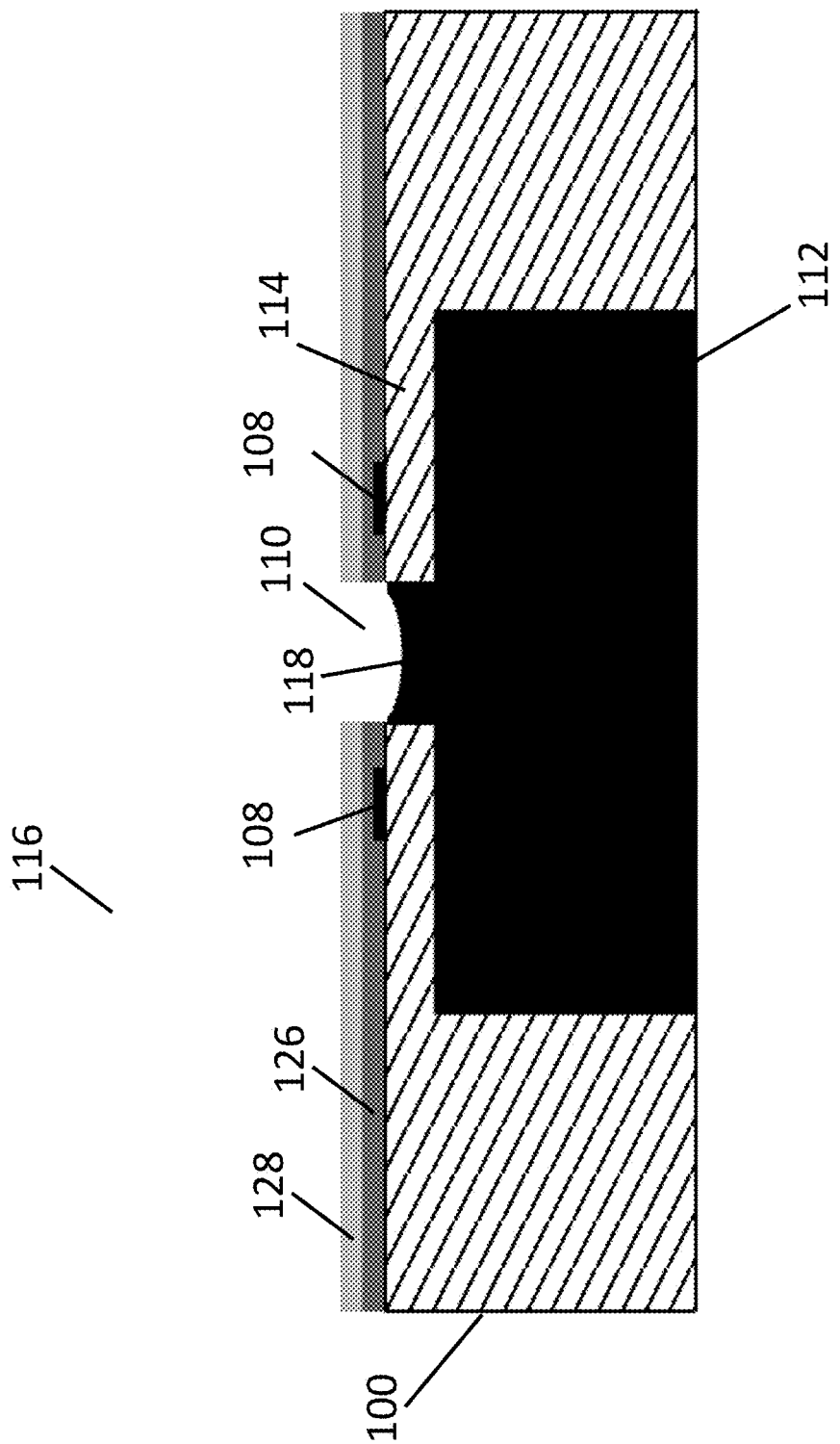

FIG. 14C shows an embodiment where an optional protective layer 126 surrounds the heating element 108, with an optional surface coating 128 that is coated over the optional protective layer 126 that surrounds the heating element 108, and is located adjacent, but optionally not on, the vaporization port 110. The protective layer 126 could be deposited silicon dioxide, amorphous silicon, silicon nitride, alumina, ceramic, or other material. In some embodiments, the protective layer 126 can protect the heating elements 108 from becoming delaminated, due to differences in thermal expansion between the heating element 108 material and the underlying structural 100 material. In some embodiments, the protective layer 126 can serve as a chemical and/or electrical barrier between the heating element 108 and the surrounding environment 116. In some embodiments, the protective layer 126 is located in close proximity to the heating element 108. In some embodiments, the protective layer 126 completely covers heating element 108. In some embodiments, the protective layer 126 is located within 0.5 um to 1 mm of the heating element 108. In some embodiments the protective layer 126 covers the structure 100. In some embodiments, protective layer 126 ranges in thickness from 10 nm-10 um. In an embodiment, the surface coating 128 is a hydrophobic coating. In another embodiment, the surface coating 128 is a hydrophilic coating. In another embodiment, the surface coating is a combination of a hydrophobic and a hydrophilic coating. In an embodiment, an optional hydrophobic surface coating 128 could be comprised of a fluoropolymer, or other material. In an embodiment, an optional hydrophobic surface coating 128 could repel hydrophilic liquid and could minimize hydrophilic liquid from wetting the outside of the structure 100. In an embodiment, a hydrophilic surface coating 128 could repel hydrophobic liquid and could minimize hydrophobic liquid from wetting the outside of the structure 100.

FIG. 14D shows an embodiment where an optional surface coating 128 is coated on the inside of the structure 100, and is located adjacent to the vaporization port 110 and the liquid source region 112. In an illustrative embodiment, the optional surface coating 126 is a hydrophobic coating. A hydrophobic coating can be adapted so that hydrophobic liquids wet the hydrophobic coating. In another embodiment, the optional surface coating 126 is a hydrophilic coating, so that hydrophilic liquids wet the hydrophilic coating. In another embodiment, the optional surface coating 126 is a combination of a hydrophobic and a hydrophilic coating. In an embodiment, a hydrophobic coating could be comprised of a fluoropolymer, or other material. In an embodiment, the optional surface coating 126 could be comprised of a chemical monolayer. In an embodiment, a hydrophobic coating could repel hydrophilic liquid and could minimize hydrophilic liquid from wetting inside the structure 100 and vaporization port 110, while allowing a hydrophobic liquid to wet inside the structure 100 and vaporization port 110. In an embodiment, a hydrophilic coating could repel hydrophobic liquid and could minimize hydrophobic liquid from wetting the inside of the structure 100 and the vaporization port 110.

FIG. 14D shows an illustrative embodiment with an optional structure heater 210 that can be used to apply thermal energy to the structure. The optional structure heater can be a thin film resistive heating element or other type of heating element. Thermal energy from the structure can be used to warm a solid material 212. Solid material 212 can be a solid wax or wax-like substance, or any other type of solid material. The solid material 212 is in thermal communication with structure 100. With the proper application of thermal energy from structure 100, solid material 212 can be controllably melted into a liquid that can occupy liquid source region 112. Optional surface coating 128 can be chosen such that liquid occupying liquid source region 112 can wet structure 100 and vaporization port 110. When heating element 108 is energized, liquid from liquid source 112 can be vaporized in vaporization port 110, such that vapor can be emitted into the surrounding environment 116.

Figure 15:
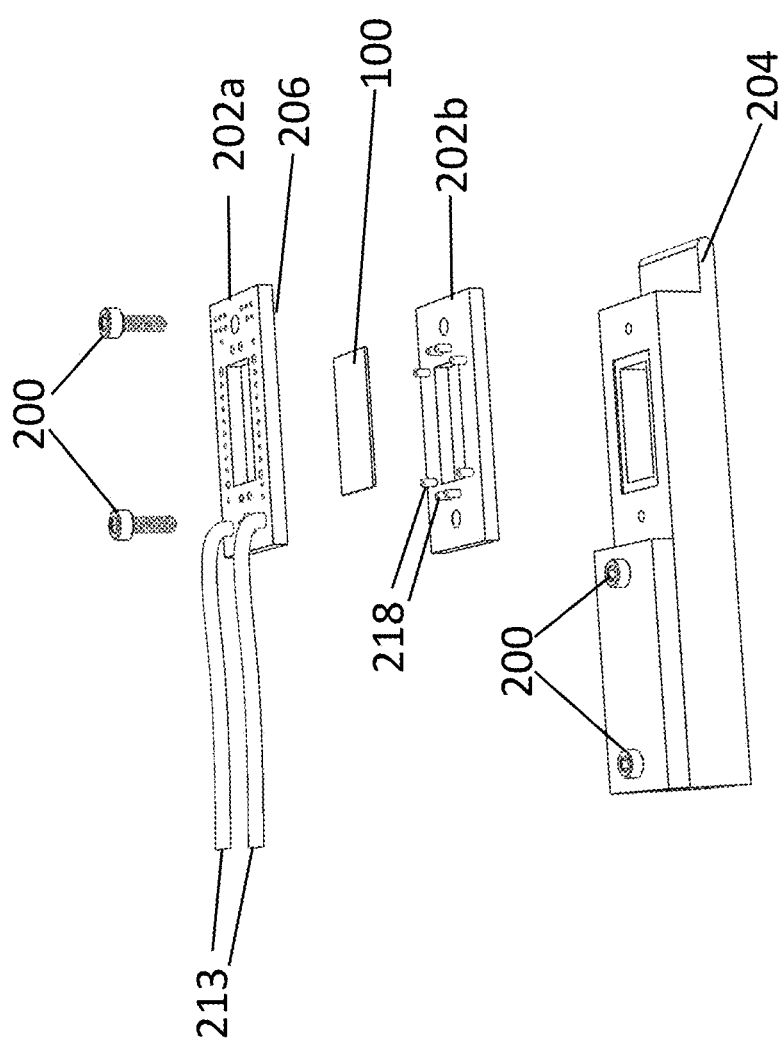
FIG. 15. Shows an exploded view of the apparatus of an illustrative embodiment, depicting major components of an interposer.

FIG. 15 depicts an exploded view of an assembly of interposer body 204 and its associated components for an illustrative embodiment. Alignment pins 218 laterally locate vaporization structure 100 between the upper retaining ring 220a and lower retaining ring 202b. In an illustrative embodiment, electrical interconnect 206 is located on the lower side of the top interposer retaining ring 220a, and is in electrical communication with electrical wires 213 and microfluidic device structure 100. In an illustrative embodiment, retaining bolts/screws 200 affix retaining rings 220a and 220b, microfluidic device structure 100 to interposer body 204. In an illustrative embodiment, without loss of generality, retaining bolts/screws 200 can be replaced with many other types of fasteners, such as plastic clips, snap clips, and many others.

In an illustrative embodiment, electrical wires 213 provide electrical power to vaporization structure 100 through electrical interconnect 206. In an illustrative embodiment, electrical power to vaporization structure 100 may be provided through lower retaining ring 202b. In an illustrative embodiment, electrical power may be provided to vaporization structure 100 directly from interposer 204, which may be configured to route electrical power along its surface or through its volume. In an illustrative embodiment, Polydimethylsiloxane (PDMS) may be used to seal structure 100 to retaining ring 202.

Figure 16:
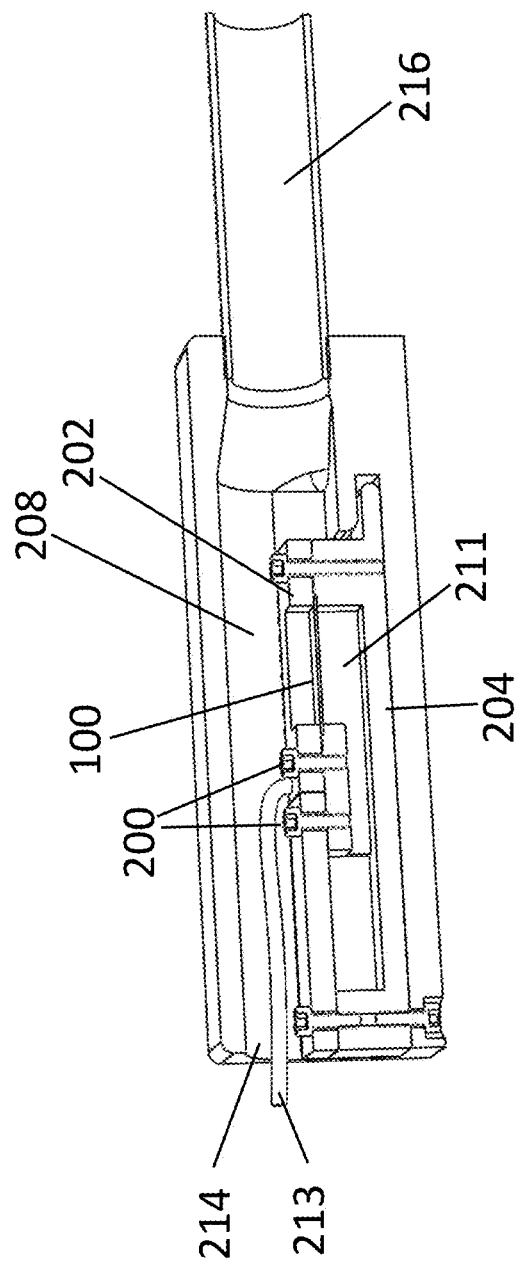
FIG. 16 Shows a cross-section perspective view of the apparatus of an illustrative embodiment.

FIG. 16 depicts a cross-sectional view of an embodiment. The interposer body 204 and interposer retaining ring 202 are in communication with vaporizing structure 100, and constrained by interposer retaining ring bolt 200. Vaporizing structure 100 can be comprised of a microfluidic chip. Liquid (or in some embodiments a solid/wax) to be vaporized is contained in fluid reservoir 211. Vapor production region 208 is in fluid communication with structure 100 and allows vapor to emanate from microfluidic device structure 100, and allows vapor to combine with air coming from air inlet 214 and exit through air outlet 216. Electrical energy is provided from an electrical power supply through electrical wire 213 to electrical interconnect 206 (not shown in FIG. 16), which is in electrical communication with microfluidic device vaporizing structure 100.

In some embodiments, the interposer body 204 is comprised of injection-molded plastic and designed for ease of assembly. In some embodiments, the interposer body 204 can be 3-D printed, machined, and can be made from a large selection of plastics, metals, fiberglass, composites, ceramics, or other structural materials.

Electrical interconnects 206 (not shown in FIG. 16) allow the device to be connected an electronic control unit (not shown in FIG. 16). In some embodiments, the electrical interconnects could be formed from a conducting tape, flat wire, wire bond, bump bond, solder bond or other connection process. In some embodiments, the electrical interconnects could be formed from a printed circuit board. Electrical connections between the top and bottom surfaces of the printed circuit board may be facilitated by through-holes, otherwise commonly referred to as vias. In some embodiments, the electrical connections between the top and bottom surfaces of the printed circuit board may be facilitated by conductors, such as wires, metal or metallized tape, and the like which are routed externally to the printed circuit board body.

In an illustrative embodiment, the overall dimensions of the plastic housing could be nominally 4 mm×6 mm×12 mm. In an illustrative embodiment, the plastic housing could range in dimensions from less than 0.1 mm to more than 100 mm, and could contain one or more microfluidic devices.

Figure 17A:
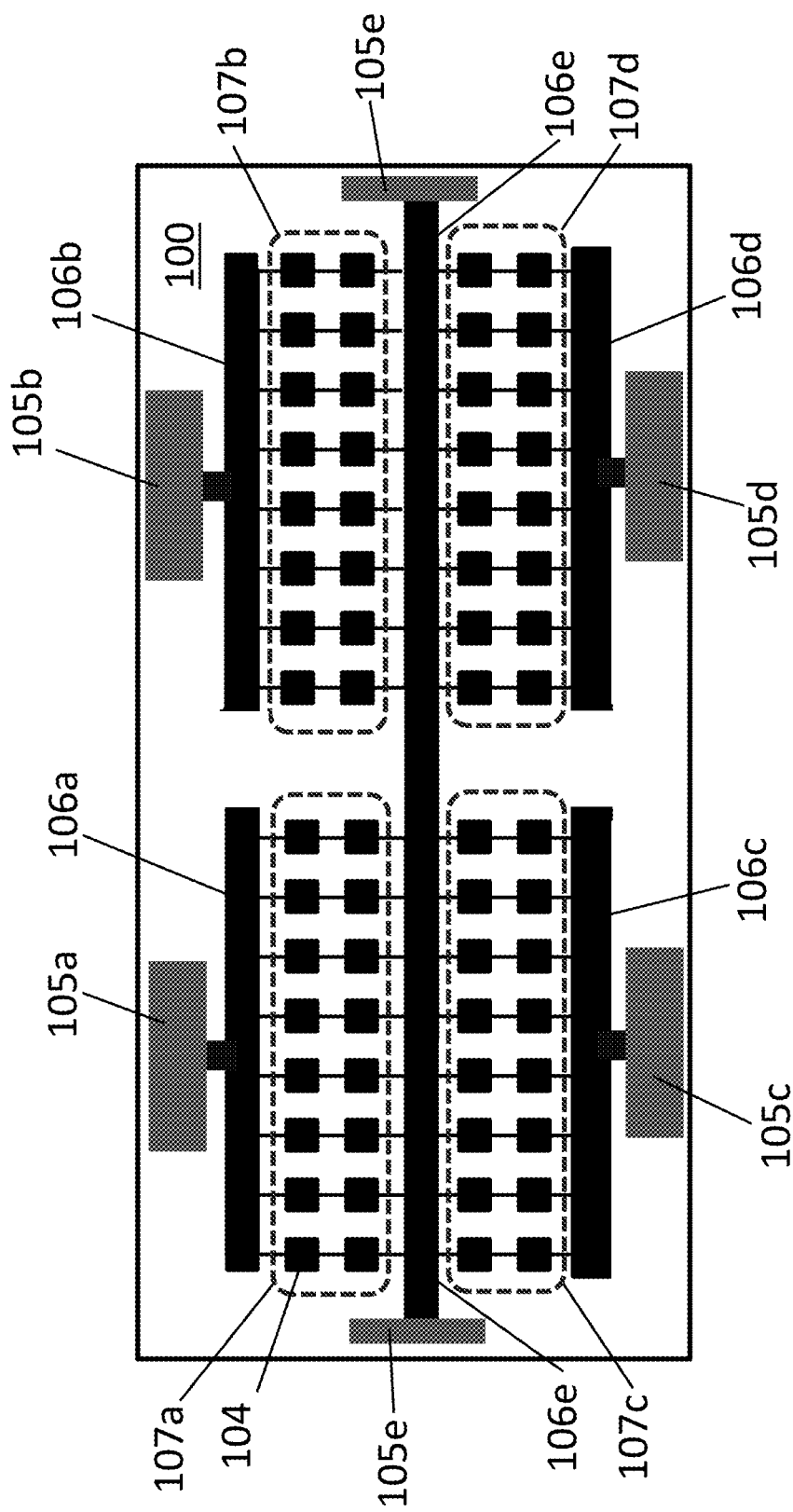
FIGS. 17A, 17B and 17C show top views of the apparatus of an illustrative embodiment.
Figure 17B:
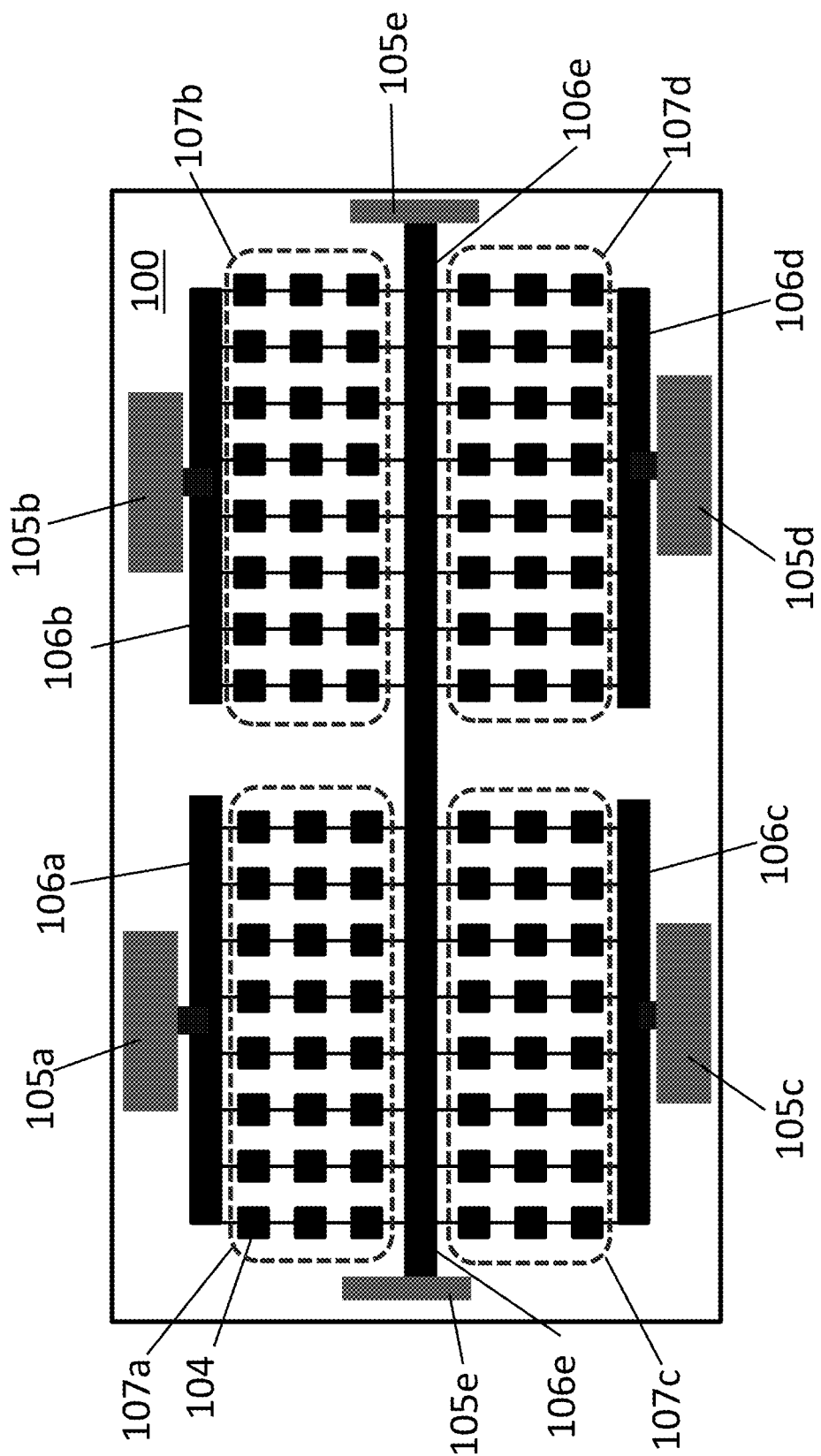
Figure 17C:
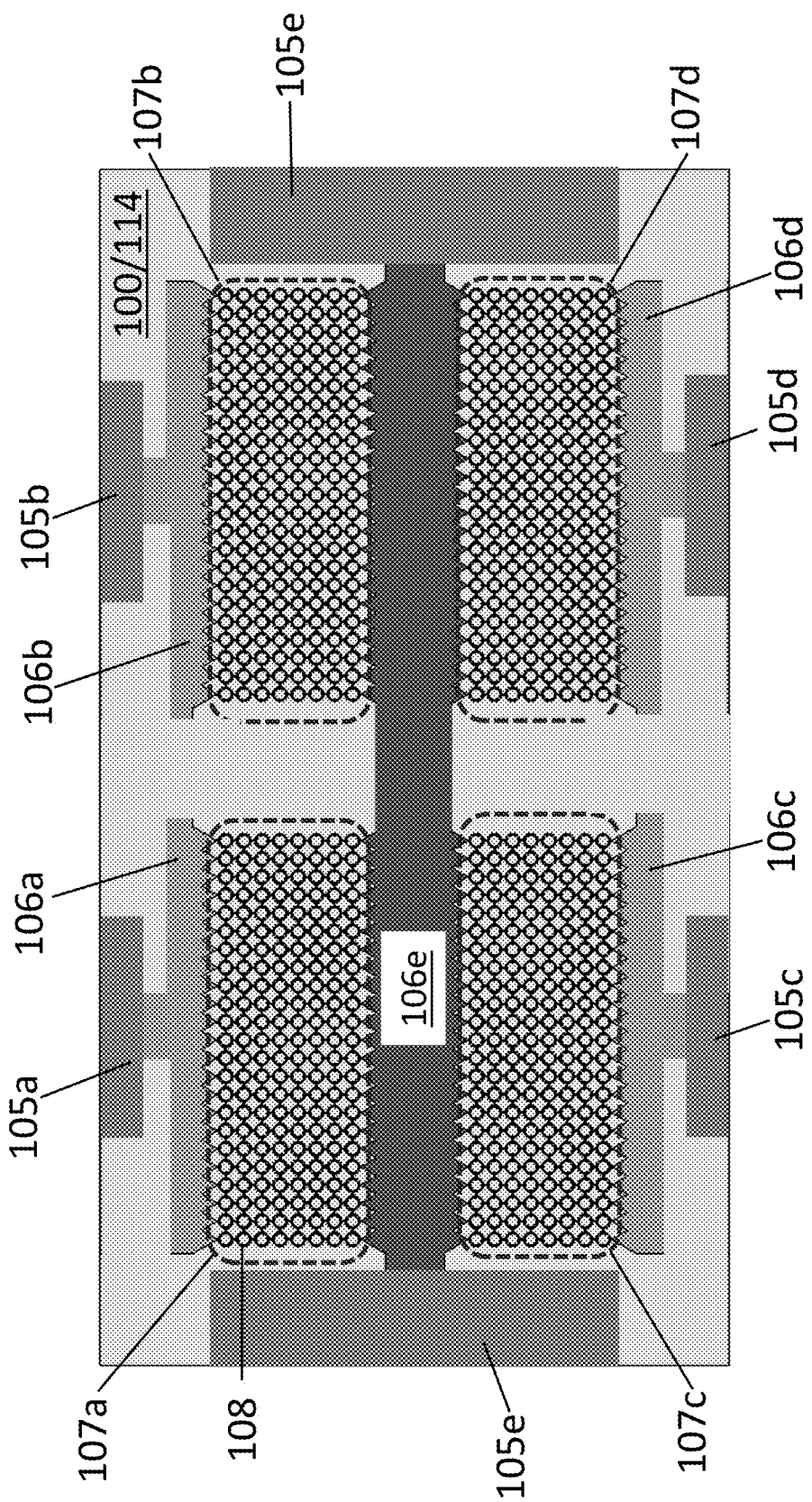

FIGS. 17A, 17B and 17C show an overview of an exemplary single microfluidic vaporization device structure 100. In an illustrative embodiment vaporization clusters 104 are partitioned into groups referred herein as vaporization sectors 107a, 107b, 107c and 107d. The number of vaporization sectors 107 can be any number, and can be chosen judiciously for the specific application and performance requirements. Each vaporization sector 107 can be individually and/or selectively addressed by electrically exciting electrode leads 106.

In some embodiments, electrode leads 106 can be formed from a different metal, and have different dimensions than heating elements 108 (see for example FIG. 17C), and can therefore be designed to have a relatively low electrical resistance compared to a plurality of heating elements 108. In some embodiments, electrode leads 106 can be configured to be relatively thick, can range in thickness from 0.1 um-10 um. In some embodiments, electrode leads 106 could be comprised of platinum, gold, titanium, aluminum, and other metals or conductive materials. In some embodiments, aluminum could be advantageous as it is relatively low cost compared to coinage metals.

According to an illustrative embodiment, vaporization sector 107a can be electrically energized by electrically connecting electrode lead 106a and electrode lead 106e to an electrical power supply, such as a battery, capacitor, or other electrical power supply, to complete a circuit. In an illustrative embodiment, electrode leads 106a, 106b, 106c, and 106d could be connected to a positive terminal, and electrode lead 106e to a negative terminal, of a battery or other electrical power supply. In an illustrative embodiment vaporization sectors 107a, 107b, 107c, 107d are individually addressable by electrically energizing electrode leads 106a, 106b, 106c, and 106d, respectively. In an illustrative embodiment, electrode lead 106e can be a common ground and can be electrically connected to at least two vaporization sectors. In an illustrative embodiment, electrode lead 106e can be a common ground and electrically connected to four vaporization sectors. In an illustrative embodiment, electrode lead 106e can be connected to two electrical connection pads 105e. In an illustrative embodiment, electrode lead 106e can have two electrical connection pads 105e that are located on opposite edges of substrate 100, which can facilitate transport of large amounts of current being transported, with minimal voltage drop on electrode lead 106e.

In an illustrative embodiment, electrode leads 106 are electrically connected to electrical contact pads 105, which interface to electrical interconnects 206. In some embodiments, a plurality of electrical contact pads 105 can be located near a plurality of edges of structure 100. In an illustrative embodiment, six electrical contact pads 105 can be located near four edges of structure 100. The contact pads 105 could be distributed over a relatively large area to help ensure good electrical contact, especially for high electrical current applications.

In some embodiments, a plurality of electrical contact pads 105 can be located near a plurality corners of structure 100. In some embodiments, a plurality of electrical contact pads 105 can be located near a combination of plurality of edges and corners of structure 100.

In an illustrative embodiment, vaporization sector 107a can be actuated by electrically energizing electrode lead 106a and grounding electrode lead 106e. In an illustrative embodiment, vaporization sector 107b can be actuated by electrically energizing electrode lead 106b and grounding electrode lead 106e. In an illustrative embodiment, vaporization sector 107c can be actuated by electrically energizing electrode lead 106c and grounding electrode lead 106e. In an illustrative embodiment, vaporization sector 107d can be actuated by electrically energizing electrode lead 106d and grounding electrode lead 106e.

In an illustrative embodiment, electrode lead 106e can be configured to be electrically common (i.e. electrically connected) to one or more vaporization sectors 107. In the illustrative embodiments depicted in FIGS. 17A, 17B, and 17C, each electrode lead 106e is electrically connected to four vaporization clusters 107.

FIG. 17A shows an illustrative embodiment of a single device structure 100 that contains 4 vaporization sectors 107, where each vaporization sector 107 contains 16 vaporization clusters 104 connected in 8 parallel circuits, each with a series of 2 vaporization clusters 104. Each vaporization cluster 104 can contain a predetermined number of heating elements, that are each electrically connected in series and parallel combination (such as the illustrative embodiment shown in FIG. 5).

FIG. 17B shows an illustrative embodiment of a single device structure 100 that contains 4 vaporization sectors 107, where each vaporization sector 107 contains 24 vaporization clusters 104 connected in 8 parallel circuits, each with a series of 3 vaporization clusters 104. Each vaporization cluster 104 can contain a predetermined number of heating elements, that are each electrically connected in series and parallel combination (such as the illustrative embodiment shown in FIG. 5).

FIG. 17C shows another illustrative embodiment, where individual heating elements 108 are connected to electrode leads 106. The heating elements are partitioned into groups referred herein as vaporization sectors 107. In an illustrative embodiment, 4 vaporization sectors 107 are shown, with each sector 107 containing 23 parallel circuits, each with 8 heating elements 108 in series. In this illustrative embodiment, a total of 8×23×4=736 heating elements 108 are depicted. In this illustrative embodiment, thin structural region 114 coincides with structure 100.

It should be noted that the embodiments shown in FIG. 17 are illustrative and there can be any number of vaporization sectors 107, vaporization clusters 104, and heating elements 108, which can be pre-determined and chosen depending upon the particular application and performance metrics desired.

FIG. 17A shows an illustrative embodiment a single device structure 100 contains eighteen vaporization clusters 104 with each cluster 104 containing seven vaporization ports 110, for a total of 18×7=126 vaporization ports 110 for this example embodiment. In one example embodiment shown in FIG. 6A, two vaporization clusters 104 are connected by electrode leads 106 in series with nine parallel circuits. In another example embodiment shown in FIG. 17B, three vaporization clusters 104 are connected by electrode leads 106 in series with nine parallel circuits.

Vaporization sectors 107 can be individually and/or selectively addressed so that there is flexibility in how they are energized. For example, all vaporization sectors 107 can be energized simultaneously, or vaporization sectors 107 can be energized in a specified time sequence. In some embodiments, it may be desirable to pulse each sector for a time duration e.g. from 1 µs to 1 ms, or from 1 ms to 100 ms, or from 50 ms to several seconds, or even longer, depending upon the application and desired performance metrics.

During operation, heating elements 108 may become damaged, electrically shorted, or degraded, vaporization ports 110 may become degraded, and vaporization may not be of desired quality or of a desired amount. In these cases, the underperforming or damaged vaporization sector 107 can be avoided, and no longer used.

The operational lifetime for the vaporizer may be extended by judicious choice of how the vaporization sectors 107 are electrically energized. In certain embodiments, operational lifetime can be extended by energizing all vaporization sectors 107 simultaneously. In certain embodiments, operational lifetime can be extended by repeatedly energizing only one vaporization sector 107 until vaporization performance decline to a sufficiently low level, and then repeatedly energizing another single vaporization sector 107. The process can be repeated until the useful lifetime of each vaporization sector 107 is consumed.

In other embodiments, the operational lifetime for the vaporizer may be extended by energizing an individual vaporization sector 107 for only a short time duration, e.g. from 1 µs to 1 ms, or from 1 ms to 100 ms, or from 50 ms to several seconds, or even longer, depending upon the application and desired performance metrics. By pulsing each individual vaporization sector 107 for a short period of time, it is less likely that the vaporization port 110 will have an excessively high temperature, become dried-out and potentially become damaged.

In an example embodiment, the microfluidic device structure 100 is 4 mm×10 mm in lateral dimension and 0.1 mm thick. In an example embodiment, the microfluidic chip is fabricated from glass, but for other embodiments, it could be fabricated from plastic, silicon, titanium, metals, ceramics, PDMS, polymers, fiberglass, composites, or other materials.

Joule heating from a resistive element can be described by $Q=V^2/R$, where Q is the Joule heating power, V is the voltage drop across the resistive element and R is the electrical resistance of the element. As temperature increases, the electrical resistance of typical metals such as aluminum, copper, nickel, nichrome, platinum, tin, tungsten, and zinc increases. If the voltage drop is constant, the amount of Joule heating will decrease with increasing temperature. Therefore, in an embodiment, it can be advantageous to have parallel circuits. If one branch of the parallel circuit has a higher temperature than another branch of the circuit, the branch with a higher temperature will have a higher resistance, and will therefore produce less Joule heating. In an embodiment with parallel resistive heaters, the various branches of the circuit may have self-regulating properties, that may help to regulate Joule heating that may help to maintain more uniform temperatures in comparison to the reduced uniformity which could occur using non-parallel circuit configurations. In some embodiments, particular metals or combinations of metals forming an alloy or mixture may be selected in order to optimize or otherwise tune or adjust the thermal self-regulating properties of the structure.

In some embodiments, parallel resistive heaters could be configured with different resistance in each branch. In some embodiments, resistance of the heating elements could be modified by using different materials, different depths, different lengths, and/or different widths. In some embodiments, branches of parallel resistive heaters can have different resistances that could be optimized to produce desirable and well-controlled temperature distributions. In some embodiments, uniform temperature distributions may be desirable. In some embodiments, non-uniform temperature distributions may be desirable.

In some embodiments a hierarchical combination of parallel and resistive heating elements 108 can be judiciously chosen to provide desired heating profiles, and self-regulating heating elements.

In some embodiments, semiconductor elements such as field effect transistors (FETs) could be used in conjunction with electrode leads 106 to provide addressability to heating elements 108.

Figure 18A:
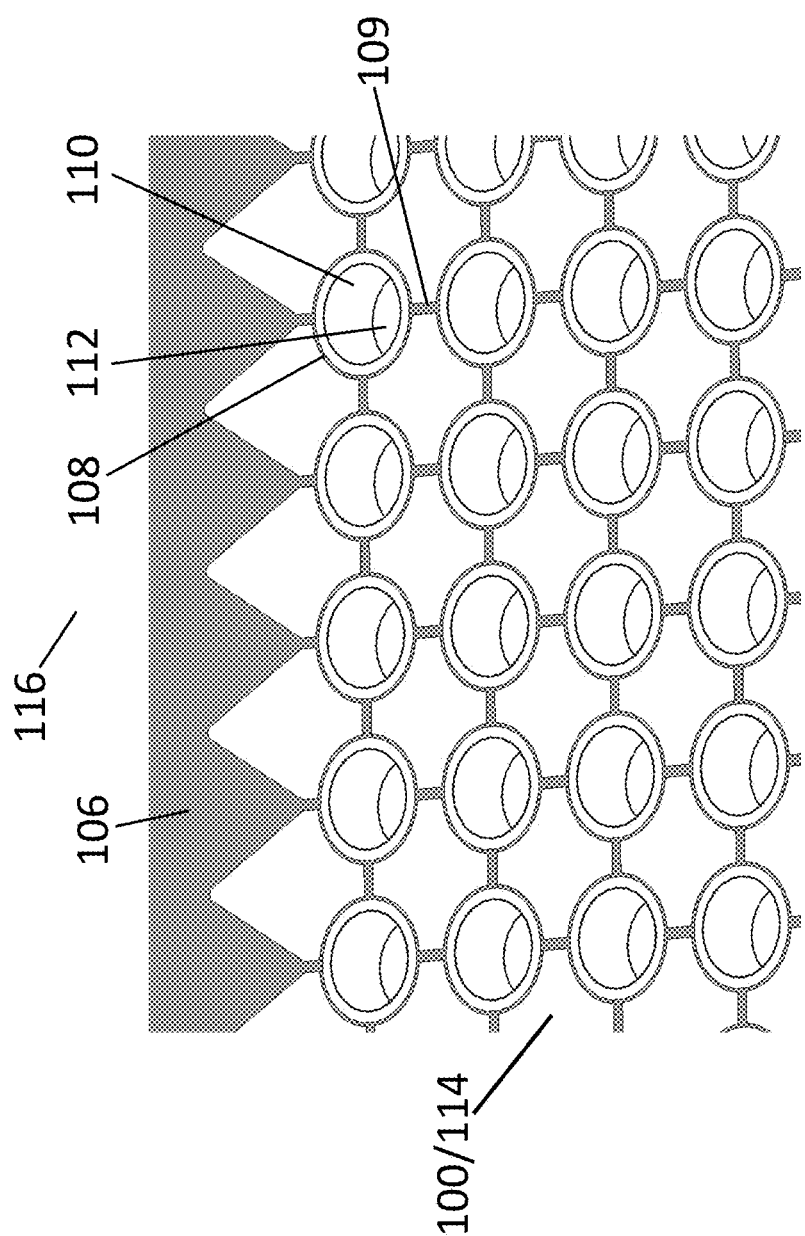
FIGS. 18A, 18B, 18C and 18D show views of the apparatus of an illustrative embodiment, depicting major components of the vaporizer.
Figure 18B:
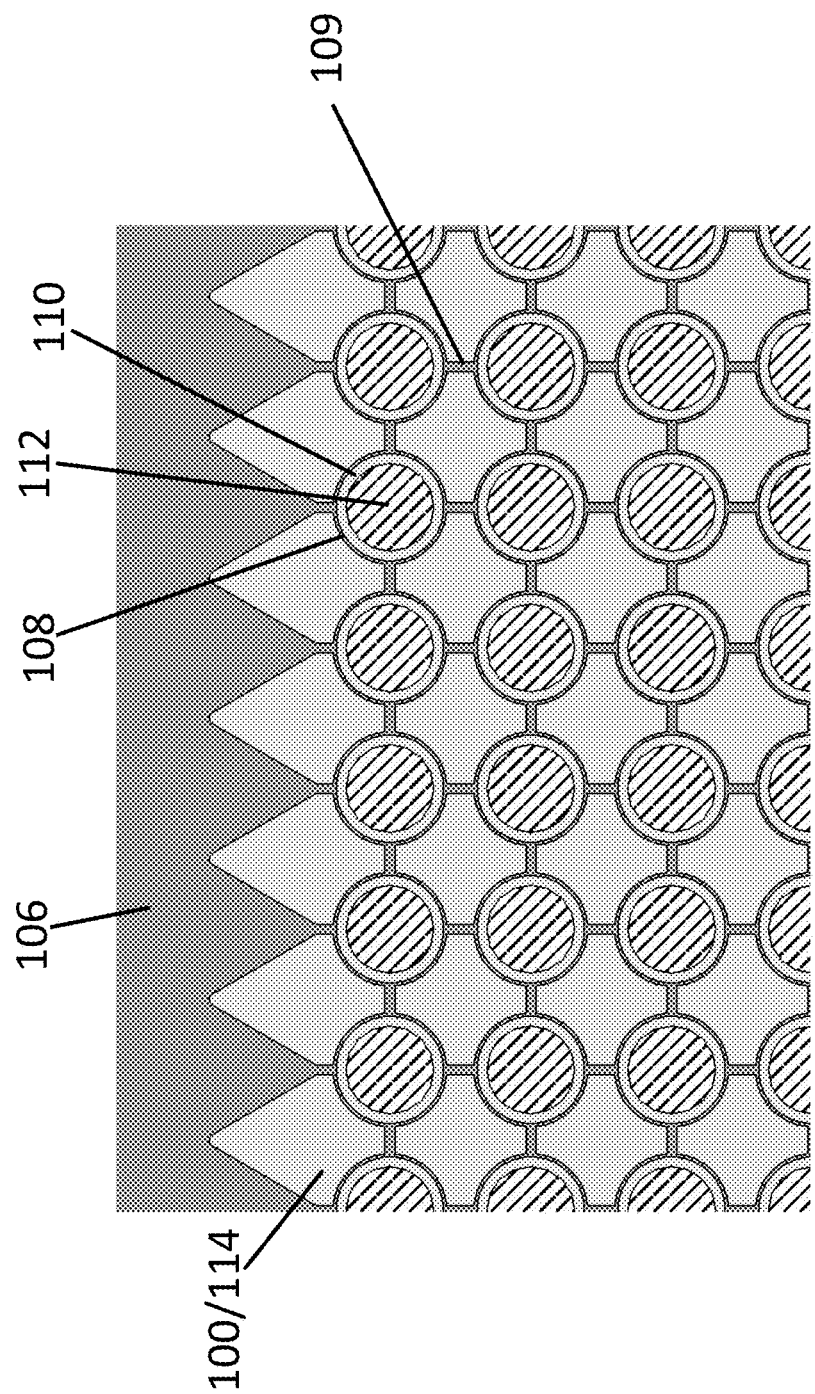
Figure 18C:
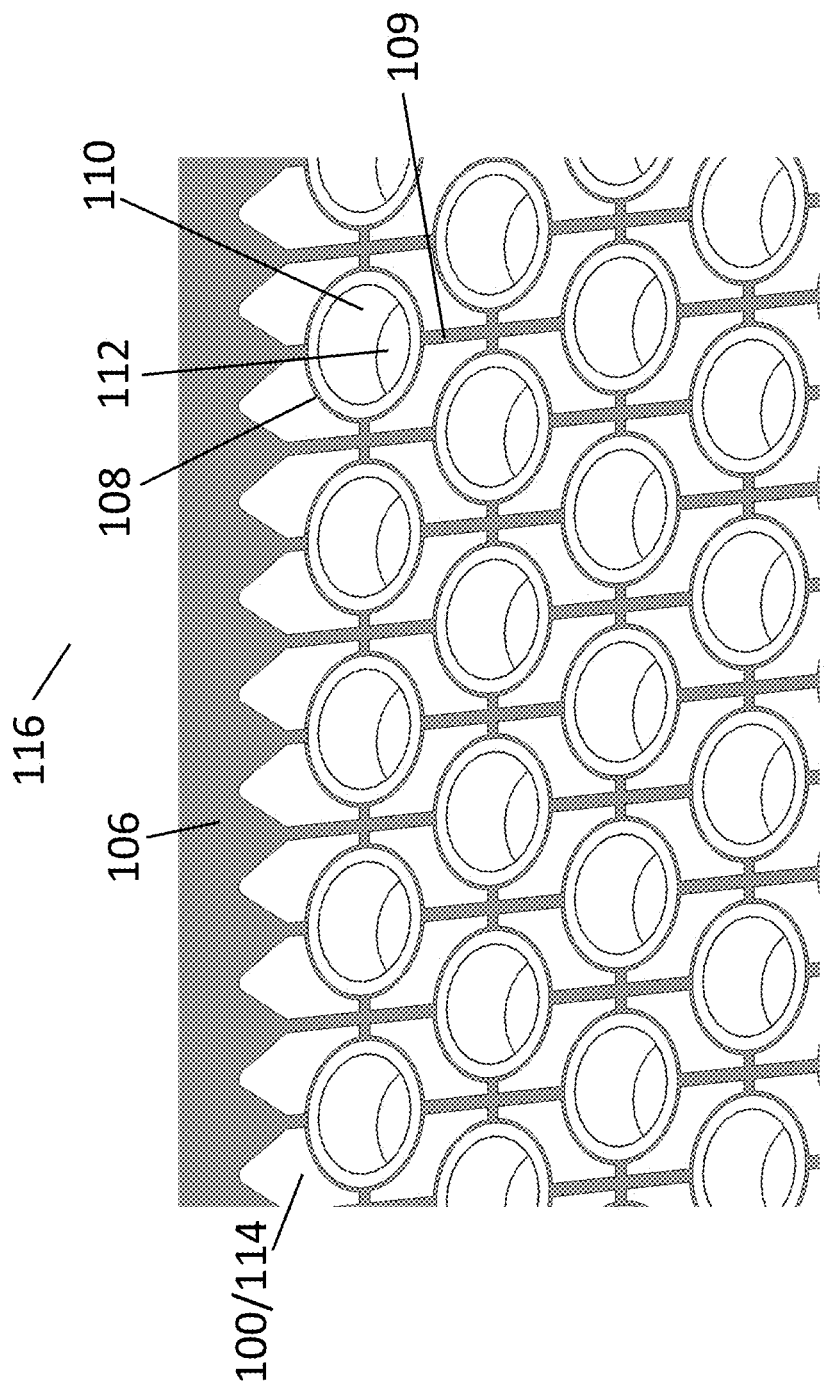

FIGS. 18A, 18B and 18C shows a profile views of the top of several apparatuses depicting some of the major components of an embodiment. Vaporization ports 110 are formed in the structure 100 and are in fluid communication with the liquid source region 112 and the surrounding environment 116. In an illustrative embodiment, thin structural region 114 coincides with structure 100. Heating element 108 is in thermal communication with the vaporization port 110 and located on a thin structural region 114. In an embodiment, the heating element 108 is a thin film resistive heating element.

FIGS. 18A, 18B and 18C show a detailed views of example embodiments, where vaporization ports 110, with lateral dimensions of 60 um-150 um, and heating elements 108 in thermal communication with the vaporization ports 110 such that heat produced by the heating elements 108 is transported to the region of the vaporization ports 110 which is in fluid communication with fluid liquid source 112. In illustrative embodiments, the vaporization ports can range in size from 10 um to 300 um in lateral dimension, and in other embodiments range from 1 um to 1000 um.

In some embodiments, a plurality of heating elements 108 are connected with a plurality of heating element connectors 109. In some embodiments, heating elements 108 are electrically connected in series and parallel combination. In some embodiments, the relative dimensions of heating elements 108 and heating element connectors 109 are configured to provide substantially-uniform temperature distribution. In some embodiments, heating element connectors 109 are configured to provide a highly networked electrical circuit. In some embodiments, a highly networked electrical circuit can provide redundancy, if for example, a particular heating element 108 or heating element connector 109 becomes damaged and cannot pass the desired level of electrical current, the electrical current can be automatically rerouted, with minimal disruption of the electrical load and with minimal disruption of the thermal distribution in the vaporization sector 107.

Vaporization ports 110 can be arranged in many configurations, including but not limited to, triangular, square, hexagonal, elongated triangular, trihexagonal, snub square, truncated square, truncated hexagonal, rhombitrihexagonal, snub hexagonal, truncated trihexagonal, and many others. The arrangement may be selected in order to minimize thermal stresses or otherwise adjust the mechanical strain occurring in the vaporizing structure 100 during use.

In some embodiments, the highly-networked parallel/series combination of electrical connection between a plurality of resistive heating elements provides redundant electrical connections. If a particular electrical connection or heating element becomes damaged and no longer passes electrical current, electrical current can be automatically rerouted and thereby rebalancing the electrical load contained with a group or vaporization sector. In some embodiments, the highly-networked parallel/series combination of electrical connection between a plurality of resistive heating elements provides redundant electrical connections for each heating element.

In some embodiments, and a highly-networked parallel/series combination circuit can provide built-in feedback. The resistivity of many metals increases with increasing temperature. If two equally resistive elements are connected in parallel, and if a one branch develops a higher temperature than the other branch, the branch with the higher temperature branch could increase in resistance, and automatically reroute electrical current to the lower temperature branch, thereby increasing the temperature of the lower temperature branch. This type of self-regulation can be an advantage for many illustrative embodiments.

FIGS. 18A and 18B show vaporization ports 110 in a square packing arrangement. Heating elements 108 are connected in a serial/parallel configuration. The width and depth of the heating elements 108 can be controlled at each segment to achieve a desired resistance, and therefore a desired heating profile. By designing the resistance of the heating elements 108 at each position, excessively high temperatures can be avoided.

Figure 18D:
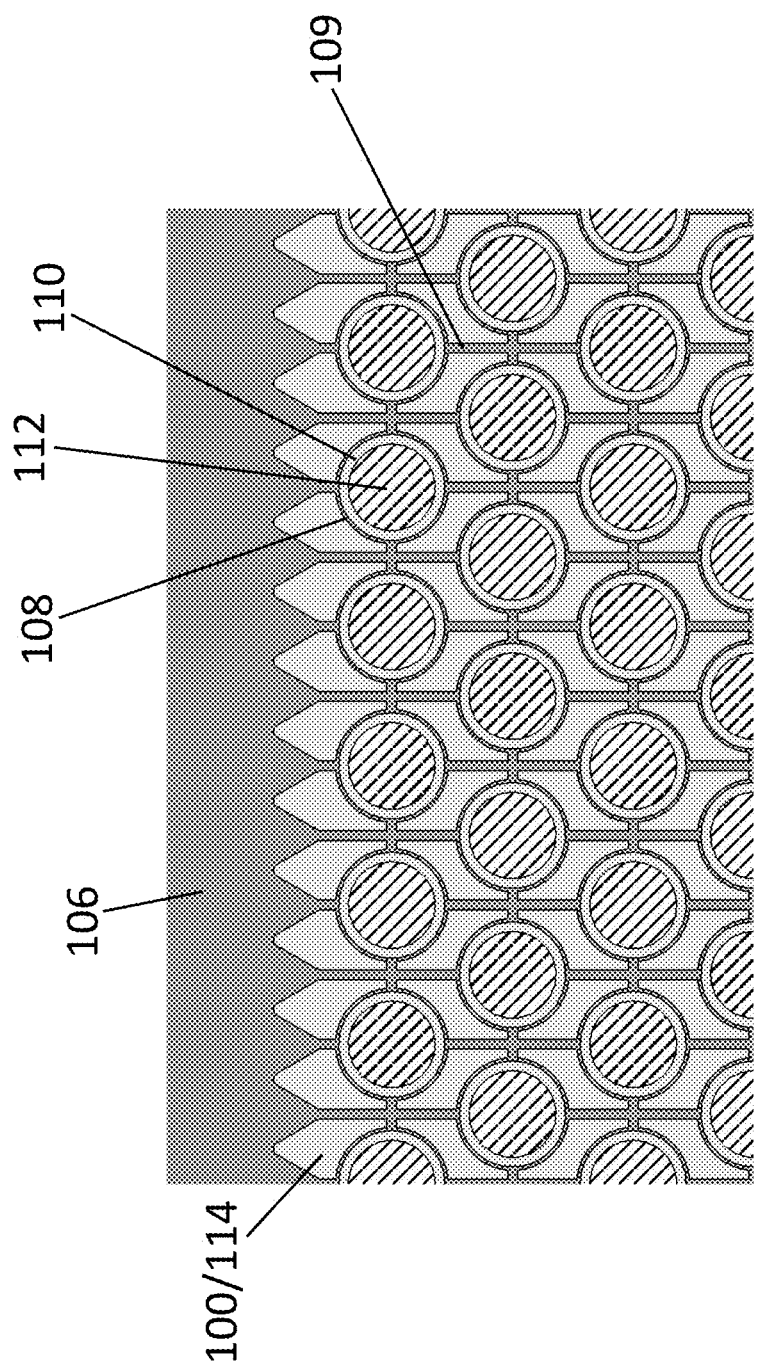

FIGS. 18C and 18D show vaporization ports 110 in a triangular or hexagonal packing arrangement. Heating elements 108 are connected in a serial/parallel configuration. The width and depth of the heating elements 108 can be controlled, at each segment, to achieve a desired resistance, and therefore a desired heating profile. By designing the resistance of the heating elements 108 at each position, excessively high temperatures can be avoided.

The width of the heating elements 108 can be optionally configured with varying widths and thickness, or varying materials to produce a desired Joule heating profile. In some embodiments a desired heating profile may be chosen to provide uniform vaporization of a working fluid, while avoiding excessive heating from undesirable hot-spots. In some embodiments, 0.01 to 500 Watts of heat may be delivered to the fluid to produce vapor 102. In other embodiments, 1 to 50 Watts of heat may be delivered to the fluid to produce vapor 102.

In some illustrative embodiments, a hierarchy of resistive heating elements being connected in parallel (as depicted in FIGS. 18A, 18B, 18C and 18D) may have certain advantages. For example, the electrical resistance of metals can increase with increasing temperature. Therefore, if one element of a parallel circuit has a higher temperature than another element of the parallel circuit, that element could have a higher resistance and force more electrical current through the lower temperature element and thereby increase the Joule heating produced by the lower temperature element. In some embodiments, resistive heating elements connected in parallel could facilitate thermal regulation, which could help mitigate local thermal hot spots.

In some illustrative embodiments, heating elements 108, electrode leads 106, and electrical contact pads 105 can be formed on both sides of structure 100. This could potentially provide redundancy of the electrical connections, and electrical heating elements.

In some embodiments, vaporization ports could be configured with non-circular geometries. For example, in an illustrative embodiment, a vaporization port could be configured to be a slot-type geometry or other non-circular geometry, which could increase the contact surface area 140 in vaporization port 110.

In some illustrative embodiments, wicking materials can be used to transfer liquid to and from one or more fluid reservoirs 211, which comprise the liquid source 112 for vaporizing structure 100. Wicks can be comprised of fibers, meshes, particles and many other geometric shapes. The wicking material can be comprised of many different types of materials, depending upon the type of liquid to be wetted. In some illustrative embodiments, these materials may be silica, ekowool, metal, bamboo, cotton, ceramics, Nextel, natural fiber, hemp, Rayon cellulose, and many other materials.

In some illustrative embodiments, foam-like structures may provide advantageous wicking materials. In some embodiments, inverse-opal structures or other foam-like structures can have a relatively high porosity (up to 70-90% or greater), while exhibiting relatively high surface area, which can be advantageous for many wicking applications. This may provide a mechanism for increased capillary action through surface tension, while having a relatively high permeability, to provide more efficient viscous flow, compared to other types of wicking structures.

In some embodiments, foam-like structures comprising metal or silica may be suitable wicking materials. In some embodiments, foam-like wicking structures can be microfabricated directly on structure 100. In some embodiments, foam-like wicking structures can be microfabricated directly on the backside of structure 100. In some embodiments, foam-like wicking structures can be microfabricated directly on the front-side of structure 100. In some embodiments, foam-like wicking structures can be microfabricated directly in vaporization port 110 located on structure 100.

In some embodiments, foam-like silica wicking structures can be microfabricated directly on the back-side of structure 100, which could be comprised of a silica substrate or other glass-like material.

Figure 19A:
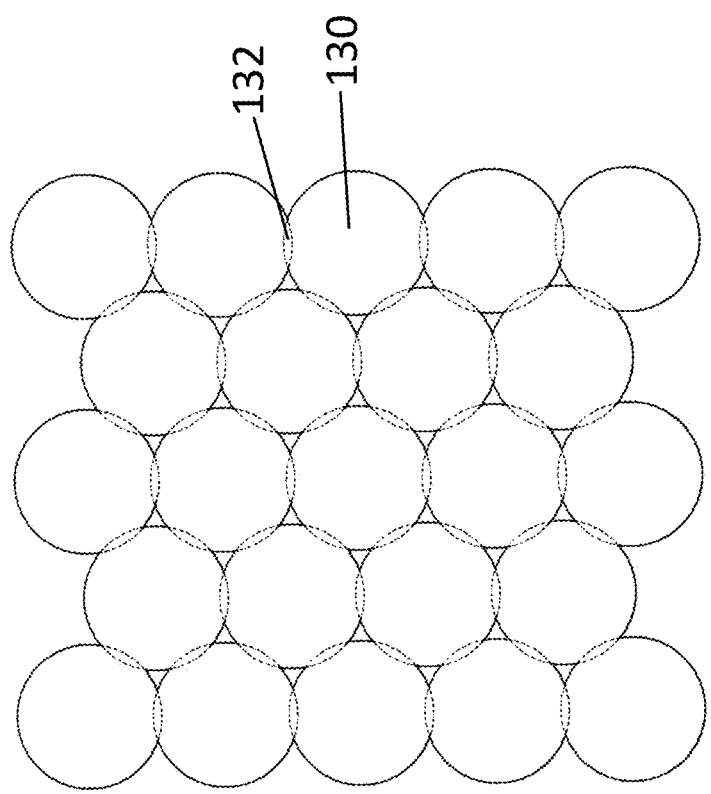
FIGS. 19A, 19B, 19C, and 19D show illustrative views, at several stages of fabrication, of an inverse opal wicking structure comprising an illustrative embodiment.
Figure 19B:
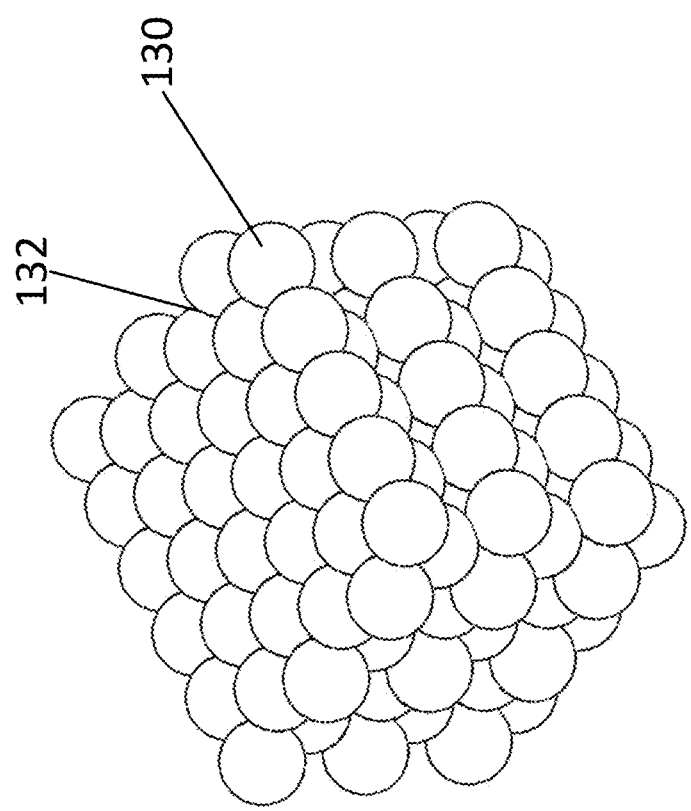

FIGS. 19A, 19B, 19C and 19D show various components that occur during fabrication of an inverse-opal structure, for an illustrative embodiment. FIG. 19A shows a cross-section of particles or beads 130 that are sintered to provide sintered interface 132. FIG. 19B shows a perspective view of an illustrative embodiment of a collection of particles or beads 130 that are sintered to provide sintered interface 132. In some illustrative embodiments, particles or beads 130 can be substantially spherical in shape. In some illustrative embodiments, particles or beads 130 can be range in size from say 10 nm to 10 mm in diameter, or even larger. In some illustrative embodiments, particles or beads 130 can be range in size from say 1 µm to 1 mm in diameter. In some illustrative embodiments, particles or beads 130 can be range in size from say 10 µm to 300 µm in diameter. In some illustrative embodiments, particles or beads 130 can be of arbitrary shape and arbitrary size.

In some illustrative embodiments, the interstitial region between sintered particles or beads 130 can then filled with a material. In some illustrative embodiments, the filling material can be metal, and filled by electroplating. The filling materials could include one or more of copper, nickel, or any other metal, metal oxide, or metal alloy. In some embodiments, titanium, tinania, and titanium alloys could be used. In some embodiments, metal is advantageous as it has a relatively high thermal conductivity. In other embodiments, metal is disadvantageous due to its relatively high thermal conductivity, as there could be undesirable parasitic heat loss. In some embodiments, nickel is advantageous as it has relatively high magnetic permeability and could be used for magnetic inductive heating.

In some illustrative embodiments, the filling material can be silica, and filled by hydrolysis of tetraethyl orthosilicate (TEOS, commercially available from Sigma Aldrich). In some illustrative embodiments, the filling material can be silica, and filled by hydrolysis of tetramethyl orthosilicate (TMOS). Silica has the advantage in that it can be bonded directly to silica substrates, and its thermal expansion coefficient can be closely matched to glass-based substrates.

In some embodiments, the beads or particles 130 can be sacrificial, and can be removed leaving an inverse opal structure attached to the backside of the substrate. The sacrificial beads 130 can be removed using a variety of solvents. For example, in some embodiments, toluene can be used to dissolve polystyrene beads 130, without adversely affecting other components on the apparatus. In some embodiments, sacrificial particles can be removed thermally using calcination.

Figure 19C:
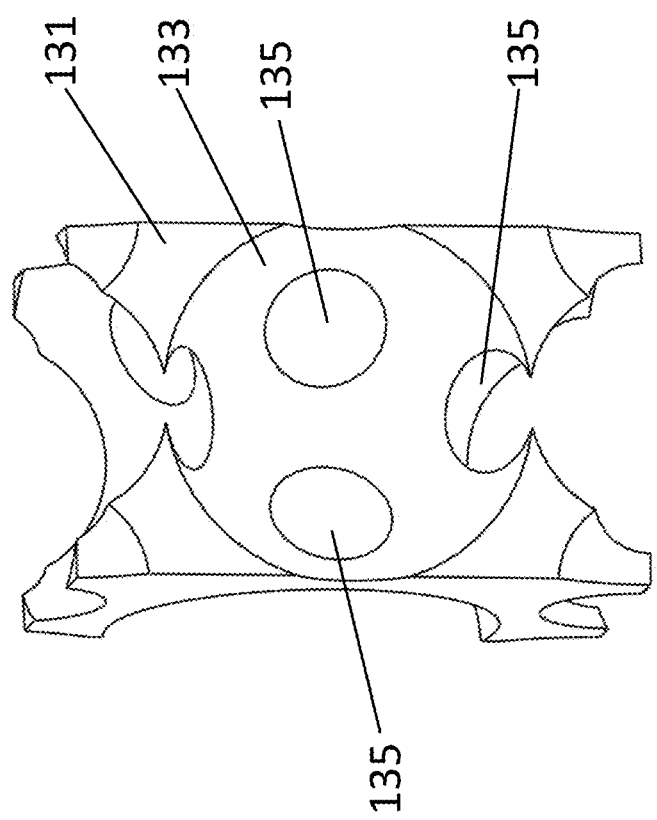
Figure 19D:
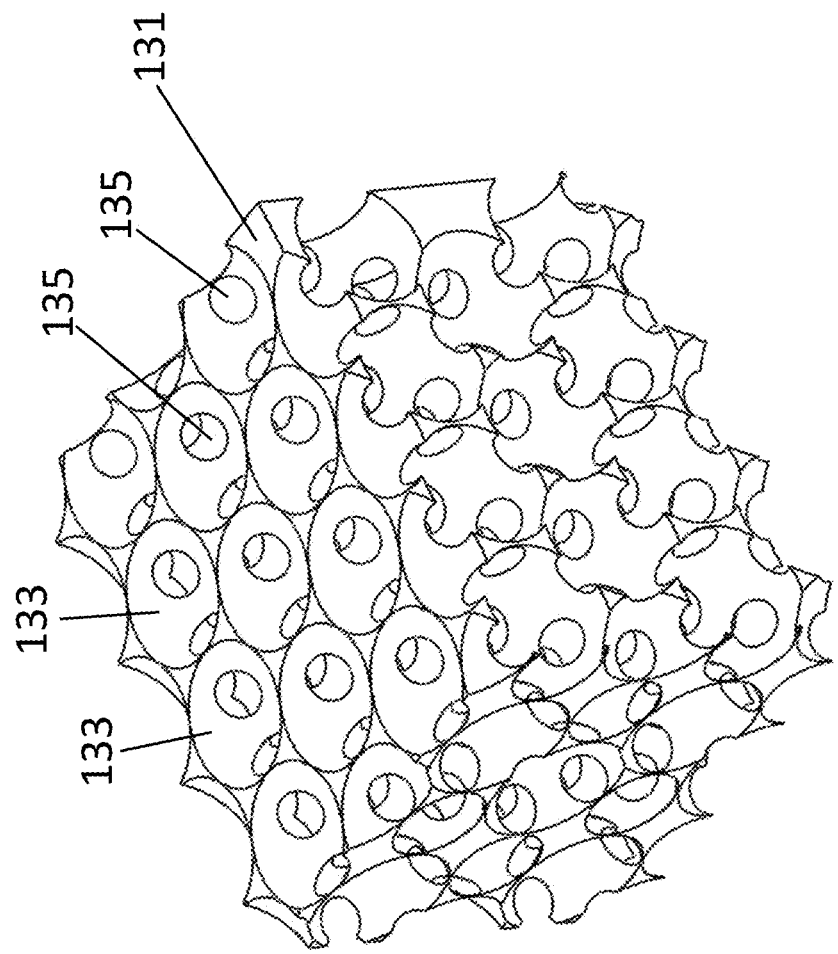

FIG. 19C shows a perspective view of a segment of an inverse-opal wick 131 of an illustrative embodiment. FIG. 19D shows a perspective view of a segment of an inverse-opal wick 131 of an illustrative embodiment. In some illustrative embodiments, inverse opal structures have the advantage in that they can be fabricated in a highly repeatable manner, fabricated on a large scale (up to centimeters), and fabricated at a relatively low cost.

In some illustrative embodiments, for a given size of sacrificial template particles, an inverse opal structure can have two characteristic sized pores. A larger pore 133 can have a size that can be determined by the size of the template particle 130. A smaller pore 135, which can be determined by a combination of the size of the template particle 130 and amount of sintering. The smaller pore 135 interconnects the larger pores 133, forming a highly cross-linked networked structure, which can be advantageous for wicking.

Figure 20A:
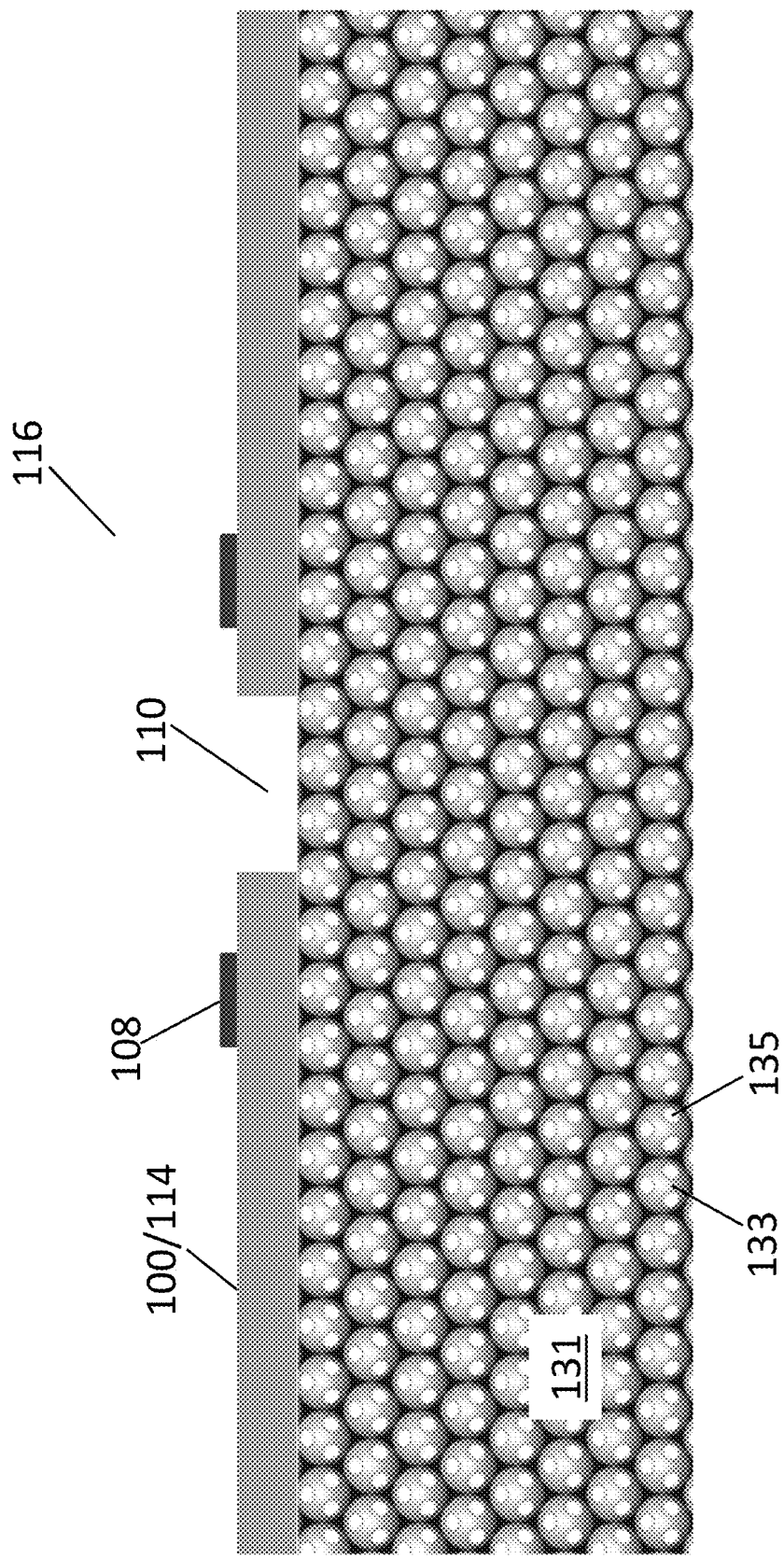
FIGS. 20A, 20B, 20C, and 20D show profile views of the apparatus depicting the major components of an illustrative embodiment.
Figure 20B:
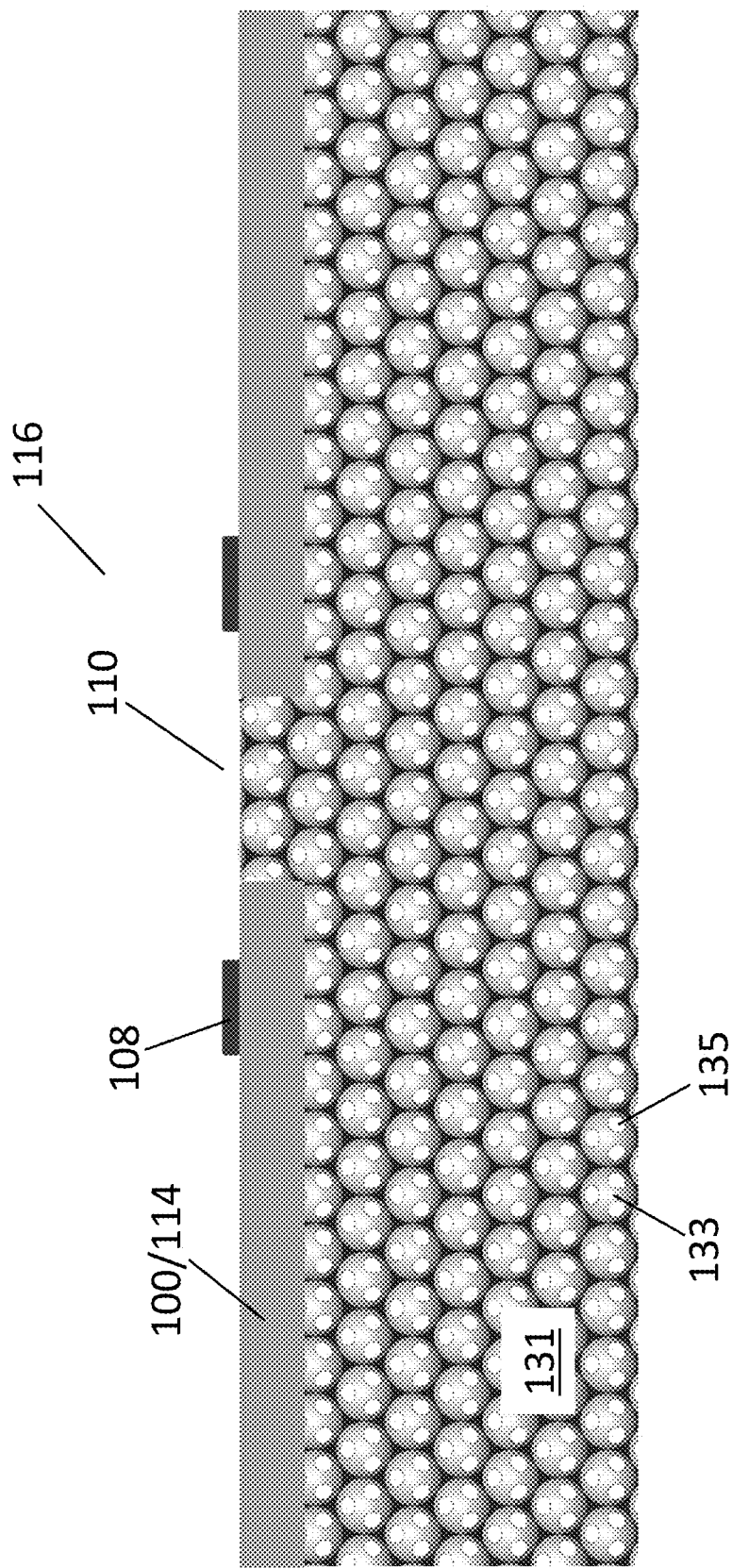

FIGS. 20A, 20B, 20C and 20D show profile views of illustrative embodiments. FIG. 20A shows an illustrative embodiment, where the inverse-opal structure is comprised of silica and is attached to the backside of a glass substrate (i.e. structure 100). In some embodiments, the inverse-opal structure is configured in close proximity to the vaporization ports 110 (see FIGS. 20A, 20B, 20C and 20D). FIG. 20B shows an illustrative embodiment where the at least a portion of the inverse-opal wick 131 is configured to at least partially reside in the vaporization ports 110.

Figure 20C:
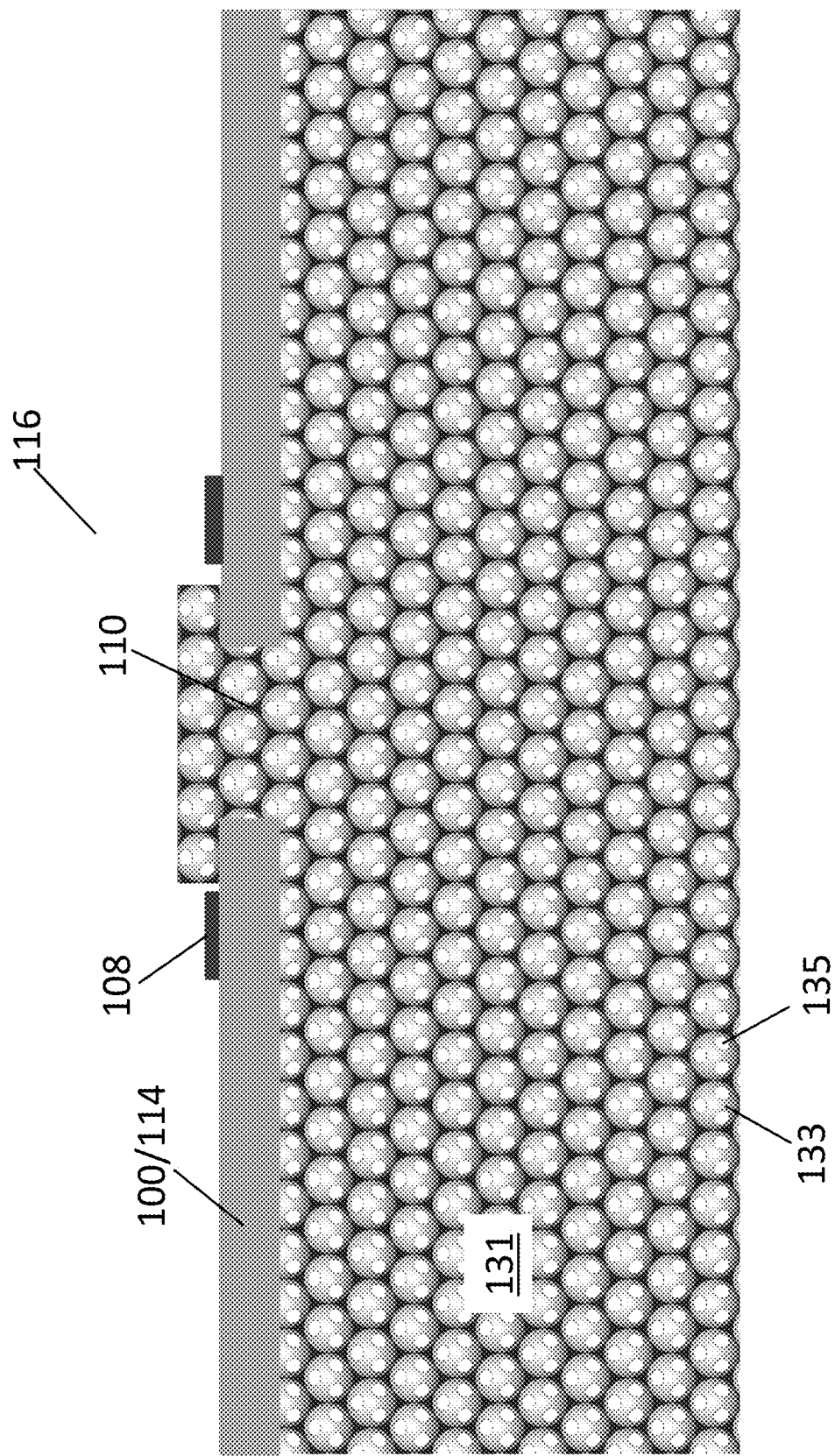

FIG. 20C shows an illustrative embodiment where the inverse-opal wick 131 is configured to reside in the vaporization ports 110, and to reside on both the back-side and front-side of the substrate (i.e. structure 100). The top portion of wick 131 could optionally coated with a hydrophobic material, which could prevent hydrophilic liquids from leaking through the vaporization port 110. Another advantage to the illustrative embodiment shown in FIG. 20C is that by positioning at least part of the wick above structure 100, wick 131 can be mechanically attached to structure 100, in addition to being bonded to structure 100.

Figure 20D:
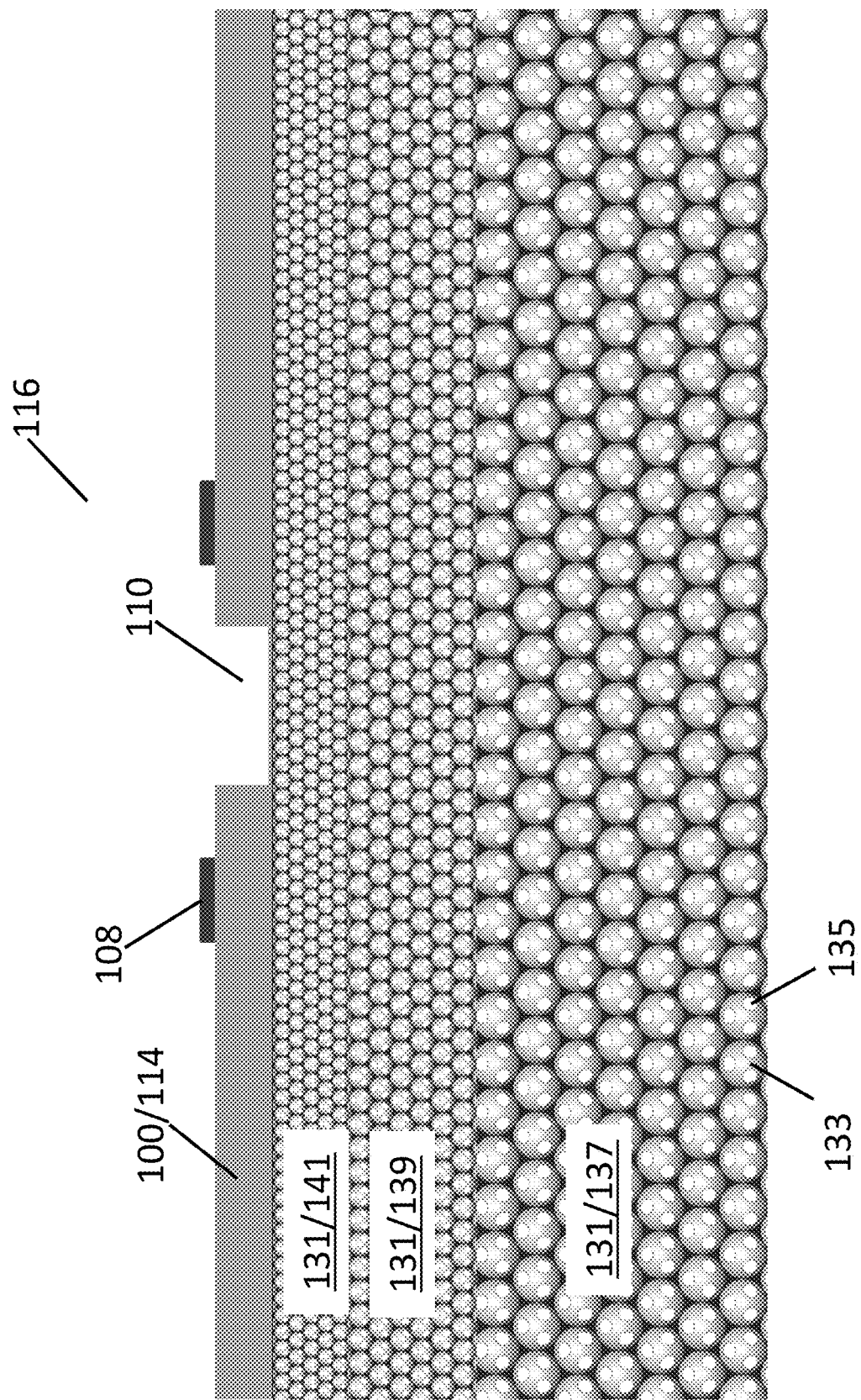

FIG. 20D shows an illustrative embodiment where the inverse opal wick 131 is fabricated with predetermined size pores, as a result of using different size template structures at different spatial locations. In this illustrative embodiment, larger template structures 137 are used away from structure 100 to allow provide larger permeability for more efficient viscous fluid flow. Smaller template structures 141 are positioned adjacent to structure 100, to provide larger Laplace pressure in these regions, and thereby enhancing capillary action during vaporization. In this illustrative embodiment, mesoscale template structures 139 are positioned between large template structures 137 and small template structures 141.

In some embodiments, large template structures 137, mesoscale template structures 139, and small template structures 141 can be comprised from different sizes particles 130. Two, three or more different size template structures can be used in a plurality of regions, depending upon the application, and desired wick performance.

In some embodiments, large template structures 137 can be used in regions where significant vapor transport may occur. Since vapor has a density much lower than liquid, the viscous losses per unit mass transported may be large, and larger structures may be advantageous.

In some embodiments, the inverse-opal structure can be used as a standalone wick and not directly attached to any other structure or substrate.

In some embodiments, silica-based inverse-opal structures can provide very efficient wicking to structure 100 and vaporization port 110. In some embodiments, silica-based inverse-opal structures can provide structural support for structure 100 and thin structural region 114.

In some embodiments, silica-based inverse-opal structures can be made very hydrophilic or hydrophobic by cleaning or treating the surface with surface coating 128 (see FIGS. 14B and 14C.

In some embodiments, the geometry of the wick 131: (1) can be configured to be substantially uniform in three orthogonal directions, (2) can be configured to be substantially different in one direction compared to the other two orthogonal directions, or (3) configured to be substantially different in all three directions. In some embodiments, it may be advantageous to have a substantially higher permeability, to provide more efficient viscous flow, in one or more preferred directions. In some embodiments, it may be advantageous to have a substantially higher surface area, to provide more significant capillary pressure, in one or more preferred directions.

Figure 21A:
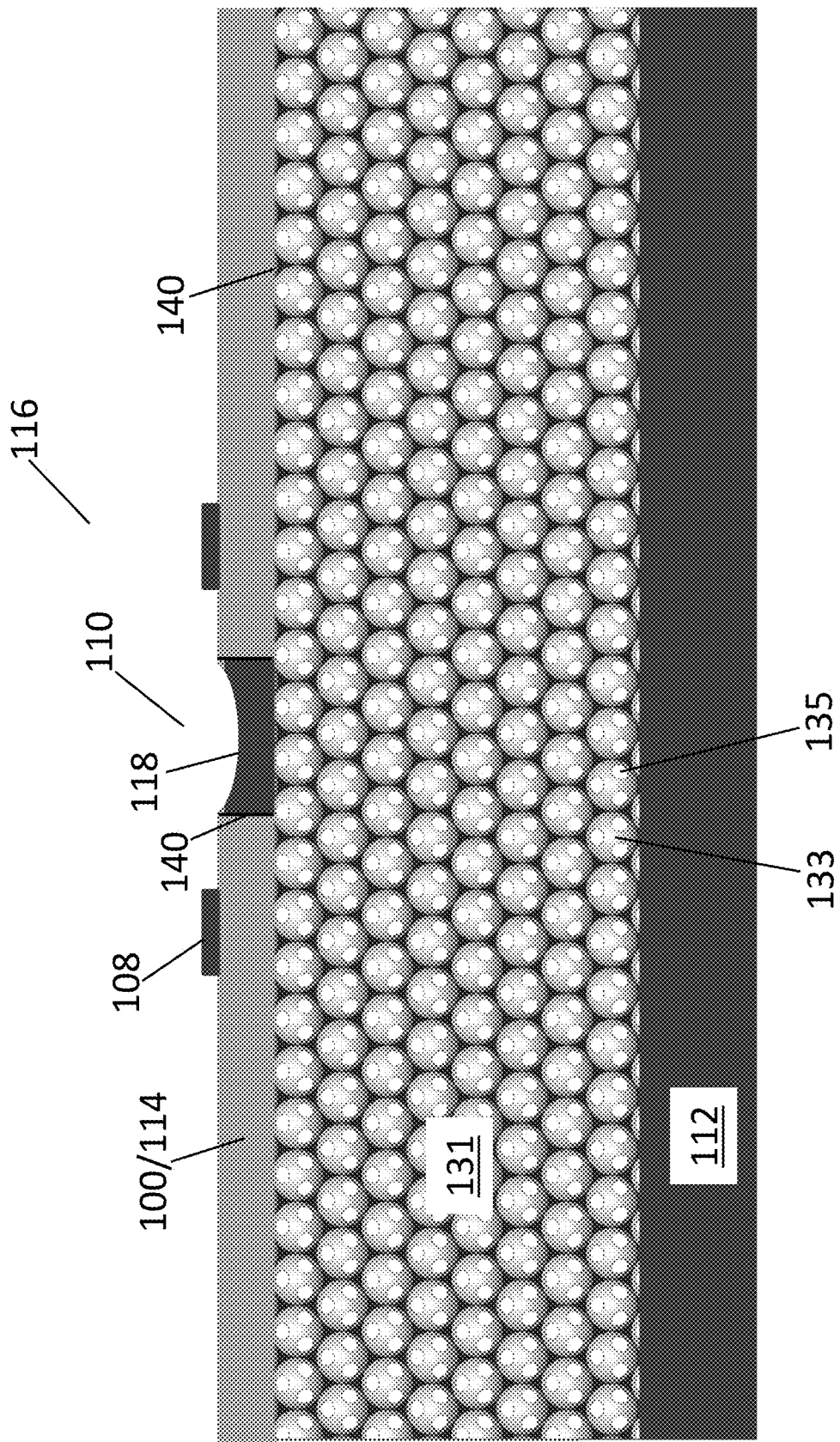
FIGS. 21A and 21B show profile views of the apparatus depicting the major components of an illustrative embodiments.
Figure 21B:
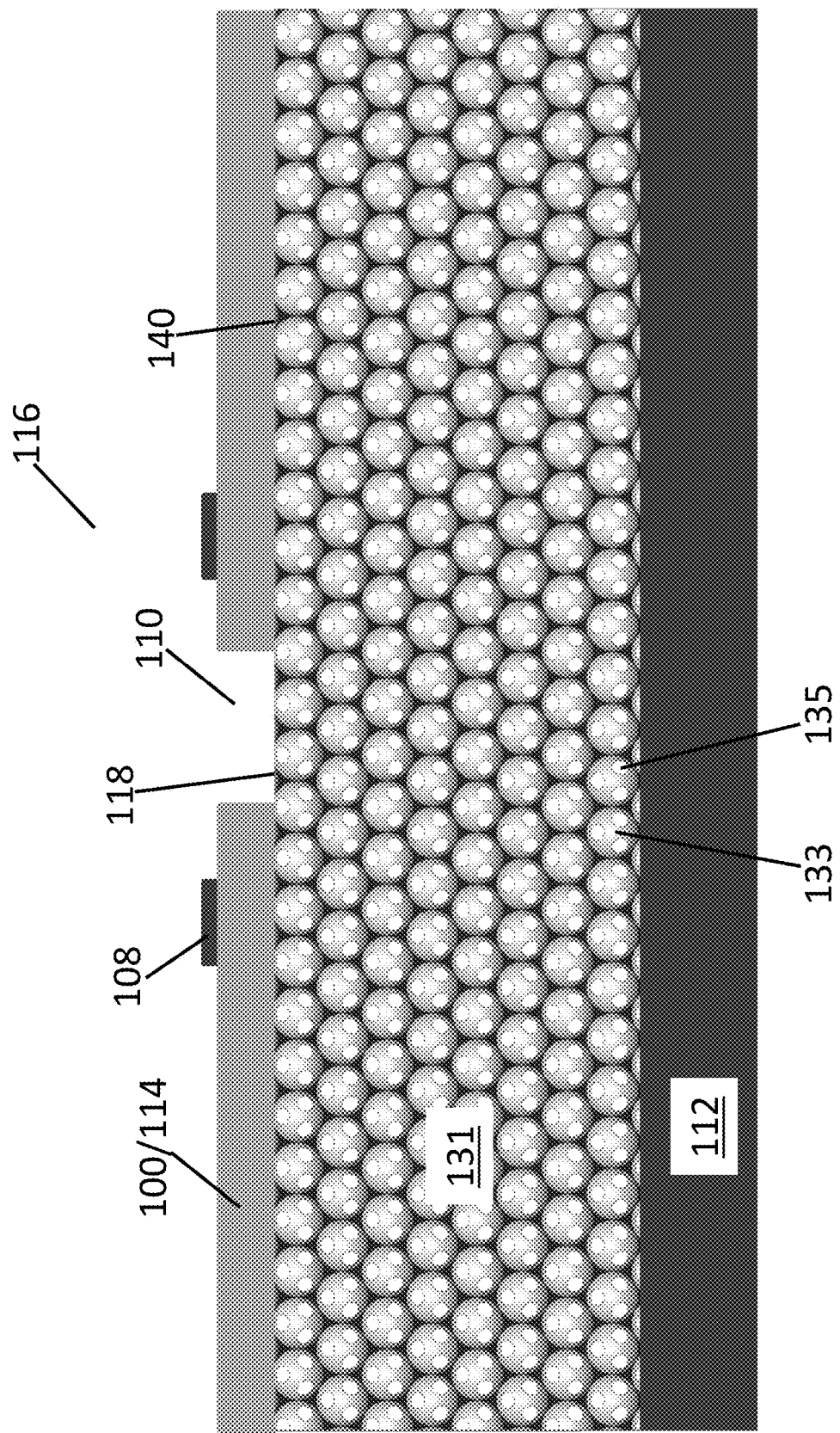

FIGS. 21A and 21B show profile views of illustrative embodiments. The surrounding environment 116 is above the structure 100. In an illustrative embodiment, thin structural region 114 coincides with structure 100. A vaporization port 110 is formed in the structure 100 and is in fluid communication with the liquid source 112 region and the surrounding environment 116. A heating element 108 is in close proximity to vaporization port 110. In an illustrative embodiment, heating element 108 could be located within 5-100 um (or 0.5 um to 1 mm) of vaporization port 110. In an illustrative embodiment, heating element 108 is located within 0.5-1000 um. Meniscus 118 defines the vapor and liquid interface. A thin structural region 114 can be formed in structure 100. In some embodiments, structure 100 is the thin structural region 114. Contact area 140 is formed between the liquid in wick 131 and the thin structural region 114.

In some embodiments, vaporization port 110 is formed by wet etching a through-hole in structure 100. Wet etching can be highly scalable, relatively inexpensive, and provides micro-scale roughened surfaces. In some embodiments, a wet etching process could consist hydrofluoric acid etching of a glass substrate. The wet etching process can cause surface roughness that ranges in characteristic size from sub-micron to several microns. In some embodiments, this surface roughness combined with a hydrophilic glass surface can provide a super hydrophilic surface, which can be highly wettable by a hydrophilic liquid.

In some embodiments, surface roughness resulting from wet etching combined with a hydrophobic-treated glass surface can provide a super hydrophobic surface, which can be highly wettable by a hydrophobic liquid.

In some embodiments the thin structural region 114 is adjacent to the vaporization ports 110 and the heating elements 108, which could minimize parasitic heat transfer. In some embodiments meniscus 118, which separates the liquid in the vaporization port and the surrounding environment, could have curvature, which could create a difference in pressure between the liquid in wick 131, and the surrounding environment 116. In some embodiments, there is significant contact surface area 140 between the thin structural region 114 and the liquid contained in a vaporization port 110 and the liquid contained in wick 131. A large contact area 140 can be advantageous, as it can provide efficient transport of thermal energy from structure 100 to the liquid, compared to a small contact area.

FIG. 21A shows a profile view where meniscus 118 is located in vaporization port 110. FIG. 21B shows a profile view where meniscus 118 is located within wick 131, which is adjacent or in close proximity to vaporization port 110. In some embodiments, under sufficiently high vaporization mass flux, meniscus 118 can retreat from the vaporization port 110 into wicking structure 131, due to an increase in the pressure gradient resulting from viscous losses in the liquid and vapor phases. In some embodiments, during sufficiently high vaporization mass flux, nucleic boiling of the vaporization liquid can occur and meniscus 118 can retreat from the vaporization port 110 and from structure 100, and retreat into wick 131. If the pore size of wick 131 is smaller than the characteristic dimension of vaporization port 110, and if meniscus 118 retreats into wick 131, the Laplace pressure can increase and the capillary action can be more significant, which could increase the mass flux being vaporized. By controlling the characterize dimensions of the vaporization port 110 and the inverse opal wick 131 in the vicinity of the port 110, the vaporization apparatus can be designed to be self-regulating, and have increased stability during the vaporization process. In some embodiments, this self-regulating mechanism can substantially reduce dryout and avoid undesirably high temperatures during the vaporization process, especially at very high mass flux conditions.

In some embodiments, the inverse-opal structure could comprise a large surface area 140 between the liquid and the solid, which could help provide a thermal conduction pathway to preheat the liquid and could enhance liquid/solid vaporization. In some embodiments, the thermal conduction pathway can be optimized by predetermining the dimensions and materials used in the inverse-opal wick 131.

Inverse opal structures can be made relatively porous, with porosity of approximately 80-90%. The thermal conductivity of glass is relatively low, is $k_g$=1.05 W/(m K), compared to many other solid materials, and is especially low compared to metals, such as copper (which can have a relatively high thermal conductivity of approximately $k_g$=385 W/(m K)). If the thermal conductivity of glass is $k_g$=1.05 W/(m K), and the inverse opal structure is, for example, 20% glass, the effective thermal conductivity of the silica inverse opal wick would be approximately $k_{wick}$=0.21 (W/(m K)), which is relatively low for most solid structures, and comparable to liquids such as glycerin. Therefore, a silica inverse opal wick is well matched to wicking liquids such as glycerin, while minimizing parasitic heat losses, that could otherwise limit thermal dynamic efficiency of the vaporization apparatus. In some embodiments, using metal inverse opals, such as copper inverse opals, could increase parasitic heat losses, and could decrease thermal dynamic efficiency of the vaporization apparatus, and could therefore be undesirable.

In some embodiments, the surface of silica inverse opals can be chemically treated to make them very hydrophilic in predetermined regions, and very hydrophobic in other predetermined regions. This can provide significant control of how the liquid wets the wick, and can prevent undesirable leaking of liquid out of the vaporization structure. In some embodiments, there can be significantly more control over hydrophilicity and hydrophobicity for silica inverse opal wicks, compared to metal inverse opal wicks, such as copper inverse opal wicks.

In some illustrative embodiments, an inverse-opal structure (open-celled glass or metal foam) forms wick 131, located in part of the liquid source region 112 or in contact with a wick that is in communication with liquid source region 112, and located in close proximity to the vaporization port 110, and at least in the region adjacent to the vaporization port 110. In some illustrative embodiments, an inverse opal structure is attached to structure 100 (i.e. attached to the substrate), which provides fluid communication between the liquid source 112 wick and the substrate.

In some embodiments, inverse-opal wick 131 is attached to structure 100 and provides structural mechanical support of structure 100. In some embodiments, inverse-opal wick 131 is attached to thin structural region 114 and provides structural mechanical support of thin structural region 114.

In an embodiment, the inverse-opal wick 131 may be hydrophilic. In an embodiment, the inverse-opal wick 131 may be hydrophobic, or may be a hydrophilic/hydrophobic combination. In an embodiment, hydrophilic inverse-opal wick 131 may be formed from glass or other materials. In an embodiment, the characteristic cell size of the inverse-opal wick 131 could range in size from ten nanometers to 10 millimeters. In an embodiment, the characteristic cell size of the inverse-opal wick 131 could range in size from 1 micrometer to 1 millimeter. In an embodiment, the characteristic cell size of the inverse-opal wick 131 could range in size from 10 micrometers to 300 micrometers. In some embodiments, the characteristic cell size of the inverse-opal wick 131 could be judiciously chosen to vary in different spatial locations to achieve desired performance. For example, in some embodiments, large cell sizes may be chosen in certain regions to reduce viscous losses, while smaller cells sizes may be chosen in certain regions to increase Laplace pressure through capillary action. In some embodiments, large cell sizes may be chosen for a large region of the wick to reduce viscous losses, while smaller cells sizes may be chosen near the vaporization region, where the meniscus is likely to exist to increase Laplace pressure through capillary action. The judicious choice of inverse opal cell size can significantly improve mass transfer vaporization material through the structure and achieve very high performance.

In some embodiments, the microfabricated inverse opal wick 131 can provide fluid communication between a standard off-the-shelf-type wicking structure (for example, a silica fiber wick) and structure 100. The inverse opal wick can have a three dimensional (i.e. rough) interface surface that can provide good fluid communication to a standard off-the-shelf-type wick.

In an illustrative embodiment, the highly porous cross-linked networked structure of inverse opal wick 131 can be designed to be sufficiently large in volume so as to contain enough liquid material such that a predetermined mass of liquid can be vaporized during a predetermined time duration. By containing a predetermined and sufficient mass of liquid in close proximity to structure 100, a significantly large mass of liquid can be vaporized is a relatively short period of time.

The mass of liquid vaporized and the time duration of vaporization can vary significantly, and can be predetermined to meet requirements of particular application and/or desired performance. For example, in an illustrative embodiment, 3 mg of liquid can be vaporized within 3 seconds of time. In an illustrative embodiment, 5 mg of liquid can be vaporized within 3 seconds of time. In an illustrative embodiment, 10 mg of liquid or more can be vaporized within 3 seconds of time. In an illustrative embodiment, the mass of liquid could be as little as say 0.1 mg or less, and as high as 100 mg or higher. In an illustrative embodiment, the time duration during evaporation could be as little as 1 ms or as large as a few minutes or more.

In some embodiments, the highly cross-linked network structure of inverse opal wick 131, can provide for efficient viscous flow in directions both perpendicular to structure 100, and parallel to structure 100. Referring to FIGS. 17A, 17B and 17C, vaporization sectors 107 may be individually/selectively addressed. In an illustrative embodiment, for a particular time segment, a single vaporization sector, such as 107a, may be electrically energized. During vaporization, a significant mass flux of liquid may be vaporized through vaporization ports 110 (see FIGS. 18A, 18B, 18C and 18D) that are associated with vaporization sector 107a. Efficient viscous flow in both the perpendicular and parallel directions, can provide a significant mass transport of liquid from the surrounding regions to the area surrounding energized vaporization sector 107a, which can facilitate significant vaporization mass flux, and help reduce potential dryout and excessive temperatures.

In an illustrative embodiment, at a particular subsequent time segment, a different single vaporization sector, say vaporization sector 107b, could be electrically energized, which could cause significant mass flux of liquid to be vaporized in that region. Efficient viscous flow in both the perpendicular and parallel directions, can then provide a significant mass transport of liquid from the surrounding regions to the area surrounding now energized vaporization sector 107b, which can facilitate significant vaporization mass flux, and help reduce potential dryout and excessive temperatures.

In some embodiments, efficient viscous flow in both the perpendicular and parallel directions provides a mechanism to balance the liquid mass distribution for the overall vaporization apparatus, while minimizing potential dryout and excessive temperatures.

In some embodiments of inverse opal wick 131, for a given sacrificial template particle size, there can be two characteristic pore sizes: larger pore 133 and smaller pore 135 (see FIGS. 19C and 19D). The larger pore 133 can exhibit a larger permeability, which can provide for more efficient viscous fluid transport. The smaller pore 135 can exhibit higher Laplace pressure, due to the small length scales and sharp geometric features associated with smaller pore 135, which can pin meniscus 118 at smaller pore 135 (referring to FIG. 21B).

In an inverse opal wick, there are two characteristic pore sizes with two statistical mode peaks: a larger pore 133 and a smaller pore 135, which yields two characteristic Laplace pressures. If an adverse pressure is applied that is greater than the Laplace pressure associated with larger pore 133, but smaller than the Laplace pressure associate with smaller pore 135, then a diode-like and/or ratcheting effect can be observed. In this pressure range, if the meniscus occupies larger pore 133, it can retreat and become pinned in smaller pore 135, and no longer retreat, creating a diode-like behavior. Since the pores in an inverse opal wick are distributed in a periodic manner, the meniscus can be pinned at periodic locations, where smaller pores 135 are located, creating a ratcheting effect.

In an illustrative embodiment, during cyclic vaporization, the periodic structure of inverse opal wick 131 can produce a diode-like and/or ratcheting effect on fluid motion in the wick. For example, during vaporization there can be a relatively large Laplace pressure difference across meniscus 118, that can cause the meniscus to retreat and be pinned at smaller pore 135. When vaporization is no longer active, the efficient viscous fluid transport associated with the larger pore 133, and coupled with the wettability of the wick surface, could allow for the meniscus to advance towards structure 100, and potentially to further advance into vaporization port 110.

In an illustrative embodiment, vaporization sectors 107 can be individually/selectively addressable and can be energized in a cyclic manner for a predetermined period of time. The process of cyclically energizing vaporization sectors 107 and in combination with the diode-like and/or ratcheting behavior of inverse opal wick 131 provides an efficient fluid transport mechanism during sequential vaporization processes, and can lead to high-performance vaporization while minimizing potential for dryout and minimized excessively high temperatures.

Figure 22A:
FIGS. 22A and 22B shows an example of microfabrication process flow for device fabrication for an illustrative embodiment.
Figure 22B:
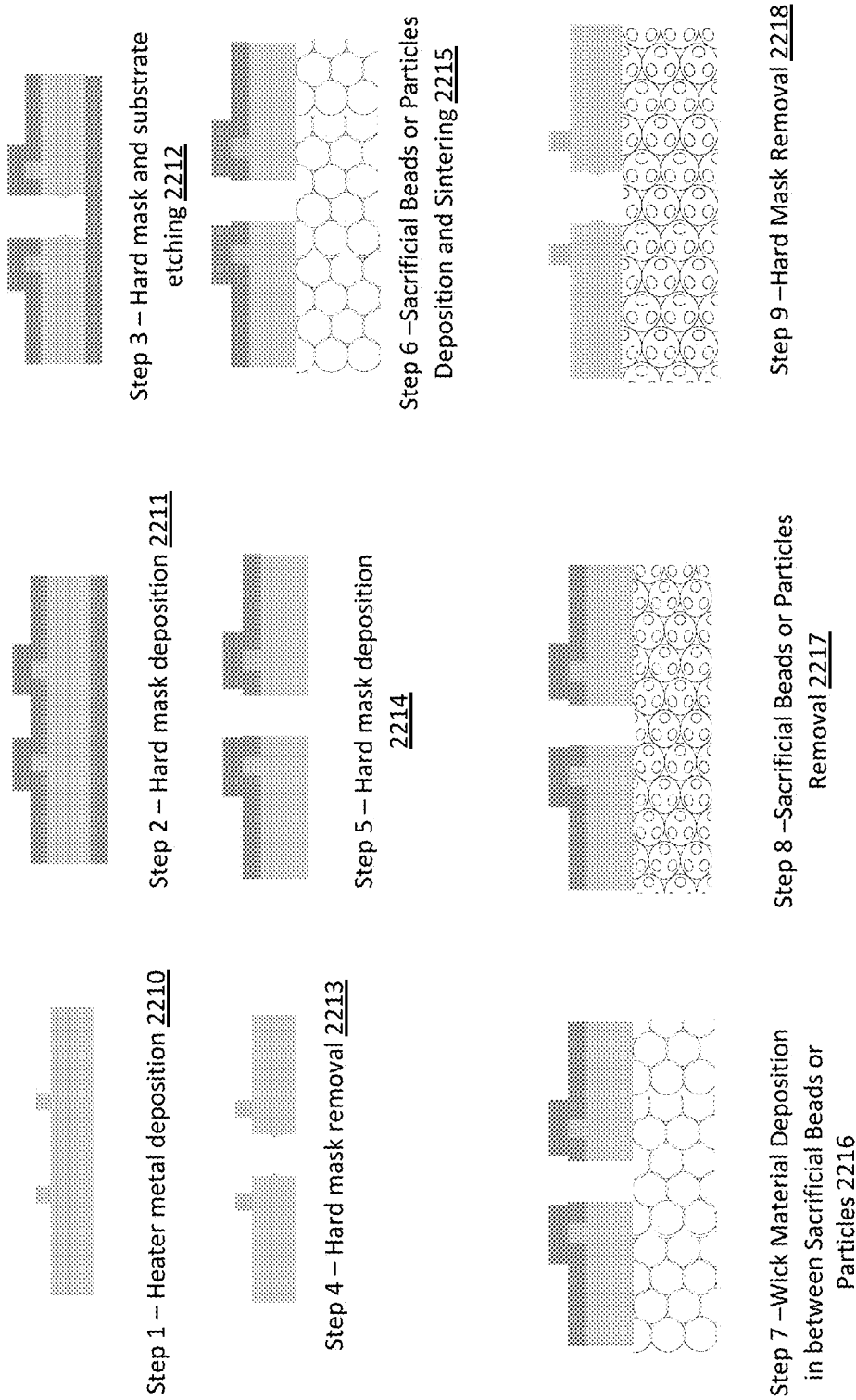

FIGS. 22A and 22B show examples for microfabrication process flows for device fabrication for an embodiment, which consists of four and nine processing steps using a single structure, respectively. FIG. 22A shows a microfabrication process for an illustrative embodiment, the structure 100 could be made from a 100 μm thick glass substrate from Schott (D263T-eco, AF32-eco or MEMpax). The glass substrate could be formed from a variety of materials and thicknesses ranging from 1 um to 10 mm. A photoresist could be patterned and metal (for example, titanium and platinum) could be deposited for the electrode leads and heating elements (Step 1—Heater metal deposition 2110). After photoresist and metal liftoff, a hard mask film (for example, chromium/gold, aluminum or amorphous silicon) could be deposited on both sides of the substrate (Step 2—Hard mask deposition 2111). On the backside, photoresist could be patterned and the hard mask could be etched (wet or dry) followed by the glass being optionally wet etched down to roughly half the substrate thickness (Step 3—Backside hard mask and glass etching 2212). On the frontside, the vaporization port 110 could be patterned in close proximity (which could range between 5 um to 100 um, or 0.5 um to 1 mm) to the heater element 108 and a hard mask could be etched, followed by optional wet etching of the glass. At the same time, the backside could optionally be further etched since it could optionally be exposed, and a via (or through hole) could be created (Step 4—Topside hard mask and glass etching 2213). This could allow the vaporization port 110 to be in fluid communication with the liquid source 112 and the surrounding environment 116. Finally, the hard mask could be removed from both sides, and the substrate could then be diced (Step 4—Hard mask removal 2214).

A variety of nanofabrication and microfabrication equipment could be used to fabricate some embodiments of the vaporization device. The fabrication may include numerous deposition tools such as electron beam deposition, which could be used for the heating element, and plasma enhanced chemical vapor deposition (PECVD), which could be used to deposit the hard masks. In some embodiments, wet chemistry benches could be used for a variety of etch chemistries, including hydrofluoric acid etching of glass. Dry etching could also be used for isotropic etches in certain materials such as inductively coupled plasma reactive ion etching (ICP-RIE). Furthermore, in some embodiments, a photolithography mask aligner capable of backside alignment, such as the SUSS MA-6, could be used to pattern and align the features from front to back.

The fabrication process could use 100 um, 300 um, or even 500 um thick glass substrates to form structure 100. Embodiments could use 1 um to 10 mm thick substrates for thin structural region 114, and the substrates could encompass a variety of materials, such as glass, titanium, aluminum, sapphire, silicon carbide, diamond, ceramics, metals, silicon, and the like.

In one embodiment, after photoresist and metal liftoff, a hard mask film could be deposited on both sides of the thin substrate (Step 2—Hard mask deposition 2211) and the thick substrate. Photoresist could be patterned on both sides of the substrates to expose regions adjacent to the heating element on the thin substrate and the thick substrate. The hard masks could be etched, followed by the substrates being etched down to half the thickness of the substrates on each side, creating a through hole (i.e. a via through the chip) (Step 3—Hard mask and substrate etching 2212), which could provide fluid communication for the vaporization port 110 with the liquid source 112 and fluid communication with the surrounding environment 116.

In this embodiment, the hard mask could then be removed from both sides of the substrates (Step 4—Hard mask removal 2213). Depending on the bonding technique, an adhesion layer could optionally be deposited either on the back side of the thin substrate, the top side of the thick substrate, both, or neither.

FIG. 22B shows an example for microfabrication process flows for device fabrication for an embodiment that comprises a microfabricated inverse opal wick 131. In this exemplary embodiment, an additional 5 steps are incorporated. A hard mask film (for example, chromium/gold, aluminum or amorphous silicon) could be deposited on predetermined regions on the top side of the substrate (Step 5—Hard mask deposition 2214). The hard mask film can optionally be deposited in vaporization port 110, and optionally on predetermined regions on the backside of the substrate (not shown in Step 5—Hard mask deposition 2214, FIG. 22B).

Sacrificial template beads or particles 130 can be deposited on the backside of the substrate (Step 6—Sacrificial Beads or Particles Deposition and Sintering 2215). The beads can be spherical or other shape, comprised of a number of materials, including polystyrene, PMMA, PDMS, and others, and can range in size from 10 nm-10 mm. In some embodiments, polystyrene beads are used that range in size from 1-500 μm. In some embodiments, polystyrene beads are used that range in size of 20 um-300 μm. The beads can be purchased commercially, or can be fabricated using an emulsion polymerization method. In some embodiments, a solution of polystyrene beads is deposited on the backside of the substrate. The solvent is evaporated, leaving the polystyrene beads in a closed-packed configuration (such as a face-centered-cube or hexagonal-centered-cube).

In some embodiments, the sacrificial template beads or particles 130 can be deposited from a well-controlled flow. For example, in some embodiments, a solution containing the sacrificial particles 130 can be made to flow toward structure 100, and allowed to flow through the through-holes that form vaporization ports 110. The solvent can have a substantially uniform flow toward structure 100, due to a plurality of vaporization ports 110, while depositing a significant fraction of sacrificial template particles 130 in a closed-packed and repeatable arrangement onto structure 100. The solution flow can be driven be surface tension, gravity or by a prescribed pressure gradient.

In some embodiments, once sacrificial beads 130 are deposited, sacrificial beads 130 can then be heated to a moderate temperature (for example, 65° C.) to sinter the beads, without negatively affecting the previously fabricated electrodes. The temperature and duration of heating can be varied widely depending upon the size and type of particle, and the desired degree of sintering.

In some embodiments, wicking material is deposited in the interstitial region between the sintered beads or particles (Step 7—Wick material deposition in between sacrificial beads or particles 2216). A variety of materials can be deposited. In some embodiments, a metal seed layer is deposited on the backside of the substrate, and metal is electroplated in the interstitial region. Many metals can be electroplated, including nickel, copper, and many others. Metal oxides and metal alloys can also make suitable materials for inverse opal wicks.

In some embodiments, silica can be deposited in the interstitial regions. For example, a tetraethyl orthosilicate $Si(OC_2H_5)_4$(TEOS) (commercially available from Sigma-Aldrich) solution could be used as a precursor to deposit silica. In some embodiments, TEOS can be hydrolyzed to produce silica. Silica has the advantage in that it can bond directly to silica substrates, and its thermal expansion coefficient can be closely matched to glass-based substrates. In some embodiments, ethanol is used as a co-solvent that is miscible in both TEOS and water. In some embodiments, ammonium hydroxide or sodium hydroxide can be used as a basic catalyst to increases the reaction rate. In addition, a strong base can help chemically prepare surfaces to enhance covalent binding of deposited silica. In some embodiments, ammonium fluoride is a catalyst that can increase the reaction rate.

In some embodiments, the TEOS precursor solution can be transported to the template structure from a well-controlled flow. For example, in some embodiments, the solution (including TEOS, reactants and products) can be made to flow toward structure 100, and allowed to flow through the intestinal region between sacrificial beads 130, and through the through-holes that form vaporization ports 110. The solution can have a substantially uniform flow toward structure 100, due to a plurality of vaporization ports 110, therein depositing silica onto structure 100, onto sacrificial beads 130, and onto already deposited silica, thereby filling the interstitial region with silica. The highly cross-linked network structure of the interstitial region, provides a network of flow in which solution can flow through the template structure and through the through-holes that form vaporization ports 110, even when part of the wick is fully solidified with deposited silica. The solution flow can be driven be surface tension, gravity or by a prescribed pressure gradient.

In some embodiments, the sacrificial beads 130 can be removed (Step 8—Sacrificial Beads or Particles Removal 2217) leaving an inverse opal wick 131 attached to structure 100. The sacrificial beads 130 can be removed using a variety of solvents. For example, in some embodiments, toluene can be used to dissolve polystyrene beads, without adversely affecting other components on the apparatus. In some embodiments, the sacrificial beads 130 can be removed (Step 8—Sacrificial Beads or Particles Removal 2217) using calcination, thereby leaving an inverse opal wick 131 attached to structure 100.

Finally, the hard mask could be removed, and the substrate/wick combination can then be diced (Step 9—Hard mask removal 2218).

In some illustrative embodiments, the inverse opal structure could be heated, to a sufficiently high predetermined temperature or a predetermined time duration, so that it is annealed. In some embodiments, annealing the inverse opal structure could allow the structural walls to retract and become thicker and more structurally sound, which could reduce any potential splintering effects. In some embodiments, annealing could further open the porous cavities and provide more efficient fluid flow.

In some illustrative embodiments, the inverse opal structure can be chemically etched for a predetermined time duration. In some embodiments, chemically etching the inverse opal structure could allow thin structural walls to be removed, leaving the thicker and more structurally sound walls, which could reduce any potential splintering effects. In some embodiments, chemical etching could further open the porous cavities and provide more efficient fluid flow.

The inverse opal wick 131 can be fabricated by growing it layer by layer, it can be three dimensionally printed, and it can be formed by a number of self-assembling techniques.

Figure 23:
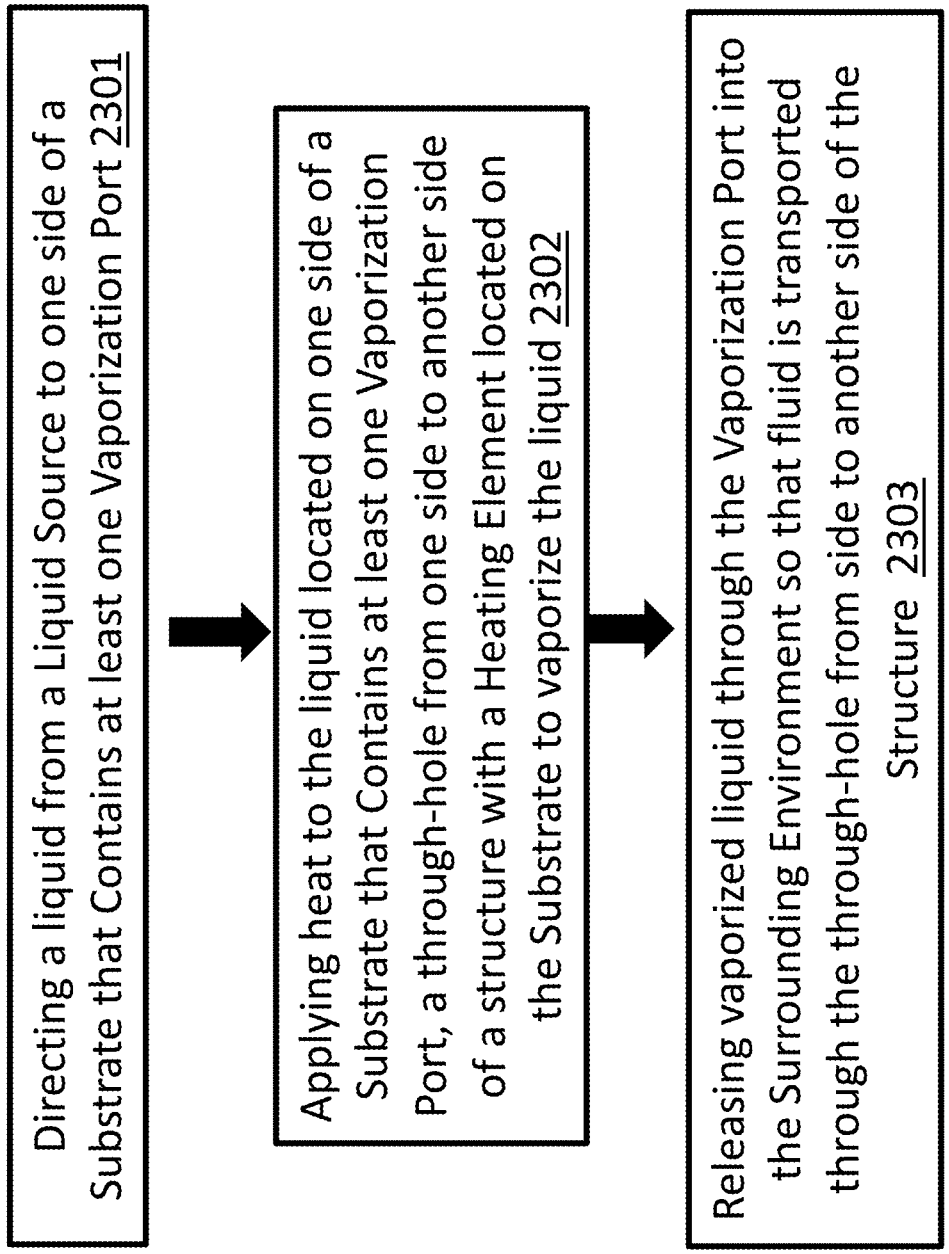
FIG. 23 shows a flowchart depicting a method of an illustrative embodiment.

FIG. 23 shows a flowchart depicting a method of an embodiment, which involves directing a liquid from a liquid source to one side of a substrate that contains at least one vaporization port, a through-hole from one side to another side of a structure, step 2301, and applying heat to the liquid located on one side of a substrate that contains at least one vaporization port with a heating element located on the substrate to vaporize the liquid, step 2302 (which could range between 5 μm to 100 μm, or 0.5 μm to 1 μm, or 0.5 μm to 500 μm in width). In an embodiment, the vaporized liquid is released through the vaporization port into the surrounding environment so that fluid is transported through the through-hole from one side to another side of the structure, step 2303.

In some embodiments, the vaporization port has lateral dimensions ranging from 10 μm-300 μm. In yet other embodiments, the vaporization port has lateral dimensions ranging from 1-1000 μm. Liquid could be introduced to the liquid source by directly placing the liquid in the liquid source or by an optional pump or an optional wicking structure wherein the liquid could be transported through capillary action to the liquid source. In an embodiment, electrical energy could be applied to the heating element, and the heating element could be heated through Joule heating (i.e. resistive heating). The thermal energy from the heating element could then be transferred to the thin structural region, which is adjacent to the vaporization port and liquid source. Heat could then be conducted locally into the liquid to heat the liquid to an optimal temperature for vaporization. This temperature could be well-controlled so that the liquid is heated sufficiently for vaporization, but does not reach an undesirably high temperature, which could cause undesirable chemical reactions or dryout the vaporization port. In addition, by controlling the electrical energy to the heating elements, the rate of vaporization or the total mass of vaporization can be accurately controlled. In some embodiments, the amount of electrical energy could be optionally varied, and optimized for the specific application. In yet other embodiments, an electrical waveform could be sinusoidal, square wave, or other waveform, which could be optimized for the specific application. In yet other embodiments, the waveform could pulse and cause vaporization, an aerosol or ejections of liquid droplets, and could decrease parasitic heat loss, thereby increasing thermodynamic efficiency.

Figure 24:
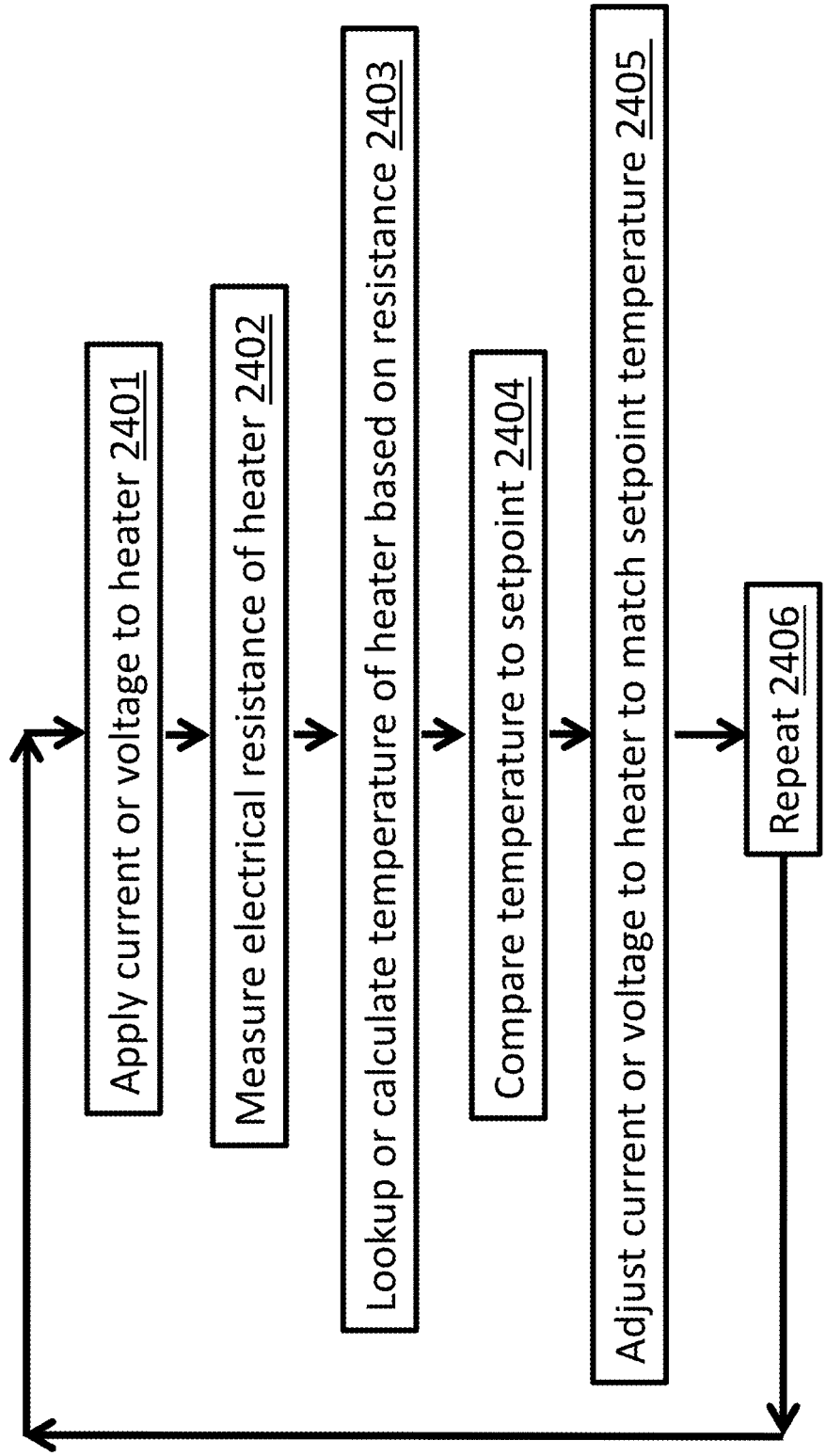
FIG. 24 shows a flowchart depicting a method of feedback control of an illustrative embodiment.

FIG. 24 depicts an illustrative embodiment of the control method to operate the vaporization apparatus (not shown in FIG. 24). The control method depicts a feedback loop to control the temperature of vaporization structure 100. The feedback loop may be cycled one or multiple times or in a continuous loop in order to maintain the temperature of vaporization structure 100. The control method is based on the adjustment of current or voltage supplied to vaporization structure 100 in order to control the temperature of vaporization structure while vaporization structure 100 is activated in order to produce vaporization of liquid or solid material.

In an illustrative embodiment, the cycle is comprised of the following events: First, current or voltage is applied to heater (Step 2401: Apply current or voltage to heater). Then the resistance of the heater is determined (Step 2402: Measure electrical resistance of heater). This measured resistance is then used to calculate or lookup the estimated temperature of the heater (Step 2403: Lookup or calculate temperature of heater based on resistance). The estimated heater temperature is then compared to a predetermined setpoint temperature (Step 2404: Compare temperature to setpoint). The current or voltage supplied to the heater is then adjusted to match the setpoint temperature (Step 2405: Adjust current or voltage to heater to match setpoint temperature). This cycle may then be repeated one or multiple times (Step 2406: Repeat).

In an illustrative embodiment, electrical power may be determined by multiplying the supplied voltage with the supplied current, $P=V \times I$. The electrical power can then be compared to a setpoint electrical power value. The supplied current or voltage can then be adjusted to match the supplied electrical power to the setpoint value. This cycle may be repeated, comprising a feedback loop such that vaporization structure 100 supplies a controlled amount of thermal power to the fluid to be vaporized.

Figure 25:
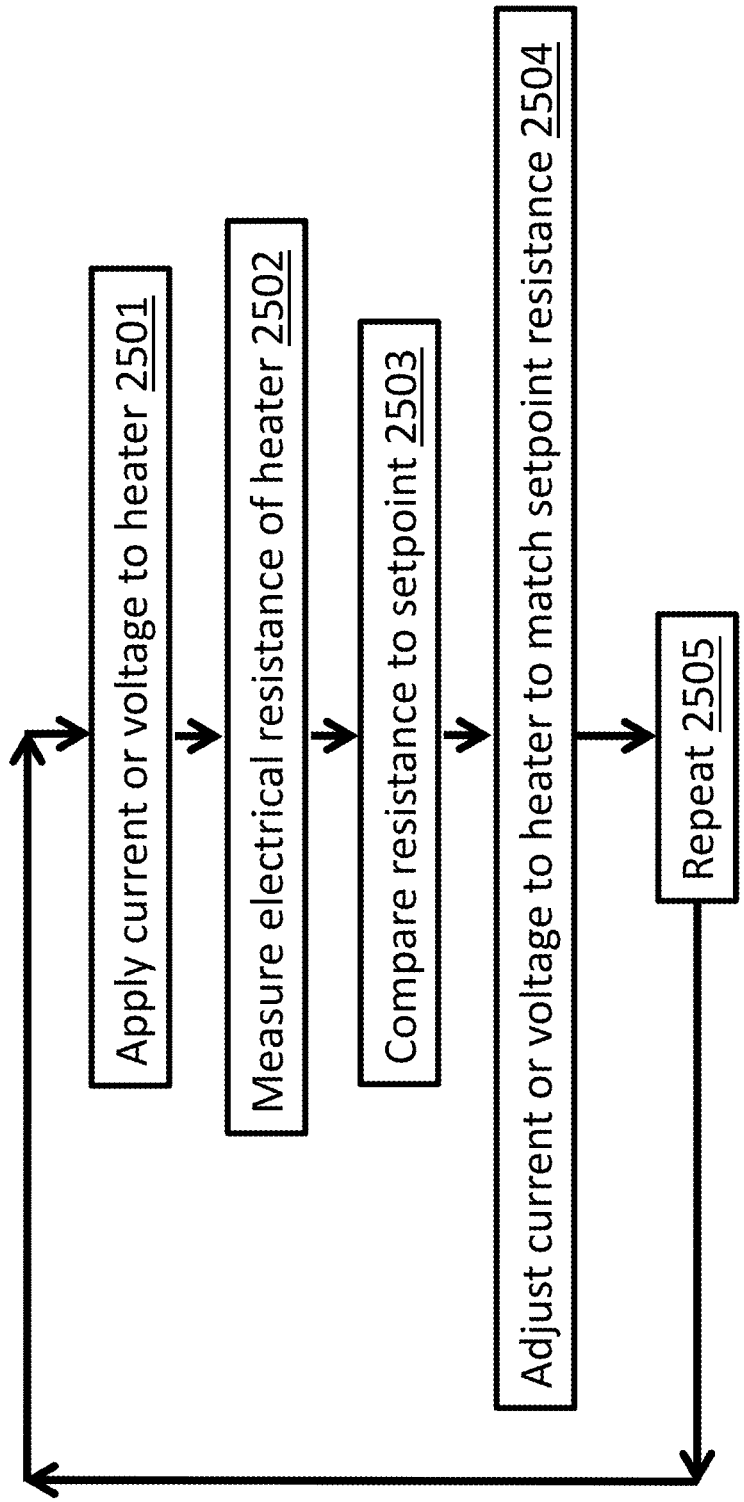
FIG. 25 shows a flowchart depicting a method of feedback control of an illustrative embodiment.

FIG. 25 depicts an illustrative embodiment of the control method to operate the vaporization structure 100. The control method depicts a feedback loop to control the temperature of vaporization structure 100. The feedback loop may be cycled one or multiple times or in a continuous loop in order to maintain the temperature of vaporization structure 100. The control method is based on the adjustment of current or voltage supplied to vaporization structure 100 in order to control the temperature of vaporization structure while vaporization structure 100 is activated in order to produce vaporization of liquid or solid/wax material.

In an illustrative embodiment, the cycle is comprised of the following events: First, current or voltage is applied to heater (Step 2501: Apply current or voltage to heater). Then the resistance of the heater is determined (Step 2502: Measure electrical resistance of heater). This resistance is then compared to setpoint resistance (Step 2503: Compare resistance to setpoint). The current or voltage supplied to the heater is then adjusted to match the setpoint resistance (Step 2504: Adjust current or voltage to heater to match setpoint resistance). This cycle may then be repeated one or multiple times (Step 2505: Repeat).

Figure 26:
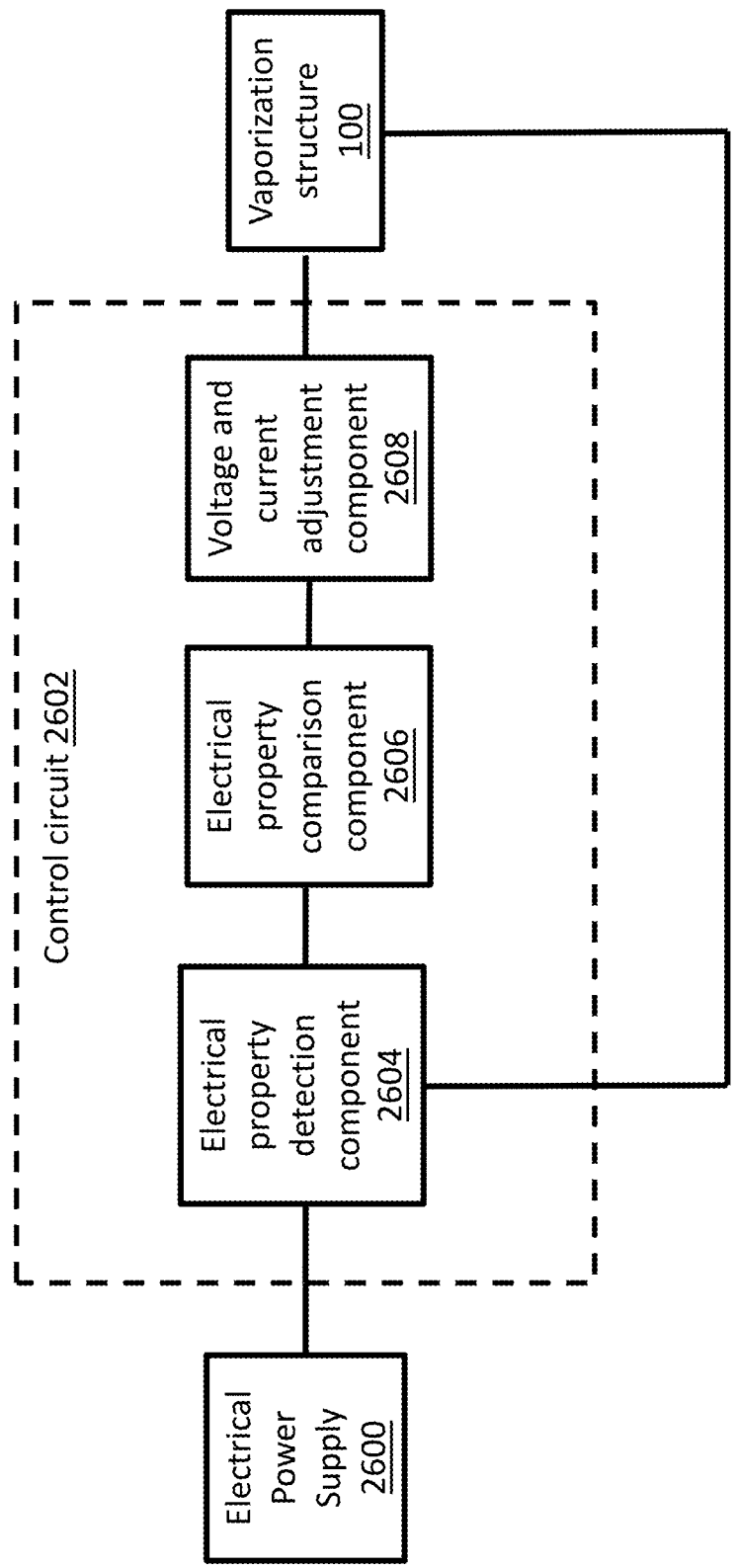
FIG. 26 shows a diagram depicting components of an electrical control circuit of an illustrative embodiment.

FIG. 26 depicts an illustrative embodiment of a control circuit 2602, which is used to operate vaporization structure 100. Electrical power source 2600 is in electrical communication with control circuit 2602. Control circuit 2602 is in electrical communication with vaporizing structure 100.

In an illustrative embodiment, control circuit 2602 is used to regulate the operating temperature or power of vaporizing structure 100 during operation. In an illustrative embodiment, control circuit 2602 is used to control/electrically energize vaporization sectors 107 (see FIGS. 17A, 17B and 17C).

In an illustrative embodiment, control circuit 2602 comprises an electrical property detection component 2604, and electrical property comparison component 2606 and a voltage and current adjustment component 2608. Electrical property detection component 2604 is used to determine the electrical characteristics of the electrical power supplied to vaporization structure 100. In an illustrative embodiment, electrical property detection component 2604 could determine the voltage and/or current of the electrical energy supplied to vaporization structure 100. In an illustrative embodiment, the determined voltage and power may be multiplied together to determine the electrical power supplied to vaporization structure 100.

In certain embodiments, electrical property detection component 2604 is directly connected to electrical power supply 2600, which allows it to analyze the state of electrical power supply 2600, but is not directly connected to vaporization structure 100 and does not monitor the electrical properties of vaporization structure 100.

In an illustrative embodiment, electrical property detection component 2604 may be comprised of an analog or digital circuit comprising any of the following devices: comparators, shunt resistors, hall effect sensors, voltage measurement devices, and the like.

In an illustrative embodiment, electrical property comparison component 2606 compares the electrical properties to a predetermined setpoint value. In some embodiments, more than one predetermined setpoint values may be used whereby each setpoint refers to a difference electrical characteristic.

In an illustrative embodiment, electrical property comparison component 2606 may be comprised of computerized control elements, analog comparators, digital comparators, and the like.

In an illustrative embodiment, voltage and current adjustment component 2608, adjusts the voltage and current supplied to vaporization structure 100 in order to cause the electrical operating characteristics of vaporization structure 100 to be equivalent to a predetermined setpoint value referred to in electrical property comparison component 2606. In some embodiments, more than one setpoint value may be used to adjust the electrical operating characteristics of vaporization structure 100.

In an illustrative embodiment, voltage and current adjustment component 2608, may be comprised of operational amplifiers, transistors such as BJTs or FETs, and the like.

In an illustrative embodiment, control circuit 2602 may be operated cyclically in a repeated fashion, whereby the process depicted in FIG. 26 is recurring multiple times during a single operation of vaporization structure 100.

In order to depict structural components of illustrative embodiments, heating elements 108 and electrode leads 106 as depicted in FIG. 5 are omitted from FIGS. 27A, 27B, 28A, 28B, 29A, 29B, 30A, 30B, and 32.

Figure 27A:
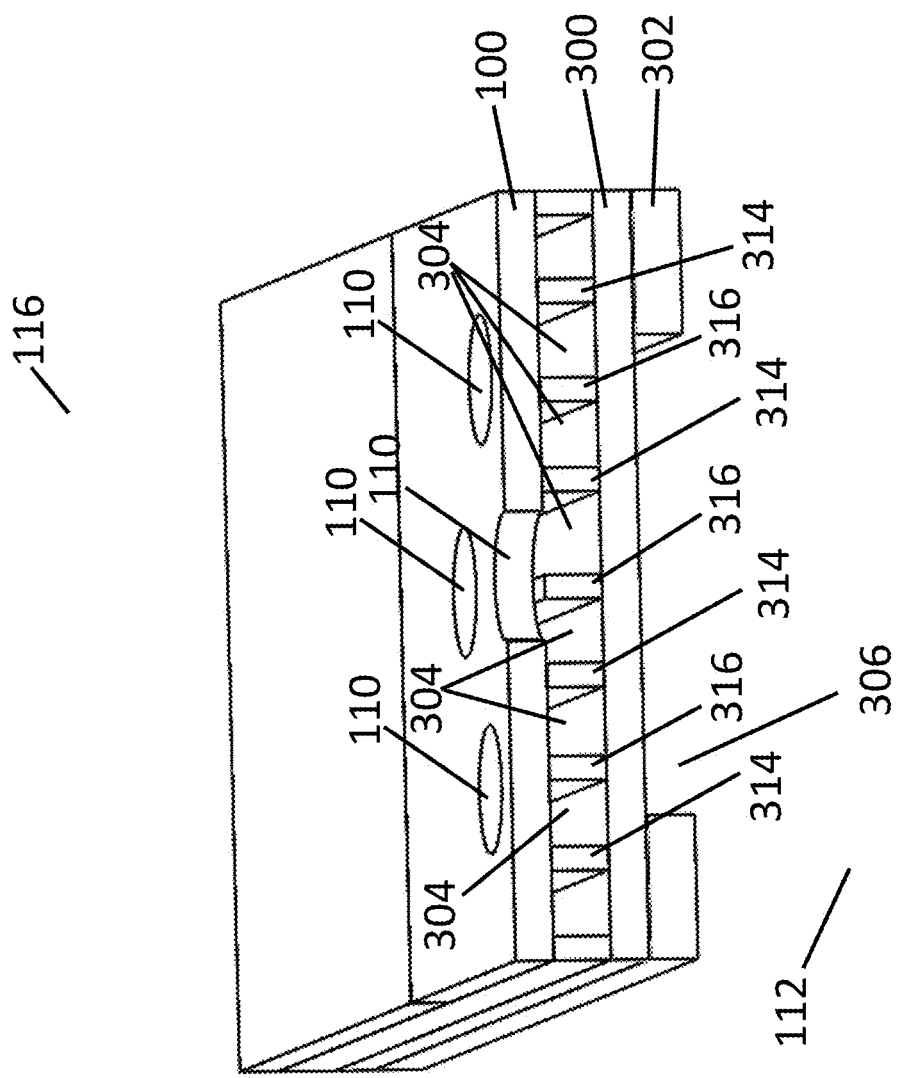
FIGS. 27A and 27B depict top and bottom views of an illustrative embodiment. The view is a cutaway to depict major components.

FIG. 27A depicts a top view of an illustrative embodiment, where three planar structural layers are interfaced together. Structure 100 is a planar structure and comprises heating element (note heating element 108 is shown in FIG. 5, but not shown here) in thermal communication with vaporization ports 110. Manifold 300, which can be a planar structure, interfaces to structure 100 and to manifold extension 302, which can also be a planar structure. In an illustrative embodiment, ridge 316 and ridge 314 are formed by etching structure 300. In an illustrative embodiment, ridge 314 and ridge 316 form flow channel 304. Flow channels 304 can be in fluid communication with vaporization ports 110. In an illustrative embodiment, opening 306 can be optionally formed by etching manifold extension 302.

In other embodiments, only two layers may be optionally used, such as structure 100 and manifold 300. In some embodiments, a third planar structural layer denoted as manifold extension 302 can be positioned between manifold 300 and liquid source 112. In some embodiments the apparatus is positioned so that the liquid source region 112 is positioned on one side the apparatus, and the surrounding environment 116 is on the opposite side, accessed by the vaporization ports.

In some embodiments, structure 100 is in planar contact with manifold 300. In some embodiments, manifold 300 is in planar contact with manifold extension 302. In some embodiments, planar contact can be defined as when two planar structures are positioned so that their respective planes are parallel and their respective large sides are in contact. In some embodiments, planar contact can be defined as when two planar structures are positioned so that their respective planes are parallel and their respective large sides are in close proximity to each other.

In some embodiments, structure 100, manifold 300, and manifold extension 302 can be formed by anisotropic etching glass using photo structural glass, such as FOTURAN®, manufactured by SCHOTT Corporation. In other embodiments, structure 100, manifold 300, and manifold extension 302 can be fabricated from plastic, silicon, titanium, metals, ceramics, PDMS, polymers, fiberglass, composites, or other materials.

In some embodiments, structure 100, manifold 300, and manifold extension 302 can be interfaced without bonding, whereby the structural layers are adhered together using stiction, electrostatic attraction, capillary forces, and the like. In some embodiments, structure 100, manifold 300, and manifold extension 302 can be interfaced by known bonding techniques, such as diffusion bonding, eutectic bonding, ambient temperature bonding, adhesive-based bonding, and the like. In some embodiments, structure 100, manifold 300, and manifold interface 302 can be interfaced by mechanical compression.

In some embodiments, ridges 31 or ridges 316 can be positioned to partially occlude vaporization ports 110. This partial occlusion can provide addition wetting surface area, which can enhance capillary action of the meniscus during the vaporization process. In some embodiments, the partial occlusion of the vaporization port 110 can provide a location for the meniscus to pin during the vaporization process.

Figure 27B:
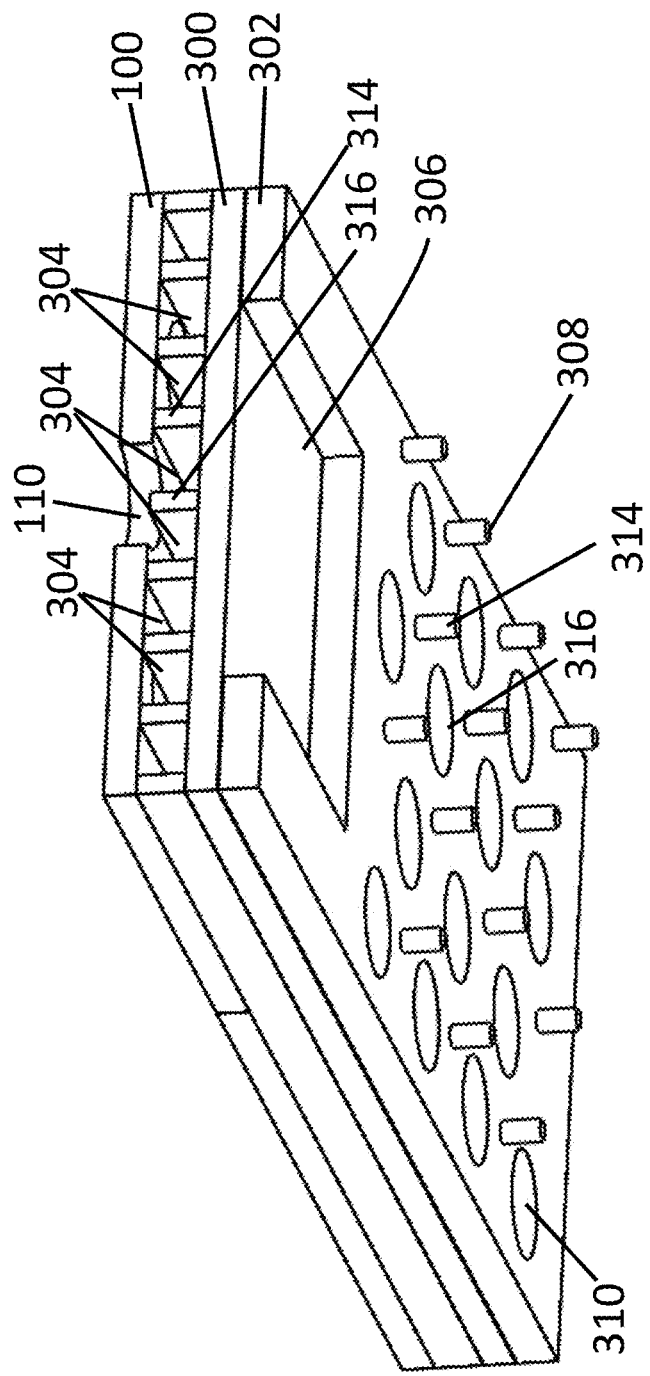

FIG. 27B depicts a bottom view of an illustrative embodiment, where three structure layers (structure 100, manifold 300, and manifold extension 302) are interfaced together. In an illustrative embodiment, ridge 316 is formed by etching structure 300, and ridge 314 is formed by etching manifold 300. Flow Channels 304 can be in fluid communication with vaporization ports 110. In an illustrative embodiment, opening 306 can be optionally formed by etching manifold extension 302.

In an illustrative embodiment, wicking pillars 308 can be formed in manifold extension 302. In an illustrative embodiment, liquid port 310 can be formed in manifold extension 302. Wicking pillars 308 and liquid port 310 are in fluid communication with liquid source region 112.

In some embodiments, structure 100 is a substantially planar structure. In some embodiments, vaporization ports 110 can be formed by making through-holes in structure 100. In some embodiments, vaporization ports 110 are substantially perpendicular to the plane of structure 100.

In some embodiments manifold 300 and manifold 302 can be formed from substantially planar structures. In some embodiments, liquid ports 310 can be formed by making through-holes in manifold extension 302. In some embodiments, liquid ports can also be formed by making through-holes in manifold 300. These through-holes can be substantially perpendicular to the plane of manifold 300 and manifold extension 302.

In some embodiments, opening 306 can be etched in manifold extension 302. The apparatus can be positioned so that liquid ports 310 are in fluid communication with liquid source region 112, and vaporization ports 110 are in fluid communication with surrounding environment 116.

Figure 28A:
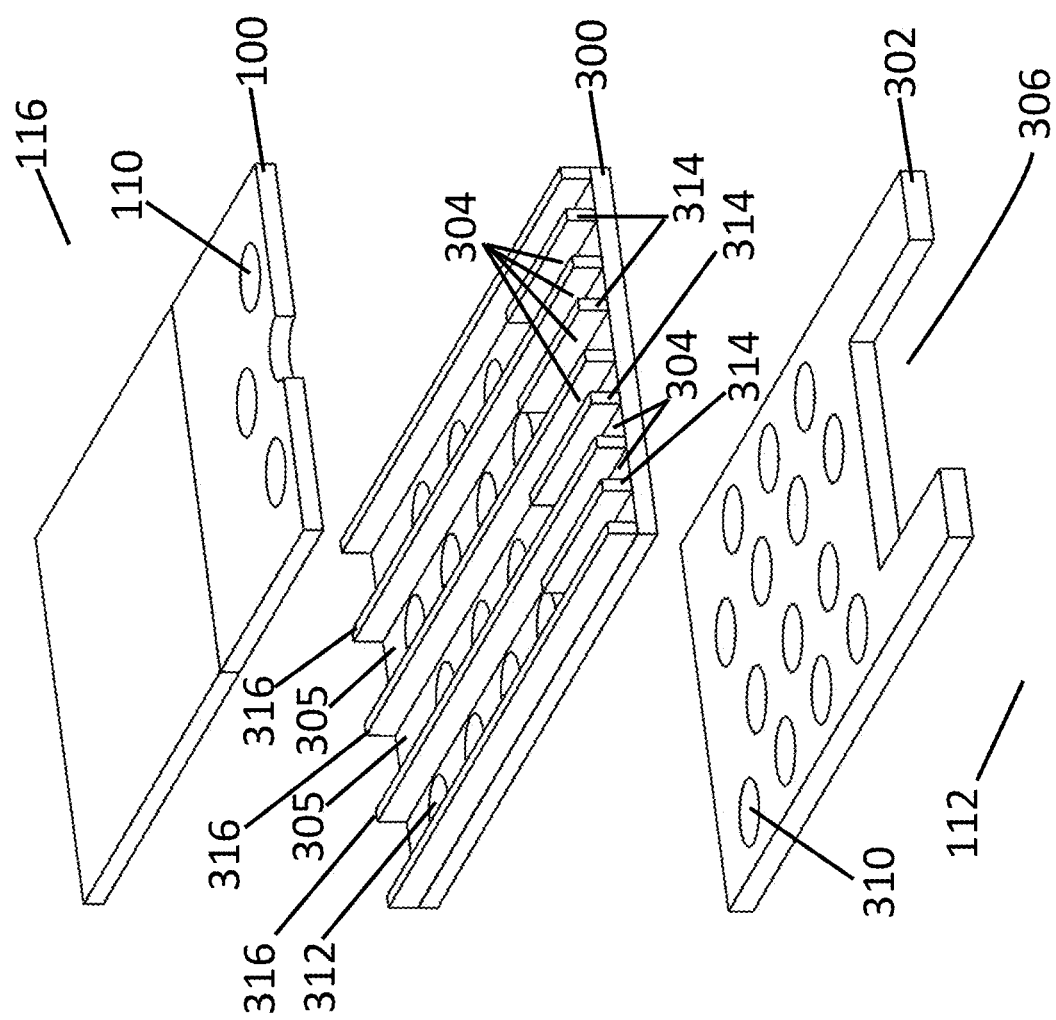
FIGS. 28A and 28B show exploded top and bottom views showing major components of an illustrative embodiment. The view is a cutaway to depict major components.

FIG. 28A shows an exploded top view of an illustrative embodiment. In an embodiment, vaporization ports 110 are formed by etching structure 100. FIG. 5 shows vaporization ports 110 are in thermal communication with heating element 108. In order to better depict the feature shapes, the heat element is omitted from FIG. 28A. The vaporization ports 110 are through-holes that allow fluid communication from one side of structure 100, through structure 100, to a second side of structure 100. In an illustrative embodiment, manifold 300 can interface with structure 100 and manifold extension 302. Ridges 314 and ridges 316 can be formed in manifold 300. In some embodiments, ridges 314 formed in manifold structure 300 only extend partially along the length of manifold 300, as depicted in FIG. 28A. In some embodiments, ridges 316 extend beyond ridges 314. In some embodiments, the length of ridges 316 can be at least twice the length of ridges 314.

In some embodiments, liquid ports 312 can be formed by making through-holes in manifold 300. Liquid port 312 can be formed in manifold structure 300, by wet etching or other microfabrication techniques. Liquid port 312 can allow fluid communication from below manifold 300, through manifold 300, to above manifold 300.

In an embodiment, manifold extension 302 can be optionally interfaced with manifold 300 and liquid source region 112. Liquid port 310 can be formed in manifold extension 302, by anisotropic etching, isotropic wet etching or other microfabrication technique. Liquid port 310 can allow fluid communication from a first side of manifold extension 302, through manifold extension 302, to a second side of manifold extension 302. In some embodiments, liquid port 310 is in fluid communication with liquid source region 112 and liquid port 312. In some embodiments, vaporization ports 110 are in fluid communication with surrounding environment 116.

In some embodiments, flow channels 305 are at least partially enclosed by ridges 316, structure 100 and manifold 300. In some embodiments, flow channels 304 are at least partially enclosed by ridges 314, ridges 316, structure 100, manifold 300. In some embodiments, flow channels 305 are in fluid communication with flow channels 304. In some embodiments flow channels 305 have a larger hydraulic diameter, compared to flow channels 304.

In some embodiments, channels 304 and channels 305 are configured to provide lateral fluid flow, which is defined as principally in a direction that is parallel to the plane of structure 100 and manifold 300.

For the purposes here, a channel is defined as being partially enclosed if at least one region of the channel comprises an inlet, an outlet, and is enclosed on all other sides by structural elements, such as ridge 314, ridge 316, structure 100, and/or manifold 300, and the like. In some embodiments, the length of a region of a channel can be greater than the width of the channel.

In some embodiments, liquid port 310 and liquid port 312 are configured to provide fluid flow that is substantially perpendicular to the plane of the structure, which is defined as principally in a direction normal to the plane of structure 100 and manifold 300.

In some embodiments, flow channels 305 can comprise an average hydrodynamic diameter that is larger than the average hydrodynamic diameter of channels 304. Where hydraulic dynamic diameter Dh is commonly defined as 4 times the ratio of the cross-sectional area A to the wetted perimeter P, such that Dh=4 A/P.

In some embodiments, channel 305 can have a hydraulic diameter that is 1.1-5 times larger compared to channel 304. In some embodiments, channel 305 can have a hydraulic diameter that is 1.25-2 times larger than that of channel 304. In some embodiments, the hydraulic diameters of channels 304 and 305 can range from 1-300 micrometers. In some embodiments, the hydraulic diameters of channels 304 and 305 can range from 10-100 micrometers.

In some embodiments, there can be two or more regions comprised of channels with different hydraulic diameters. For example, in one region channels 305 could provide a larger hydraulic diameter, and in another region channels 304 could provide a smaller hydraulic diameter. In some embodiments, the region with larger hydraulic diameters that are associated with channels 305 could be in fluid communication with liquid port 312 and liquid port 310, which are in fluid communication with liquid source 112. In some embodiments, the region with smaller hydraulic diameters that are associated with channels 304 could be in fluid communication with vaporization ports 110, which are in fluid communication with surrounding environment 116.

In some embodiments, channel 305 can have a cross sectional area that is 1.1-10 times larger compared to channel 304. In some embodiments, channel 305 can have a cross sectional area that is 2-5 times larger compared to channel 304. In some embodiments, channel 304 and channel 305 can have cross sectional areas ranging from 0.00001-1.0 $mm^2$. In some embodiments, channel 304 and channel 305 can have cross sectional areas ranging from 0.0001-0.1 $mm^2$.

In some embodiments, opening 306 can be formed in manifold extension 302 by wet etching or other microfabrication techniques.

Figure 28B:
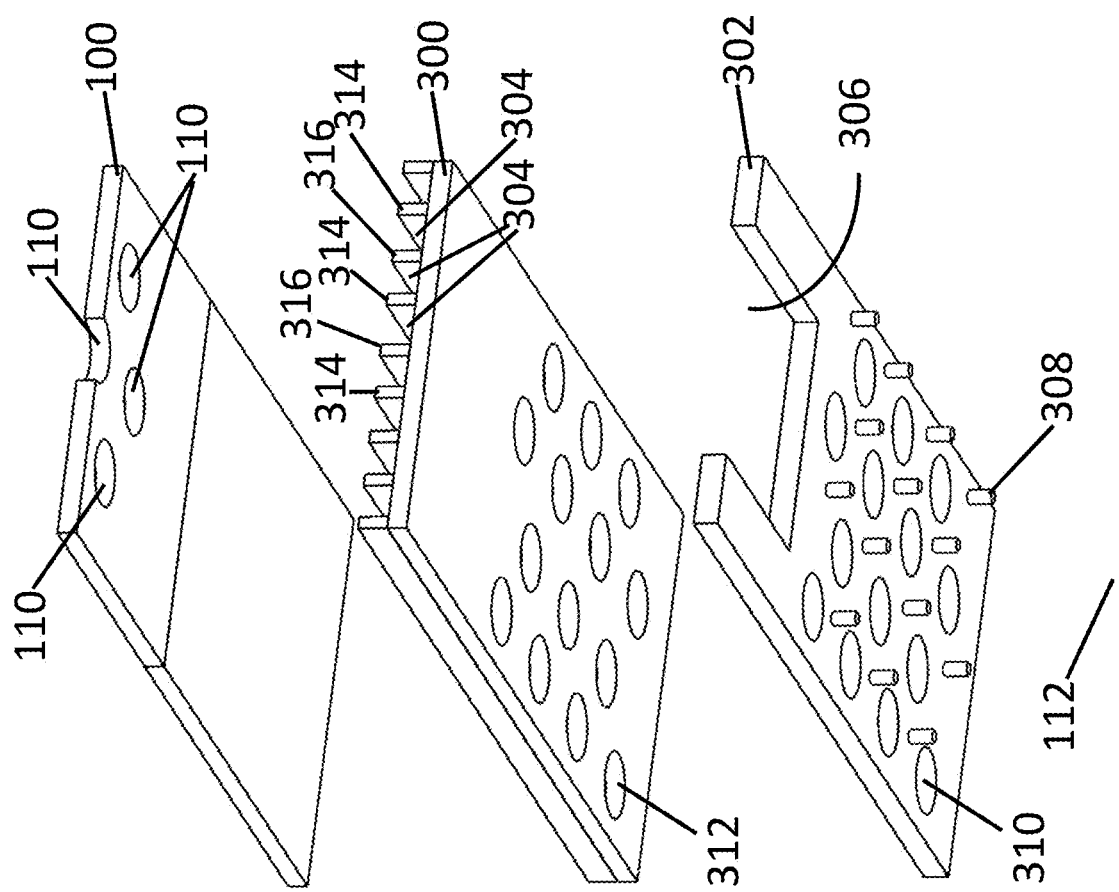

FIG. 28B shows an exploded bottom view of an illustrative embodiment, where three structure layers (structure 100, manifold 300, and manifold extension 302) are interfaced together. In an illustrative embodiment, ridge 314 and ridge 316 are formed by etching manifold 300.

In some embodiments, and in some regions, ridges 314 and ridges 316 are positioned to form channels 304. In some embodiments, liquid source 112 is in fluid communication with liquid ports 310 and liquid ports 312. In some embodiments, channels 304 are flow channels that are at least partially enclosed by ridges 314 and ridges 316, structure 100 and manifold 300. In some embodiments, flow channels 304 are oriented in a lateral direction, which is parallel to the plane of structure 100, and manifold 300.

In an illustrative embodiment, opening 306 can be optionally formed by etching manifold extension 302.

In an illustrative embodiment, wicking pillars 308 can be formed in manifold extension 302. In an illustrative embodiment, liquid port 310 can be formed in manifold extension 302. Wicking pillars 308 and liquid port 310 can be in fluid communication with liquid source region 112. In an illustrative embodiment, opening 306 can provide a gap where air or other low thermal conductivity material, such as aerogel, could confined and create a region of low thermal conductivity. In some embodiments, the bottom surface of manifold 300 can be coated with a hydrophobic coating near opening 306 to decrease wettability and avoid liquid contact with manifold 300. These embodiments could enhance overall vapor/aerosol quality and improve the thermodynamic efficiency of the device by decreasing parasitic heat loss to liquid source region 112, and maintaining desired temperature in structure 100 and manifold 300 near vaporization ports 110.

Figure 29A:
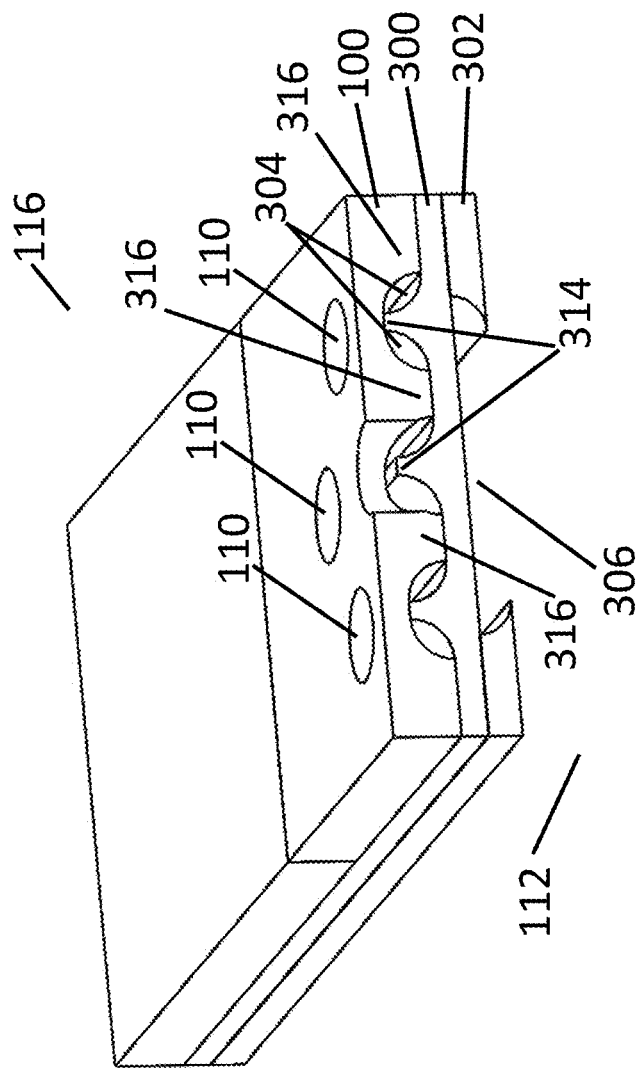
FIGS. 29A and 29B depict top and bottom views of an illustrative embodiment. The view is a cutaway to depict major components.

FIG. 29A depicts a top view of an illustrative embodiment, where three structural layers are interfaced together. Structure 100 comprises a heating element (not shown in FIG. 29A) in thermal communication with vaporization ports 110 (as shown in FIG. 5). Manifold 300 is interfaced to structure 100 and to manifold extension 302. In an illustrative embodiment, ridge 316 is formed by etching structure 100, and ridge 314 is formed by etching manifold 300. In an illustrative embodiment, ridge 314 and ridge 316 can be interdigitated to form channel 304 to reduce the hydraulic diameter in the region of the vaporization ports 110. Flow channels 304 can be in fluid communication with vaporization ports 110. In an illustrative embodiment, opening 306 can be optionally formed by etching manifold extension 302.

In some embodiments, channels 304 are flow channels that are at least partially enclosed by ridges 314 and ridges 316. In some embodiments, channels 304 are flow channels that are at least partially enclosed by ridges 314 and ridges 316, structure 100 and manifold 300.

In other embodiments, only two layers may be optionally used, such as structure 100 and manifold 300.

In some embodiments, structure 100, manifold 300, and manifold extension 302 can be formed by wet etching glass substrates. In other embodiments, structure 100, manifold 300, and manifold extension 302 can be fabricated from plastic, silicon, titanium, metals, ceramics, PDMS, polymers, fiberglass, composites, or other materials.

In some embodiments, structure 100, manifold 300, and manifold extension 302 can be interfaced without bonding, whereby the structural layers are adhered together using stiction, electrostatic attraction, capillary forces, and the like. In some embodiments, structure 100, manifold 300, and manifold extension 302 can be interfaced by known bonding techniques, such as diffusion bonding, eutectic bonding, ambient temperature bonding, adhesive-based bonding, and the like. In some embodiments, structure 100, manifold 300, and manifold extension 302 can be interfaced by mechanical compression.

In FIG. 29A, liquid source region 112 is depicted on one side the apparatus, and surrounding environment 116 is depicted on the opposite the apparatus. In some embodiments, vaporization ports 110 are in fluid communication with surrounding environment 116.

Figure 29B:
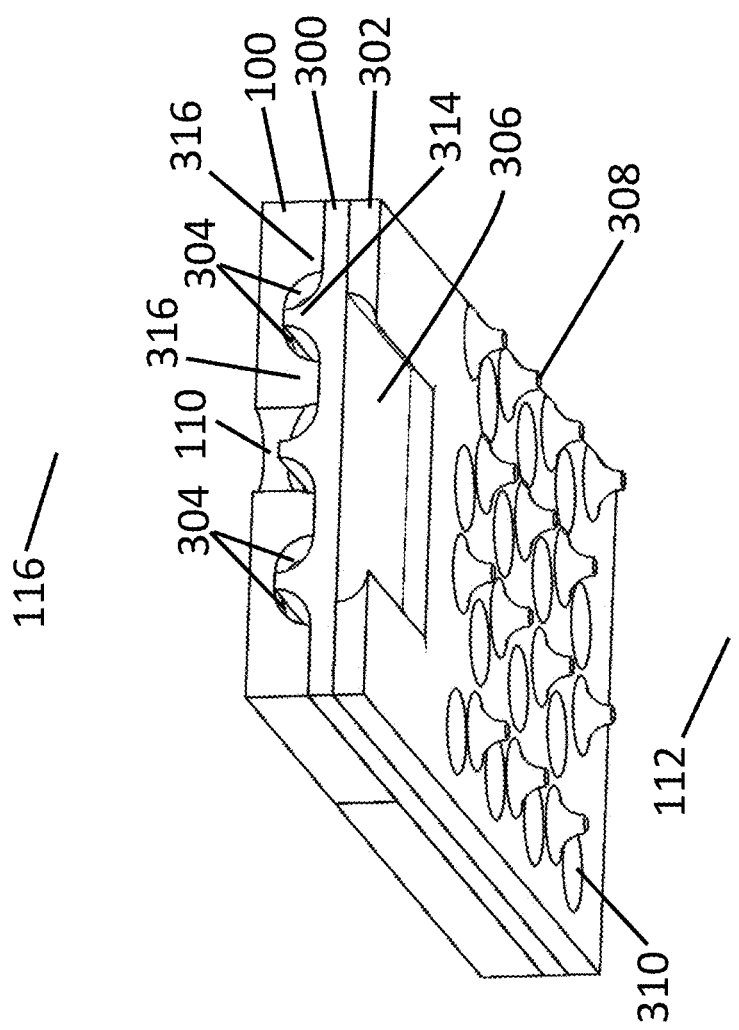

FIG. 29B depicts a bottom view of an illustrative embodiment, where three structure layers (structure 100, manifold 300, and manifold extension 302) are interfaced together. In an illustrative embodiment, ridge 316 is formed by etching structure 100, and ridge 314 is formed by etching manifold 300. In an illustrative embodiment, ridge 314 and ridge 316 can be interdigitated to form flow channel 304. Flow channels 304 can be in fluid communication with vaporization ports 110. In an illustrative embodiment, opening 306 can be optionally formed by etching manifold extension 302.

In an illustrative embodiment, wicking pillars 308 can be formed in manifold extension 302. In an illustrative embodiment, liquid port 310 can be formed in manifold extension 302. Wicking pillars 308 and liquid port 310 are in fluid communication with liquid source region 112. Vaporization ports 110 are in fluid communication with surrounding environment 116.

Figure 30A:
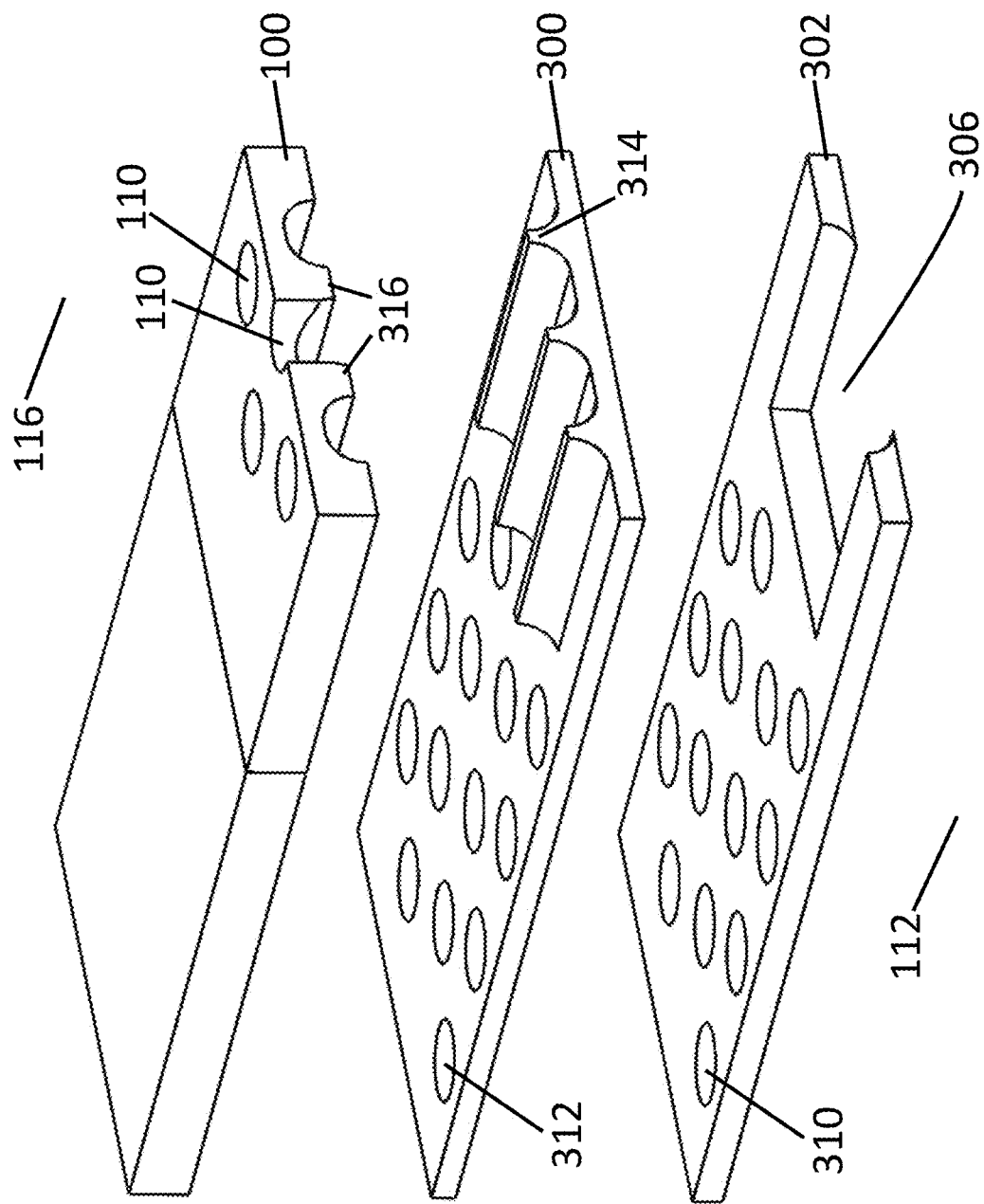
FIGS. 30A and 30B show exploded top and bottom views showing major components of an illustrative embodiment. The view is a cutaway to depict major components.

FIG. 30A shows an exploded top view of an illustrative embodiment. In an embodiment, vaporization ports 110 and ridges 316 are formed by etching structure 100. The vaporization ports 110 are through-holes that allow fluid communication from a first side of structure 100, through structure 100, to a second side of structure 100. In some embodiments, vaporization ports 110 are in fluid communication with surrounding environment 116. Vaporization ports are in thermal communication with heating elements (not shown in FIG. 30A, but shown as heating element 108 in FIG. 5). In an illustrative embodiment, manifold 300 can interface with structure 100 and manifold extension 302. Ridges 314 can be formed in manifold 300. In some embodiments, ridges 314 formed in manifold 300 only extend partially along the length of manifold 300, as depicted in FIG. 30A.

Liquid port 312 can be formed in manifold 300, by wet etching or other microfabrication technique. Liquid port 312 can allow fluid communication from a first side of manifold 300, through manifold 300, to a second side of manifold 300.

In an embodiment, manifold extension 302 can be optionally positioned between manifold 300 and liquid source region 112. Liquid port 310 can be formed in manifold extension 302, by wet etching or other microfabrication technique. Liquid port 310 can allow fluid communication from a first side of manifold extension 302, through manifold extension 302, to a second side of manifold extension 302. Liquid port 312 can allow fluid communication from one side of manifold 300, through manifold 300, to a second side of manifold 300. In some embodiments, liquid port 310 is in fluid communication with liquid source region 112 and liquid port 312.

In some embodiments, opening 306 can be formed in manifold extension 302 by wet etching or other microfabrication technique.

Figure 30B:
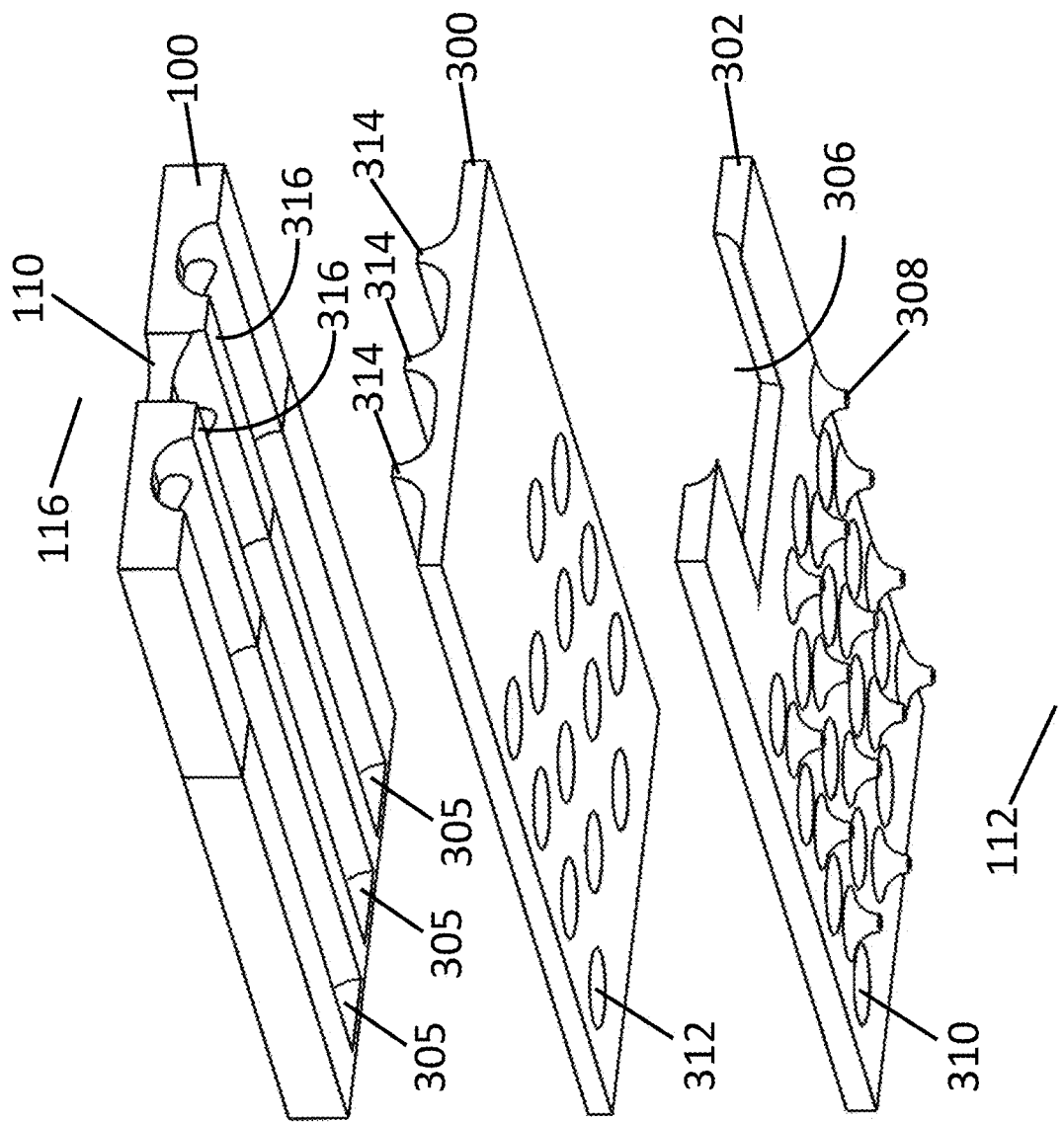

FIG. 30B shows an exploded bottom view of an illustrative embodiment, where three structure layers (structure 100, manifold 300, and manifold extension 302) are interfaced together. In an illustrative embodiment, ridge 316 is formed by etching structure 100, and ridges 314 are formed by etching manifold 300. As illustrated in FIGS. 29A and 29B, ridges 314 and ridges 316 can be interdigitated to form lateral flow channels Surrounding environment 116 can be in fluid communication with vaporization ports 110.

In some embodiments, ridges 314 formed in manifold 300 only extend partially along the length of manifold 300 (as depicted in FIG. 30A). In some embodiments, ridges 316 formed in structure 100 can extend beyond ridges 314. In some embodiments, the length ridges 316 can be at least twice the length of ridges 314. In some embodiments embodiments, ridges 316 can form flow channels 305. Flow channels 305 can be in fluid communication with liquid port 312 (formed in manifold 300).

In some embodiments, flow channels 305 are in fluid communication with liquid ports 312. In some embodiments, channels 305 are flow channels that are at least partially enclosed by ridges 316 structure 100 and manifold 300. In some embodiments, ridges 316 can form walls of flow channels 305.

In some embodiments, ridge 316 can be disposed to be aligned with liquid port 312, such that liquid port 312 is partially occluded by ridge 316. This partial occlusion can be used to facilitate capillary action during the filling process as a liquid/gas meniscus travels through liquid port 312 and into flow channel 305. In some embodiments, ridge 314 can be disposed to be aligned with vaporization port 110, such that vaporization port 110 is partially occluded by ridge 314. This partial occlusion can be used to facilitate capillary action during the filling process as a liquid/gas meniscus travels through flow channels and contacts vaporization port 110.

In an illustrative embodiment, wicking pillars 308 can be formed in manifold extension 302. In an illustrative embodiment, liquid port 310 can be formed in manifold extension 302. Wicking pillars 308 and liquid port 310 are in fluid communication with liquid source region 112. In an illustrative embodiment, opening 306 can provide a gap where air or other low thermal conductivity material, such as aerogel, could confined and create a region of low thermal conductivity. In some embodiments, the bottom surface of manifold 300 can be coated with a hydrophobic coating near opening 306 to decrease wettability and avoid liquid contact with manifold 300. These embodiments could enhance overall vapor/aerosol quality and improve the thermodynamic efficiency of the device by decreasing parasitic heat loss to liquid source region 112, and maintaining desired temperature in structure 100 and manifold 300 near heating element 108 and vaporization ports 110.

In some embodiments, opening 306 can be formed in manifold extension 302 by wet etching or other microfabrication technique.

In some embodiments, flow channels 304 (shown in FIGS. 29A and 29B) and flow channels 305 (shown in FIG. 30B) are oriented in a lateral direction, which is defined as parallel to the plane of structure 100, and manifold 300.

In some embodiments, flow channels 304 (shown in FIGS. 29A and 29B) and flow channels 305 (shown in FIG. 30B) are configured to provide lateral fluid flow, which is defined as principally in a direction that is parallel to the plane of structure 100 and manifold 300.

Referring to FIGS. 29A, 29B, 30A and 30B, and for the purposes here, a channel is defined as being partially enclosed if at least one region of the channel comprises an inlet, an outlet, and is enclosed on all other sides by structural elements, such as ridge 314, ridge 316, structure 100, and/or manifold 300, and the like. In some embodiments, the length of a region of a channel can be greater than the width of the channel.

Referring to FIGS. 30A and 30B, in some embodiments, liquid port 310 and liquid port 312 are configured to provide perpendicular fluid flow, which is defined as principally in a direction normal to the plane of structure 100 and manifold 300.

In some embodiments, channels 305 (shown in FIG. 30B) can comprise an average hydrodynamic diameter that is larger than the average hydrodynamic diameter of channels 304 (shown in FIGS. 29A and 29B). Where hydraulic dynamic diameter Dh is commonly defined as 4 times the ratio of the cross-sectional area A to the wetted perimeter P, such that Dh=4 A/P. In some embodiments, channel 305 can have a hydraulic diameter that is 1.1-5 times larger compared to channel 304. In some embodiments, channel 305 can have a hydraulic diameter that is 1.25-2 times larger than that of channel 304. In some embodiments, the hydraulic diameters of channels 304 and 305 can range from 1-300 micrometers. In some embodiments, the hydraulic diameters of channels 304 and 305 can range from 10-100 micrometers.

In some embodiments, channels 305 (shown in FIG. 30B) are in fluid communication with channels 304 (shown in FIGS. 29A and 29B). In some embodiments, the channels are configured so that the combination provides a larger hydraulic diameter in a first region, and a lower hydraulic diameter in a second region. In some embodiments, the channel with the lower hydraulic diameter is configured to be in fluid communication with vaporization ports 110, as shown in FIGS. 29A and 29B.

In some embodiments, channel 305 (shown in FIG. 30B) can have a cross sectional area that is 1.1-10 times larger compared to channel 304 (shown in FIGS. 29A and 29B). In some embodiments, channel 305 (shown in FIG. 30B) can have a cross sectional area that is 2-5 times larger compared to channel 304 (shown in FIGS. 29A and 29B). In some embodiments, channel 304 and channel 305 (shown in FIG. 30B) can have cross sectional areas ranging from 0.00001-1.0 mm$^2$. In some embodiments, channel 304 and channel 305 can have cross sectional areas ranging from 0.0001-0.1 mm$^2$.

Figure 31A:
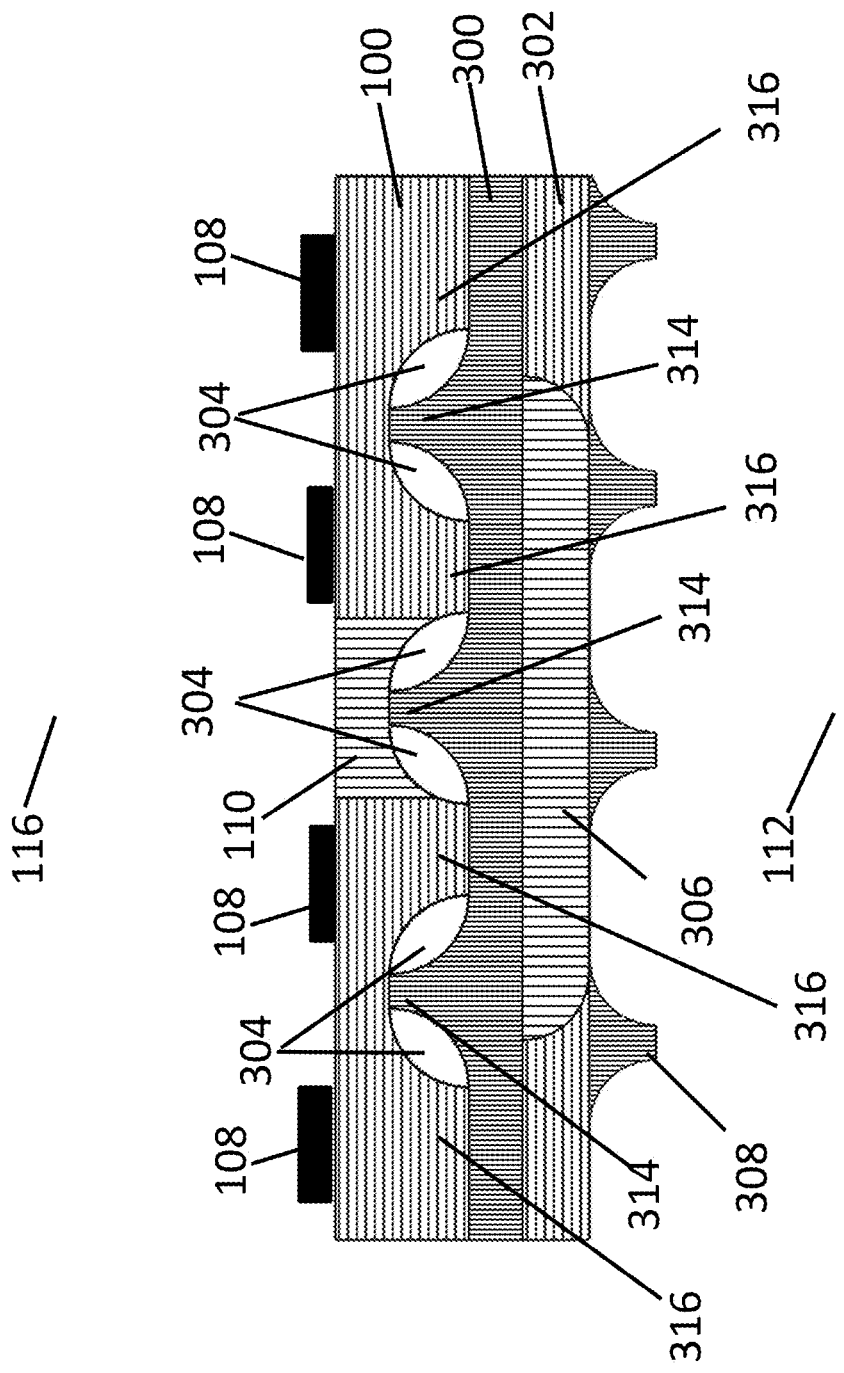
FIGS. 31A and 31B show front views showing major components of an illustrative embodiment. The view is a cutaway to depict major components.

FIG. 31A depicts a front view of an illustrative embodiment, where three structural layers are interfaced together, structure 100, manifold 300, and manifold extension 302. In some embodiments, heating element 108 can be a thin resistive element and position on structure 100, and in thermal communication with vaporization ports 110, ridges 314, ridges 314, flow channels 304, and liquid contained within flow channels 304. Manifold 300 is interfaced to structure 100 and to manifold extension 302. In an illustrative embodiment, ridge 316 is formed by etching structure 100, and ridge 314 is formed by etching manifold 300. In an illustrative embodiment, ridge 314 and ridge 316 can be interdigitated to form channel 304. Flow channels 304 can be in fluid communication with vaporization ports 110. In an illustrative embodiment, opening 306 can be optionally formed by etching manifold extension 302. In some embodiments, wicking pillars 308 are in fluid communication with liquid source 112. In some embodiments, vaporization port 110 is in fluid communication with surrounding environment 116.

In some embodiments, channels 304 are flow channels that are at least partially enclosed by ridges 314 and ridges 316. In some embodiments, channels 304 are flow channels that are at least partially enclosed by ridges 314 and ridges 316, structure 100 and manifold 300.

Figure 31B:
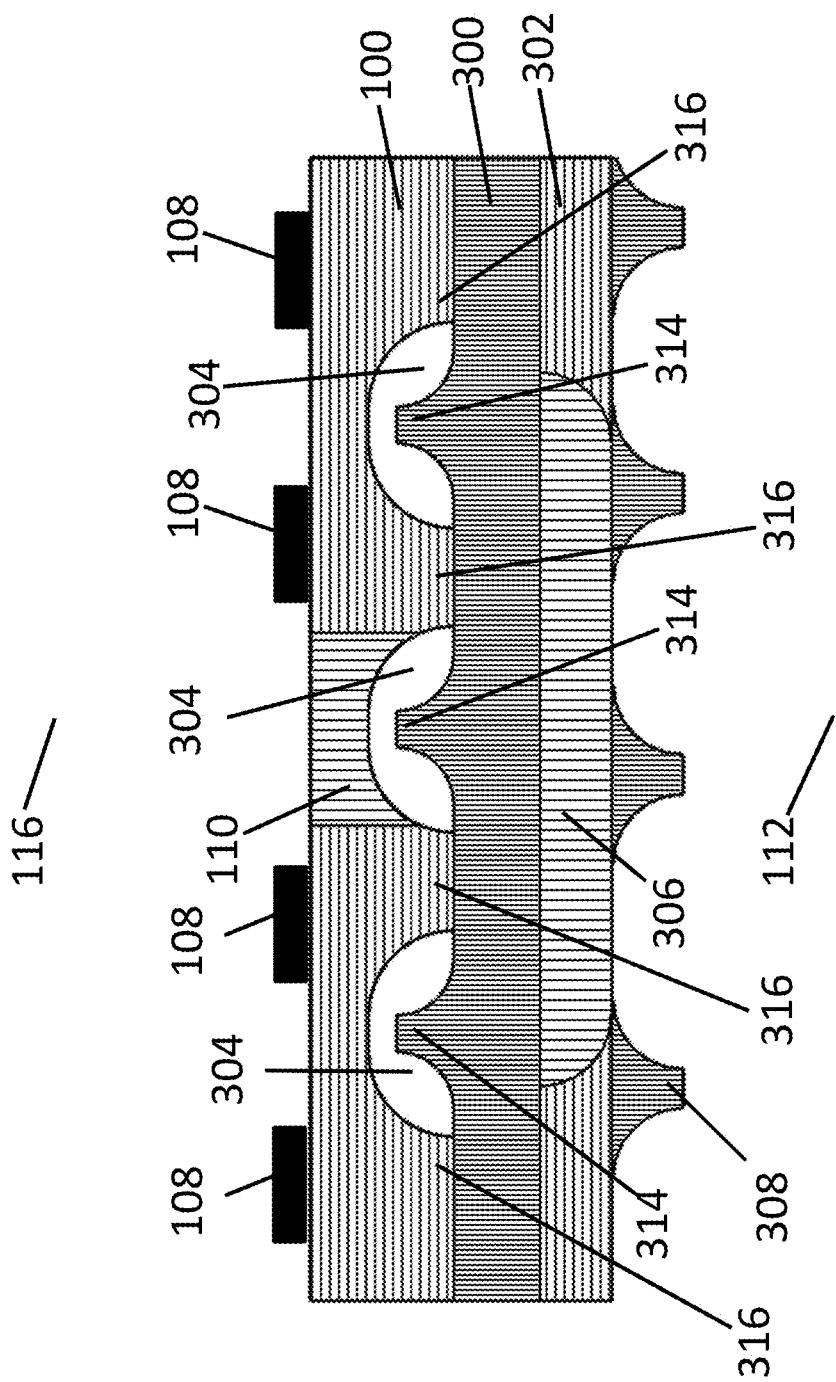

FIG. 31B depicts a front view of an illustrative embodiment, where three structural layers are interfaced together, structure 100, manifold 300, and manifold extension 302. In some embodiments, heating element 108 can be a thin resistive element and position on structure 100, and in thermal communication with vaporization ports 110, ridges 314, ridges 314, flow channels 304, and liquid contained within flow channels 304. Manifold 300 is interfaced to structure 100 and to manifold extension 302. In an illustrative embodiment, ridge 316 is formed by etching structure 100, and ridge 314 is formed by etching manifold 300. In an illustrative embodiment, ridge 314 and ridge 316 can be interdigitated to form channel 304. Flow channels 304 can be in fluid communication with vaporization ports 110. In an illustrative embodiment, opening 306 can be optionally formed by etching manifold extension 302. In some embodiments, wicking pillar 308 is in fluid communication with liquid source 112. In some embodiments, vaporization port 110 is in fluid communication with surrounding environment 116.

In some embodiments, channels 304 are flow channels that are at least partially enclosed by ridges 314 and ridges 316. In some embodiments, channels 304 are flow channels that are at least partially enclosed by ridges 314 and ridges 316, structure 100 and manifold 300. As shown in FIG. 31B, in some embodiments, ridges 314 do not contact structure 100, such that flow channel 304 is contiguously connected on at least two sides of ridge 314.

Figure 32:
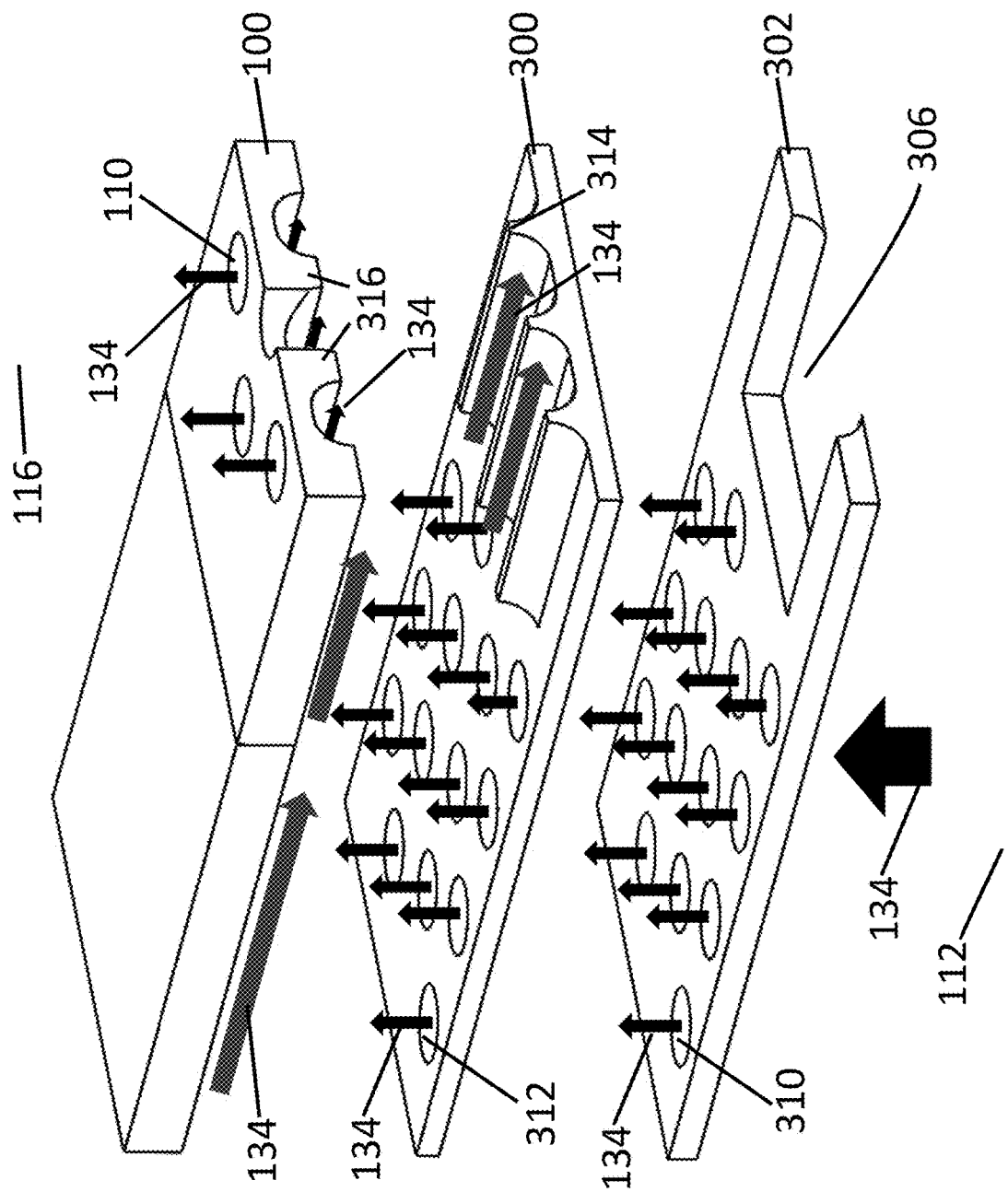
FIG. 32 shows an exploded top view depicting fluid flow paths and some of the major components associated with an illustrative embodiment. The view is a cutaway to depict major components.

FIG. 32 depicts fluid motion that can occur in an illustrative embodiment, using an exploded view of the structure, in a cutaway view. Large arrows 134 depict approximate fluid motion in an illustrative embodiment. In an embodiment, liquid can wick from liquid source region 112. Wicking pillars (not shown) can penetrate into liquid source 112. If liquid source region 112 contains a fibrous wick, wicking pillars can penetrate the interstitial regions between the fibers, which can enhance fluid communication and capillary action between liquid source region 112 and liquid port 310. Wicking pillars can range in size with dimensions from 1 micron to 500 microns. In some embodiments, wicking pillars can range in size with dimensions from 10 microns to 200 microns.

In some embodiments, liquid can flow from liquid source region 112, flow through liquid ports 310 and through liquid ports 312 and into flow channels. In some embodiments, ridges 316 can be positioned directly above or in close proximity to liquid port 312, or positioned to partially occlude liquid ports 312, to enhance liquid wicking into channels 305. Liquid can be transported laterally through the flow channels, and in the plane of structure 100, manifold 300, and manifold extension 302 (as shown in FIG. 32).

In some embodiments, liquid ports 310 and liquid ports 312 can range in size from 1-1000 µm. In some embodiments, liquid ports 310 and liquid ports 312 can range in size from 10 µm-300 µm.

In some embodiments, electrical energy can be applied to an electrode lead and a thin heating element. Joule heating in the heating element can provide thermal energy to heat the region near the heating element. The temperature can be increased to a controlled level near the heating element, in structure 100, manifold 300, vaporization ports 110, and liquid contain in the flow channels, such that the liquid can be vaporized into a vapor or aerosol combination. Vapor can then exit through vaporization ports 110 and be released to the surrounding environment 116, as shown in FIG. 32.

In some embodiments, opening 306 can be formed in manifold extension 302 by etching.

In describing the function of some illustrative embodiments, and referring to FIGS. 29A, 29B, 30A and 30B as a group, the length of ridges 314 can be a controlled dimension, and chosen to specify the length of channels 304. In some embodiments, channels 304 are chosen to have an average hydraulic diameter that is smaller than the average hydraulic diameter of channels 305. In some embodiments, the larger hydraulic dynamic diameter of channels 305 (compared to channels 304) can allow for liquid to be transported with relatively low viscous losses, compared to channels 304.

In some embodiments, channels 304 are chosen to have a smaller hydraulic diameter in comparison to channels 305. This can provide an increased surface to volume ratio in channels 304 (compared to channels 305) (in other words a lower hydraulic diameter), which can have a number of important benefits. For example, a relatively large surface to volume ratio can increase capillary action by increasing the meniscus pressure that can be produced in channels 304. In addition, a large surface area can enhance the amount of thermal energy that can be transported from structure 100, manifold 300, ridges 314 and ridges 316 to liquid in channels 304. An upper limit can be the so-called critical heat flux (CHF), which can limit the rate of heat transfer during a boiling process. By increasing the surface area, the rate of thermal energy delivered to the liquid could be increased. Furthermore, in some embodiments, where channels 304 are formed by ridges 314 and 316, the ridges can provide thermal conduction pathways for thermal energy to be transported, from thin resistive heating elements, to the liquid contained within channels 304.

In some embodiments, the low hydraulic diameter of channels 304 can create significant viscous resistance to liquid flowing in channels 304. This significant viscous resistance can provide a stabilizing effect upon the vaporization process, and reduce undesirable backflow of liquid and vapor combination flowing from channels 304 back into channels 305. This significant viscous resistance can provide a stabilizing effect upon the vaporization process, which can help force vapor/aerosol through vaporization ports 110, which could represent the path of least resistance, and enhance the performance of the apparatus.

In some embodiments, the small hydraulic diameter of channels 304 can create significant viscous resistance to liquid flowing in channels 304. Since channels 304 can be positioned in close proximity to a thin resistive heating element, thermal energy from the heating elements can be conducted through ridges 314 and ridges 316 to the liquid to warm the liquid and increase its temperature. The viscosity of most liquids decreases significantly with increasing temperature. Therefore, in some embodiments, ridges 314 and ridges 316 can be designed in combination with a thin resistive heating element to preheat the liquid to provide a predetermined amount of viscous resistance in channels 304, such that there can be sufficiently large amounts of liquid mass flow rate through channels 304 to achieve the desired amount of vapor/aerosol generation, while simultaneously keeping viscous resistance in channels 304 sufficiently high to maintain stable vaporization.

In general, for some embodiments, the apparatus is filled by liquid from a liquid source region that is wicked due to capillary action through the liquid ports and into a lateral flow channel, which has a relatively large hydraulic diameter. This larger hydraulic diameter allows the liquid to flow laterally and parallel to the plane of the manifold substrate with relatively small viscous losses. The liquid is then wicked by capillary action from the flow channels with a larger hydraulic diameter into flow channels that have a lower hydraulic diameter. The smaller hydraulic diameter flow channel provides a larger surface to volume ratio, which increases the capillary effect and provides a high-pressure difference across a liquid/vapor meniscus.

In some embodiments, and under quasi-steady operation, electrical energy is applied to heating elements, wherein Joule heating converts electrical energy into thermal energy. The thermal energy heats the structure and manifold near the vaporization ports, which causes liquid to change phase into a vapor/aerosol combination. Capillary action from the liquid/vapor meniscus, contained either within the vaporization ports or within the flow channels with the low hydraulic diameter, draws liquid from the liquid source through the liquid ports and into the lateral flow channels. This liquid replaces the previous vaporized liquid, and allows the process to continue. The combination of lateral flow channels with larger and smaller hydraulic diameters, allows liquid to be transported with low viscous losses in one region of the manifold, while maintaining high capillary pressure due to the meniscus in another region of the manifold.

In some embodiments, thermal energy from a thin resistive heating element can be conducted through structure 100, manifold 300, ridges 316, and ridges 314 and cause phase change from liquid to vapor/aerosol that can take place in the vaporization ports 110, in channels 304, or in combination of vaporization ports 110 and channels 304. In some embodiments, both liquid and vapor can travel through vaporization ports 110 and be released to the surrounding atmosphere 116.

In an illustrative embodiment, opening 306 can be disposed below a thin resistive heating element and vaporization ports 110, and can provide a gap where air or other low thermal conductivity material, such as aerogel, could confined and create a region of low thermal conductivity. In some embodiments, the bottom surface of manifold 300 can be coated with a hydrophobic coating near opening 306 to decrease wettability and avoid liquid contact with manifold 300. These embodiments could enhance overall vapor/aerosol quality and improve the thermodynamic efficiency of the device by forming a thermal barrier thereby decreasing parasitic heat loss from manifold 300 to liquid source region 112, and maintaining desired temperature in structure 100 and manifold 300 near heating element 108 and vaporization ports 110. In some embodiments, structure 100, manifold 300, and manifold extension 302 are aligned with respect to one another by means of one or more features such as etched grooves, mechanical alignment pins, detents, and the like. The alignment features may be arranged such that one or more of structure 100, manifold 300, manifold extension 302 may be aligned with respect to each other along a particular dimension such as the width or length or both.

Figure 33:
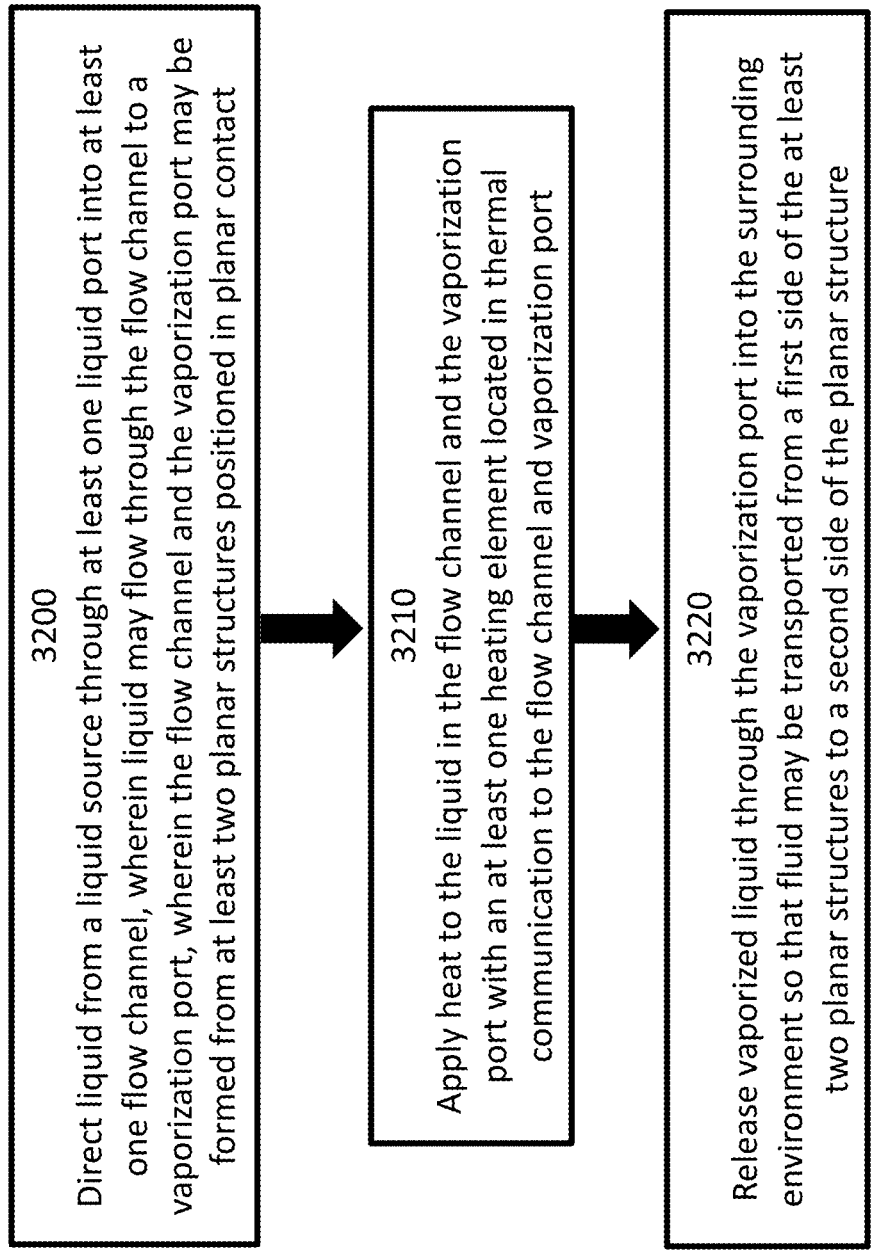
FIG. 33 is a flow chart showing an exemplary method embodiment

FIG. 33 shows a flow chart for an exemplary method embodiment utilizing a vaporization apparatus as disclosed herein for vaporizing liquid into a surrounding environment.

In step 3200 method direct liquid from a liquid source through at least one liquid port into at least one flow channel, wherein liquid may flow through the flow channel to a vaporization port, wherein the flow channel and the vaporization port may be formed from at least two planar structures positioned in planar contact. In this step liquid is drawn from the source into the apparatus and transported through channels to the part of the apparatus that vaporizes the transported fluid.

In step 3210, apply heat to the liquid in the flow channel and the vaporization port with an at least one heating element located in thermal communication to the flow channel and vaporization port. In this step the transported liquid is vaporized.

In step 3220 vaporized liquid through the vaporization port into the surrounding environment so that fluid may be transported from a first side of the at least two planar structures to a second side of the planar structure.

The embodiments described herein are exemplary. Modifications, rearrangements, substitute processes, materials, etc. may be made to these embodiments and still be encompassed within the teachings set forth herein.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "an element configured to carry out recitations A, B and C" can include a first element configured to carry out recitation A working in conjunction with a second elements configured to carry out recitations B and C.

While the above detailed description has shown, described, and pointed out novel features as applied to illustrative embodiments, it will be understood that various omissions, substitutions, and changes in the form and details of the devices or methods illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A vaporization apparatus that is placed within a surrounding environment and configured to vaporize liquid from a liquid source into the surrounding environment, comprising:
   at least one liquid source;
   a first planar structure;
   a second planar structure in fluid contact with the liquid source, configured with at least one ridge structure and at least one through hole to deliver liquid from the liquid source to the first planar structure by surface tension;
   the second planar structure is made from metal;
   a plurality of vaporization ports that are formed in the first planar structure comprising a through hole;

wherein the through hole in the first planar structure is configured with lateral dimensions ranging from 10 um to 300 um;

wherein the first planar structure is in fluid contact with liquid from the second planar structure on a first side, and a surrounding environment on a second side;

wherein fluid is transported from the first side of the first planar structure to the second side of the first planar structure through the through hole in the first planar structure;

the dimension of the vaporization ports and the planar structure materials are selected to wick liquid from the liquid source by surface tension;

at least one of a plurality of planar heating elements or a continuous planar heating element, comprising thin film resistive elements formed on the second side of the first planar structure and disposed around at least part of at least one vaporization port; wherein;

the first planar structure and the planar heating elements are microfabricated; and, heat applied from the planar heating element, through the first planar structure to liquid that is in direct contact with the first planar structure, vaporizes the liquid thereby releasing vapor through the plurality of vaporization ports into the surrounding environment.

2. The vaporization apparatus of claim 1 wherein the metal includes titanium or titanium alloys.

3. The vaporization apparatus of claim 1 wherein the second planar structure is made using an etching process, including wet-etching.

4. A vaporization apparatus that is placed within a surrounding environment to vaporize liquid into the surrounding environment, comprising:
   at least one liquid source;
   a microfluidic chip, comprising:
      a plurality of vaporization ports formed in a planar structure comprising a through hole, the through hole with lateral dimensions ranging from 10 urn to 300 um, that is in fluid communication with the liquid source on a first side and the surrounding environment on a second side, wherein fluid is transported from the first side of the structure to the second side of the structure through the through hole;
      at least one planar heating element formed on the second side of the planar structure and disposed around a plurality of vaporization ports, wherein
      the at least one planar heating element and the plurality of vaporization ports are microfabricated,
      the dimension of the vaporization ports and the planar structure materials are selected to wick liquid from the liquid source by surface tension, and
      heat applied from the heating element, through the planar structure to liquid that is in direct contact with the planar structure, vaporizes the liquid thereby releasing vapor through the vaporization ports into the surrounding environment;
   a body comprising:
      a housing comprising a mounting region for the microfluidic chip;
      a retaining element configured to retain the microfluidic chip comprising a vaporization region;
      an electrical connection from the exterior of the body to the microfluidic chip; and,
      a second planar structure in fluid contact with the liquid source, configured with at least one ridge structure and at least one through hole to deliver liquid from the liquid source to the first planar structure by surface tension.

5. The vaporization apparatus of claim 4 wherein the body elements are made from at least one of a large selection of plastics, metals, fiberglass, composites, ceramics, or other structural materials.

6. The vaporization apparatus of claim 4 wherein the metals include titanium and titanium alloys.

7. The vaporization apparatus of claim 4 wherein the second planar structure is made from at least one of a large selection of plastics, metals, fiberglass, composites, ceramics, or other structural materials.

8. The vaporization apparatus of claim 7 wherein the metals include titanium and titanium alloys.

9. The vaporization apparatus of claim 8 wherein the second planar structure is formed using an etching process, including wet-etching, on the titanium or titanium alloy.

* * * * *